(12) United States Patent
Hess et al.

(10) Patent No.: US 8,991,676 B2
(45) Date of Patent: *Mar. 31, 2015

(54) SURGICAL STAPLE HAVING A SLIDABLE CROWN

(75) Inventors: Christopher J. Hess, Cincinnati, OH (US); William B. Weisenburgh, II, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1943 days.

This patent is subject to a terminal disclaimer.

(21) Appl. No.: 11/824,251

(22) Filed: Jun. 29, 2007

(65) Prior Publication Data
US 2009/0005807 A1    Jan. 1, 2009

(51) Int. Cl.
*A61B 17/04*    (2006.01)
*A61B 17/068*   (2006.01)
*A61B 17/064*   (2006.01)
(Continued)

(52) U.S. Cl.
CPC .......... *A61B 17/0682* (2013.01); *A61B 17/064* (2013.01); *A61B 17/0644* (2013.01); *A61B 17/07207* (2013.01); *A61B 17/07292* (2013.01); *A61B 17/1114* (2013.01); *A61B 17/115* (2013.01); *A61B 17/135* (2013.01); *A61B 17/072* (2013.01); *A61B 19/54* (2013.01); *A61B 2017/00004* (2013.01); *A61B 2017/00526* (2013.01); *A61B 2017/00818* (2013.01); *A61B 2017/00893* (2013.01); *A61B 2017/00898* (2013.01); *A61B 2017/07228* (2013.01); *A61B 2017/2905* (2013.01); *A61B 2017/2927* (2013.01); *A61B 2017/320052* (2013.01); *A61B 2019/307* (2013.01); *Y10S 227/902* (2013.01)
USPC ........................................ 227/175.1; 227/902

(58) Field of Classification Search
USPC .......................... 227/19, 175.1; 606/219, 220
See application file for complete search history.

(56) References Cited

U.S. PATENT DOCUMENTS

| 66,052 A | 6/1867 | Smith |
| 1,306,107 A | 6/1919 | Elliott |

(Continued)

FOREIGN PATENT DOCUMENTS

| CA | 2458946 A1 | 3/2003 |
| CA | 2512960 A1 | 1/2006 |

(Continued)

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

(Continued)

*Primary Examiner* — Gregory Anderson
*Assistant Examiner* — Christina Lauer

(57) ABSTRACT

A surgical staple including a deformable member and a crown, where the deformable member can slide relative to the crown. In at least one embodiment, a staple cartridge can include a cavity and a deck, where the cavity can be configured to receive at least a portion of the deformable member and the crown can be positioned within an opening in the deck. In various embodiments, when soft tissue is captured between an anvil and the staple cartridge, the crown can apply a compressive force or pressure to the soft tissue even before the deformable member is deployed toward the anvil.

2 Claims, 90 Drawing Sheets

(51) Int. Cl.
  *A61B 17/072* (2006.01)
  *A61B 17/11* (2006.01)
  *A61B 17/115* (2006.01)
  *A61B 17/135* (2006.01)
  *A61B 19/00* (2006.01)
  *A61B 17/00* (2006.01)
  *A61B 17/29* (2006.01)
  *A61B 17/32* (2006.01)

(56) References Cited

U.S. PATENT DOCUMENTS

| | | |
|---|---|---|
| 2,037,727 A | 4/1936 | La Chapelle |
| 2,214,870 A | 9/1940 | West |
| 2,441,096 A | 5/1948 | Happe |
| 2,526,902 A | 10/1950 | Rublee |
| 2,804,848 A | 9/1957 | O'Farrell et al. |
| 2,808,482 A | 10/1957 | Zanichkowsky et al. |
| 2,853,074 A | 9/1958 | Olson |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,266,494 A | 8/1966 | Brownrigg et al. |
| 3,269,630 A | 8/1966 | Fleischer |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,499,591 A | 3/1970 | Green |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,751,902 A | 8/1973 | Kingsbury et al. |
| 3,819,100 A | 6/1974 | Noiles et al. |
| 3,821,919 A | 7/1974 | Knohl |
| 3,841,474 A | 10/1974 | Maier |
| 3,892,228 A | 7/1975 | Mitsui |
| 3,894,174 A | 7/1975 | Cartun |
| 3,940,844 A | 3/1976 | Colby et al. |
| 4,054,108 A | 10/1977 | Gill |
| 4,106,446 A | 8/1978 | Yamada et al. |
| 4,111,206 A | 9/1978 | Vishnevsky et al. |
| 4,129,059 A | 12/1978 | Van Eck |
| 4,213,562 A | 7/1980 | Garrett et al. |
| 4,244,372 A | 1/1981 | Kapitanov et al. |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A * | 9/1983 | Green ............ 227/19 |
| 4,415,112 A | 11/1983 | Green |
| 4,428,376 A | 1/1984 | Mericle |
| 4,429,695 A | 2/1984 | Green |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,629,107 A | 12/1986 | Fedotov et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,662,555 A | 5/1987 | Thornton |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,693,248 A | 9/1987 | Failla |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,834,720 A | 5/1989 | Blinkhorn |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,892,244 A | 1/1990 | Fox et al. |
| 4,915,100 A | 4/1990 | Green |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |

(56) References Cited

U.S. PATENT DOCUMENTS

| | | |
|---|---|---|
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,158,567 A | 10/1992 | Green |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A * | 2/1994 | Hermes .......................... 606/219 |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,318,221 A | 6/1994 | Green et al. |
| 5,330,502 A | 7/1994 | Hassler et al. |
| 5,332,142 A | 7/1994 | Robinson et al. |
| 5,333,422 A | 8/1994 | Warren et al. |
| 5,334,183 A | 8/1994 | Wuchinich |
| 5,339,799 A | 8/1994 | Kami et al. |
| 5,341,724 A | 8/1994 | Vatel |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,364,003 A | 11/1994 | Williamson, IV |
| 5,366,134 A | 11/1994 | Green et al. |
| 5,366,479 A | 11/1994 | McGarry et al. |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,397,046 A | 3/1995 | Savage et al. |
| 5,397,324 A * | 3/1995 | Carroll et al. .................. 606/139 |
| 5,403,312 A | 4/1995 | Yates et al. |
| 5,405,072 A | 4/1995 | Zlock et al. |
| 5,405,344 A | 4/1995 | Williamson et al. |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,439,156 A | 8/1995 | Grant et al. |
| 5,441,191 A | 8/1995 | Linden |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,452,836 A | 9/1995 | Huitema et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,465,894 A | 11/1995 | Clark et al. |
| 5,465,895 A | 11/1995 | Knodel et al. |

(56) References Cited

U.S. PATENT DOCUMENTS

| | | |
|---|---|---|
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,628 A | 8/1996 | Cooper et al. |
| 5,549,637 A | 8/1996 | Crainich |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,571,090 A | 11/1996 | Sherts |
| 5,571,100 A | 11/1996 | Goble et al. |
| 5,571,116 A | 11/1996 | Bolanos et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,611,709 A | 3/1997 | McAnulty |
| 5,613,966 A | 3/1997 | Makower et al. |
| 5,618,294 A | 4/1997 | Aust et al. |
| 5,618,303 A | 4/1997 | Marlow et al. |
| 5,620,289 A | 4/1997 | Curry |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |

(56) References Cited

U.S. PATENT DOCUMENTS

| | | |
|---|---|---|
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,806,676 A | 9/1998 | Wasgien |
| 5,807,393 A | 9/1998 | Williamson, IV et al. |
| 5,809,441 A | 9/1998 | McKee |
| 5,810,811 A | 9/1998 | Yates et al. |
| 5,810,855 A | 9/1998 | Rayburn et al. |
| 5,813,813 A | 9/1998 | Daum et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,846,254 A | 12/1998 | Schulze et al. |
| 5,855,311 A | 1/1999 | Hamblin et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A | 9/1999 | Viola et al. |
| 5,964,774 A | 10/1999 | McKean et al. |
| 5,988,479 A | 11/1999 | Palmer |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,017,356 A | 1/2000 | Frederick et al. |
| 6,022,352 A | 2/2000 | Vandewalle |

(56) References Cited

U.S. PATENT DOCUMENTS

| | | |
|---|---|---|
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,045,560 A | 4/2000 | McKean et al. |
| 6,050,472 A | 4/2000 | Shibata |
| 6,053,922 A | 4/2000 | Krause et al. |
| 6,056,746 A | 5/2000 | Goble et al. |
| 6,063,097 A | 5/2000 | Oi et al. |
| 6,068,627 A | 5/2000 | Orszulak et al. |
| 6,071,233 A | 6/2000 | Ishikawa et al. |
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,162,208 A | 12/2000 | Hipps |
| 6,165,175 A | 12/2000 | Wampler et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,179,776 B1 | 1/2001 | Adams et al. |
| 6,181,105 B1 | 1/2001 | Cutolo et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,761 B1 | 12/2001 | Kumar et al. |
| 6,336,926 B1 | 1/2002 | Goble |
| 6,346,077 B1 | 2/2002 | Taylor et al. |
| 6,352,503 B1 | 3/2002 | Matsui et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,387,113 B1 | 5/2002 | Hawkins et al. |
| 6,387,114 B2 | 5/2002 | Adams |
| 6,398,781 B1 | 6/2002 | Goble et al. |
| 6,398,797 B2 | 6/2002 | Bombard et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| RE37,814 E | 8/2002 | Allgeyer |
| 6,436,097 B1 | 8/2002 | Nardella |
| 6,436,107 B1 | 8/2002 | Wang et al. |
| 6,436,122 B1 | 8/2002 | Frank et al. |
| 6,440,146 B2 | 8/2002 | Nicholas et al. |
| 6,443,973 B1 | 9/2002 | Whitman |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |

(56) References Cited

U.S. PATENT DOCUMENTS

| | | |
|---|---|---|
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,685,727 B2 | 2/2004 | Fisher et al. |
| 6,695,199 B2 | 2/2004 | Whitman |
| 6,698,643 B2 | 3/2004 | Whitman |
| 6,704,210 B1 | 3/2004 | Myers |
| 6,705,503 B1 | 3/2004 | Pedicini et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,843,403 B2 | 1/2005 | Whitman |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,863,694 B1 | 3/2005 | Boyce et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,868 B2 | 5/2006 | Greene et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,684 B2 | 8/2006 | McGuckin, Jr. et al. |
| 7,094,202 B2 | 8/2006 | Nobis et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |

(56) References Cited

U.S. PATENT DOCUMENTS

| | | |
|---|---|---|
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,188,758 B2 | 3/2007 | Viola et al. |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,220,260 B2 | 5/2007 | Fleming et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,324,572 B2 | 1/2008 | Chang |
| 7,328,828 B2 | 2/2008 | Ortiz et al. |
| 7,328,829 B2 | 2/2008 | Arad et al. |
| 7,336,184 B2 | 2/2008 | Smith et al. |
| 7,338,513 B2 | 3/2008 | Lee et al. |
| 7,348,763 B1 | 3/2008 | Reinhart et al. |
| 7,351,258 B2 | 4/2008 | Ricotta et al. |
| 7,354,447 B2 | 4/2008 | Shelton, IV et al. |
| 7,364,060 B2 | 4/2008 | Milliman |
| 7,377,928 B2 | 5/2008 | Zubik et al. |
| 7,388,217 B2 | 6/2008 | Buschbeck et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,418,078 B2 | 8/2008 | Blanz et al. |
| 7,419,080 B2 | 9/2008 | Smith et al. |
| 7,422,136 B1 | 9/2008 | Marczyk |
| 7,424,965 B2 | 9/2008 | Racenet et al. |
| 7,431,188 B1 | 10/2008 | Marczyk |
| 7,431,694 B2 | 10/2008 | Stefanchik et al. |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |
| 7,441,685 B1 | 10/2008 | Boudreaux |
| 7,455,208 B2 | 11/2008 | Wales et al. |
| 7,461,767 B2 | 12/2008 | Viola et al. |
| 7,464,847 B2 | 12/2008 | Viola et al. |
| 7,472,814 B2 | 1/2009 | Mastri et al. |
| 7,473,253 B2 | 1/2009 | Dycus et al. |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,506,790 B2 | 3/2009 | Shelton, IV |
| 7,510,107 B2 | 3/2009 | Timm et al. |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,563,862 B2 | 7/2009 | Sieg et al. |
| 7,566,300 B2 | 7/2009 | Devierre et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,611,038 B2 | 11/2009 | Racenet et al. |
| 7,615,003 B2 | 11/2009 | Stefanchik et al. |
| 7,631,793 B2 | 12/2009 | Rethy et al. |
| 7,641,091 B2 | 1/2010 | Olson et al. |
| 7,641,093 B2 | 1/2010 | Doll et al. |
| 7,651,498 B2 | 1/2010 | Shifrin et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 7,674,255 B2 | 3/2010 | Braun |
| 7,682,307 B2 | 3/2010 | Danitz et al. |
| 7,686,826 B2 | 3/2010 | Lee et al. |
| 7,691,098 B2 | 4/2010 | Wallace et al. |
| 7,699,204 B2 | 4/2010 | Viola |
| 7,717,312 B2 | 5/2010 | Beetel |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,936 B2 | 5/2010 | Shalton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,743,960 B2 | 6/2010 | Whitman et al. |
| 7,744,627 B2 | 6/2010 | Orban, III et al. |
| 7,748,587 B2 | 7/2010 | Haramiishi et al. |
| 7,753,245 B2 | 7/2010 | Boudreaux et al. |
| 7,766,209 B2 | 8/2010 | Baxter, III et al. |
| 7,771,396 B2 | 8/2010 | Stefanchik et al. |
| 7,780,054 B2 | 8/2010 | Wales |
| 7,780,685 B2 | 8/2010 | Hunt et al. |
| 7,784,662 B2 | 8/2010 | Wales et al. |

(56) References Cited

U.S. PATENT DOCUMENTS

| | | |
|---|---|---|
| 7,789,889 B2 | 9/2010 | Zubik et al. |
| 7,793,812 B2 | 9/2010 | Moore et al. |
| 7,798,386 B2 | 9/2010 | Schall et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,401 B2 | 11/2010 | Manzo et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,836,400 B2 | 11/2010 | May et al. |
| 7,845,533 B2 | 12/2010 | Marczyk et al. |
| 7,845,534 B2 | 12/2010 | Viola et al. |
| 7,866,528 B2 | 1/2011 | Olson et al. |
| 7,870,989 B2 | 1/2011 | Viola et al. |
| 7,887,530 B2 | 2/2011 | Zemlok et al. |
| 7,909,191 B2 | 3/2011 | Baker et al. |
| 7,909,220 B2 | 3/2011 | Viola |
| 7,922,063 B2 | 4/2011 | Zemlok et al. |
| 7,951,166 B2 | 5/2011 | Orban et al. |
| 8,016,177 B2 | 9/2011 | Bettuchi et al. |
| 8,123,767 B2 | 2/2012 | Bauman et al. |
| 8,127,975 B2 | 3/2012 | Olson et al. |
| 8,162,138 B2 | 4/2012 | Bettenhausen et al. |
| 8,192,460 B2 | 6/2012 | Orban, III et al. |
| 8,231,041 B2 | 7/2012 | Marczyk et al. |
| 8,245,901 B2 | 8/2012 | Stopek |
| 8,308,042 B2 | 11/2012 | Aranyi |
| 8,308,046 B2 | 11/2012 | Prommersberger |
| 8,328,062 B2 | 12/2012 | Viola |
| 8,336,753 B2 | 12/2012 | Olson et al. |
| 8,403,198 B2 | 3/2013 | Sorrentino et al. |
| 8,453,904 B2 | 6/2013 | Eskaros et al. |
| 8,464,925 B2 | 6/2013 | Hull et al. |
| 8,668,130 B2 | 3/2014 | Hess et al. |
| 8,763,875 B2 | 7/2014 | Morgan et al. |
| 2002/0022836 A1 | 2/2002 | Goble et al. |
| 2002/0029036 A1 | 3/2002 | Goble et al. |
| 2002/0117534 A1 | 8/2002 | Green et al. |
| 2002/0134811 A1 | 9/2002 | Napier et al. |
| 2002/0165541 A1 | 11/2002 | Whitman |
| 2003/0023316 A1 | 1/2003 | Brown et al. |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0216732 A1 | 11/2003 | Truckai et al. |
| 2003/0220660 A1 | 11/2003 | Kortenbach et al. |
| 2004/0002726 A1 | 1/2004 | Nunez et al. |
| 2004/0006340 A1 | 1/2004 | Latterell et al. |
| 2004/0006372 A1 | 1/2004 | Racenet et al. |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0078037 A1 | 4/2004 | Batchelor et al. |
| 2004/0094597 A1 | 5/2004 | Whitman et al. |
| 2004/0097987 A1 | 5/2004 | Pugsley et al. |
| 2004/0101822 A1 | 5/2004 | Wiesner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0122471 A1 | 6/2004 | Toby et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0023324 A1 | 2/2005 | Doll et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059996 A1 * | 3/2005 | Bauman et al. .............. 606/215 |
| 2005/0059997 A1 | 3/2005 | Bauman et al. |
| 2005/0070929 A1 | 3/2005 | Dalessandro et al. |
| 2005/0070958 A1 | 3/2005 | Swayze et al. |
| 2005/0072827 A1 | 4/2005 | Mollenauer |
| 2005/0080454 A1 | 4/2005 | Drews et al. |
| 2005/0085693 A1 | 4/2005 | Belson et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145671 A1 | 7/2005 | Viola |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263562 A1 | 12/2005 | Shelton, IV et al. |
| 2005/0263563 A1 | 12/2005 | Racenet et al. |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0025811 A1 | 2/2006 | Shelton |
| 2006/0025812 A1 | 2/2006 | Shelton |
| 2006/0025813 A1 | 2/2006 | Shelton et al. |
| 2006/0047275 A1 | 3/2006 | Goble |
| 2006/0047303 A1 | 3/2006 | Ortiz et al. |
| 2006/0047307 A1 | 3/2006 | Ortiz et al. |

(56) References Cited

U.S. PATENT DOCUMENTS

| | | |
|---|---|---|
| 2006/0047308 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111710 A1 | 5/2006 | Goble et al. |
| 2006/0111711 A1 | 5/2006 | Goble |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0151567 A1 | 7/2006 | Roy |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0190028 A1 | 8/2006 | Wales et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034666 A1 | 2/2007 | Holsten et al. |
| 2007/0034668 A1 | 2/2007 | Holsten et al. |
| 2007/0045379 A1 | 3/2007 | Shelton, IV |
| 2007/0055219 A1 | 3/2007 | Whitman et al. |
| 2007/0070574 A1 | 3/2007 | Nerheim et al. |
| 2007/0073340 A1 | 3/2007 | Shelton, IV et al. |
| 2007/0073341 A1 | 3/2007 | Smith |
| 2007/0075114 A1 | 4/2007 | Shelton, IV et al. |
| 2007/0078484 A1 | 4/2007 | Talarico et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0135803 A1 | 6/2007 | Belson |
| 2007/0158358 A1 | 7/2007 | Mason, II et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton et al. |
| 2007/0243227 A1 | 10/2007 | Gertner |
| 2007/0246505 A1 | 10/2007 | Pace-Floridia et al. |
| 2007/0262116 A1 | 11/2007 | Hueil et al. |
| 2007/0270784 A1 | 11/2007 | Smith et al. |
| 2007/0286892 A1 | 12/2007 | Herzberg et al. |
| 2007/0288044 A1 | 12/2007 | Jinno et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0128469 A1 | 6/2008 | Dalessandro et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |

(56) References Cited

U.S. PATENT DOCUMENTS

| | | |
|---|---|---|
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0020958 A1 | 1/2009 | Soul |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0065605 A1 | 3/2010 | Shelton, VI et al. |
| 2010/0065609 A1 | 3/2010 | Schwemberger |
| 2010/0069942 A1 | 3/2010 | Shelton, IV |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096435 A1 | 4/2010 | Fuchs et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0001036 A1 | 1/2011 | Stallinga et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0282446 A1 | 11/2011 | Schulte et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0079814 A1 | 3/2013 | Hess et al. |
| 2013/0087602 A1 | 4/2013 | Olson et al. |
| 2013/0146642 A1 | 6/2013 | Shelton, IV et al. |
| 2013/0146643 A1 | 6/2013 | Schmid et al. |
| 2013/0172929 A1 | 7/2013 | Hess et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et at |
| 2013/0256368 A1 | 10/2013 | Timm et al. |
| 2013/0256369 A1 | 10/2013 | Schmid et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |

(56) References Cited

U.S. PATENT DOCUMENTS

| | | |
|---|---|---|
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0327809 A1 | 12/2013 | Shelton, IV et al. |
| 2014/0048582 A1 | 2/2014 | Shelton, IV et al. |
| 2014/0175152 A1 | 6/2014 | Hess et al. |
| 2014/0175156 A1 | 6/2014 | Hess et al. |

FOREIGN PATENT DOCUMENTS

| | | |
|---|---|---|
| CA | 2514274 A1 | 1/2006 |
| CN | 1915180 A | 2/2007 |
| DE | 273689 C | 5/1914 |
| DE | 1775926 A | 1/1972 |
| DE | 3210466 A1 | 9/1983 |
| DE | 9412228 U | 9/1994 |
| DE | 19509116 A1 | 9/1996 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |

(56) References Cited

FOREIGN PATENT DOCUMENTS

| | | |
|---|---|---|
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 1402821 B1 | 12/2007 |
| EP | 1872727 A1 | 1/2008 |
| EP | 1671593 B1 | 2/2008 |
| EP | 1897502 A1 | 3/2008 |
| EP | 1330201 B1 | 6/2008 |
| EP | 1702568 B1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 1759640 B1 | 12/2008 |
| EP | 2000102 A2 | 12/2008 |
| EP | 1749486 B1 | 3/2009 |
| EP | 1721576 B1 | 4/2009 |
| EP | 2090256 A2 | 8/2009 |
| EP | 1607050 B1 | 12/2009 |
| EP | 1875870 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1772105 B1 | 5/2014 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 1217159 A | 12/1970 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 6007357 A | 1/1994 |
| JP | 7051273 A | 2/1995 |
| JP | 8033641 A | 2/1996 |
| JP | 8229050 A | 9/1996 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-87272 A | 4/2001 |
| JP | 2001286477 A | 10/2001 |
| JP | 2002143078 A | 5/2002 |
| JP | 2002369820 A | 12/2002 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2006-281405 A | 10/2006 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1333319 A2 | 8/1987 |
| SU | 1377053 A1 | 2/1988 |
| SU | 1561964 A1 | 5/1990 |
| SU | 1722476 A1 | 3/1992 |
| WO | WO 91/15157 A1 | 10/1991 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |

(56) References Cited

FOREIGN PATENT DOCUMENTS

| | | |
|---|---|---|
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |

(56) References Cited

FOREIGN PATENT DOCUMENTS

| WO | WO 2006/115958 A1 | 11/2006 |
|---|---|---|
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

U.S. Appl. No. 12/038,939, filed Feb. 28, 2008.
U.S. Appl. No. 11/652,165, filed Jan. 11, 2007.
U.S. Appl. No. 11/824,446, filed Jun. 29, 2007.
U.S. Appl. No. 11/824,415, filed Jun. 29, 2007.
U.S. Appl. No. 11/824,274, filed Jun. 29, 2007.
U.S. Appl. No. 11/824,275, filed Jun. 29, 2007.
U.S. Appl. No. 11/823,988, filed Jun. 29, 2007.
U.S. Appl. No. 11/824,079, filed Jun. 29, 2007.
U.S. Appl. No. 11/824,524, filed Jun. 29, 2007.
U.S. Appl. No. 11/824,298, filed Jun. 29, 2007.
U.S. Appl. No. 11/824,389, filed Jun. 29, 2007.
U.S. Appl. No. 11/824,252, filed Jun. 29, 2007.
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
U.S. Appl. No. 13/118,194, filed May 27, 2011.
U.S. Appl. No. 12/032,024, filed Feb. 15, 2008.
U.S. Appl. No. 12/031,580, filed Feb. 14, 2008.
U.S. Appl. No. 12/031,368, filed Feb. 14, 2008.
U.S. Appl. No. 12/031,542, filed Feb. 14, 2008.
U.S. Appl. No. 12/031,556, filed Feb. 14, 2008.
U.S. Appl. No. 12/031,573, filed Feb. 14, 2008.
U.S. Appl. No. 13/118,241, filed May 27, 2011.
U.S. Appl. No. 13/118,272, filed May 27, 2011.
U.S. Appl. No. 13/118,263, filed May 27, 2011.
U.S. Appl. No. 13/118,223, filed May 27, 2011.
U.S. Appl. No. 13/118,190, filed May 27, 2011.
U.S. Appl. No. 13/118,278, filed May 27, 2011.
U.S. Appl. No. 13/118,253, filed May 27, 2011.
U.S. Appl. No. 13/118,210, filed May 27, 2011.
U.S. Appl. No. 13/118,246, filed May 27, 2011.
International Search Report for PCT/US2007/017586, Jan. 25, 2008 (6 pages).
European Examination Report, Application 08770620.6, dated Jun. 4, 2010 (4 pages).

\* cited by examiner

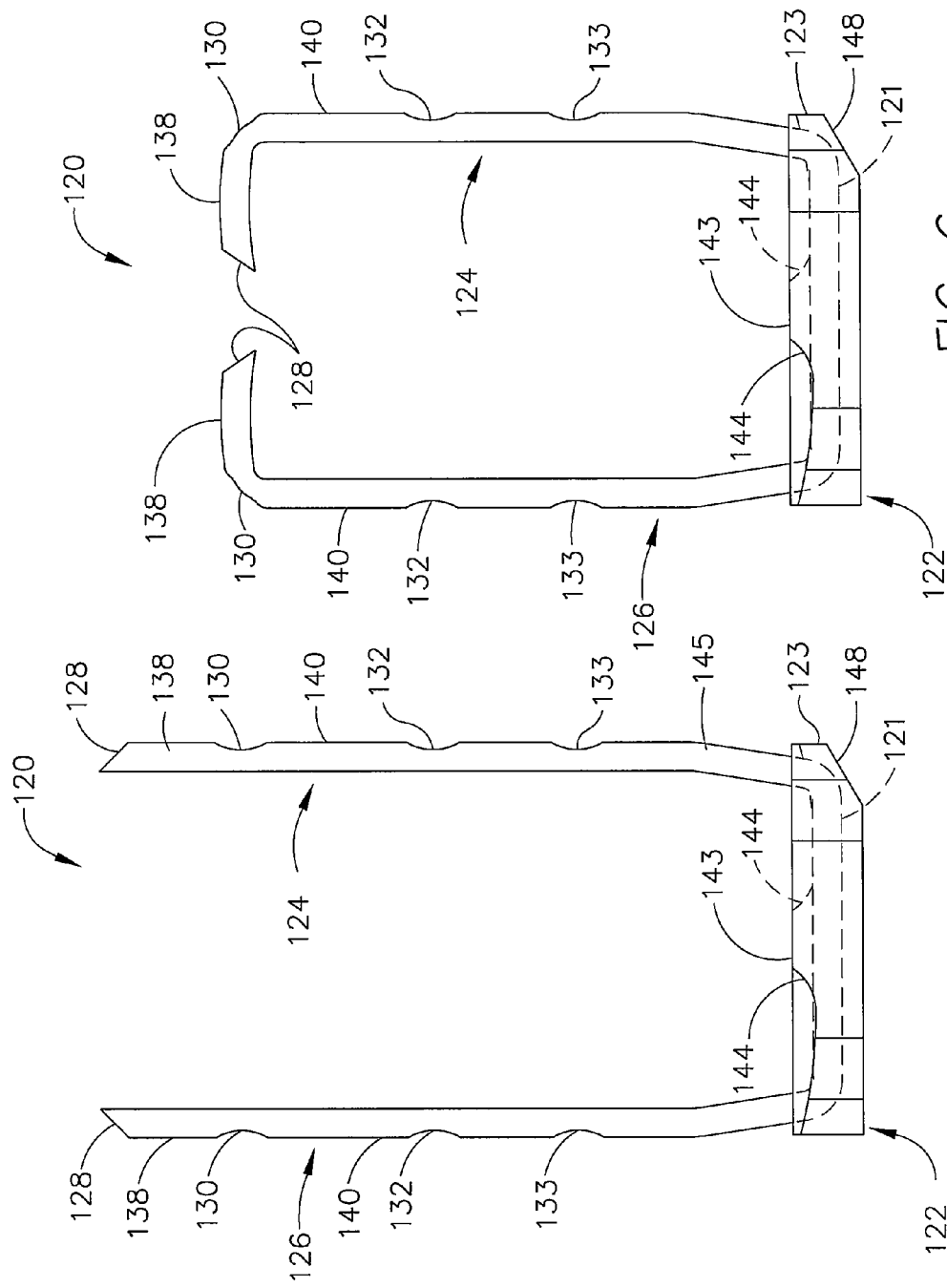

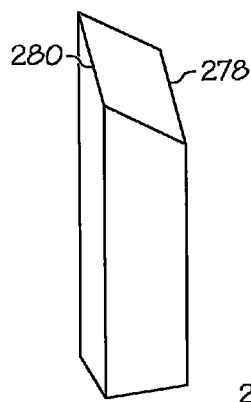 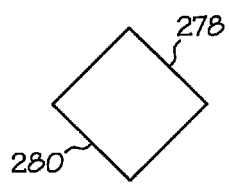 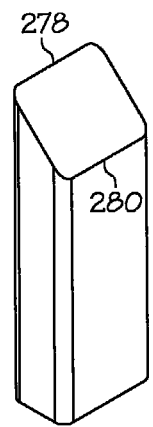 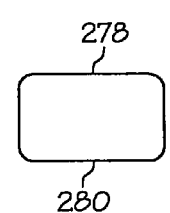
FIG. 42   FIG. 43   FIG. 44   FIG. 45
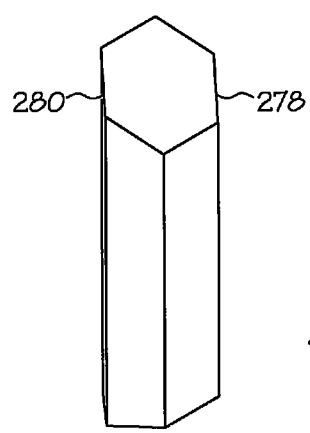 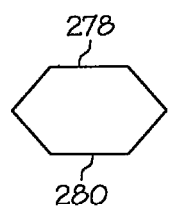 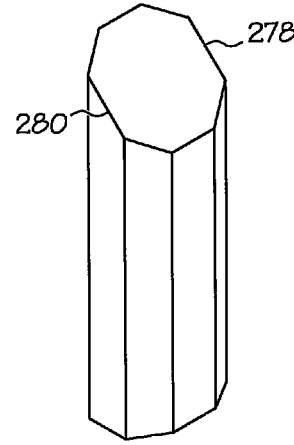 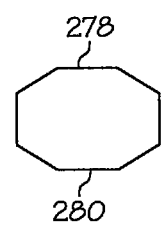
FIG. 46   FIG. 47   FIG. 48   FIG. 49

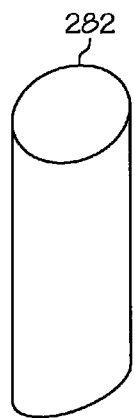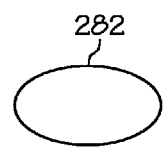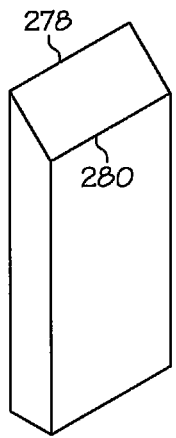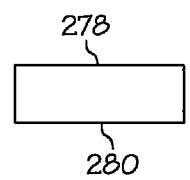
FIG. 50    FIG. 51    FIG. 52    FIG. 53
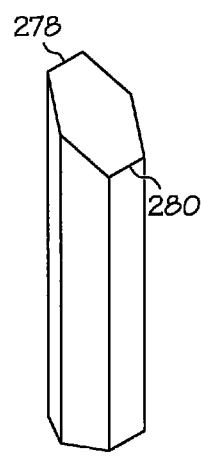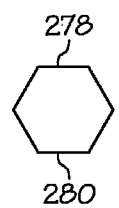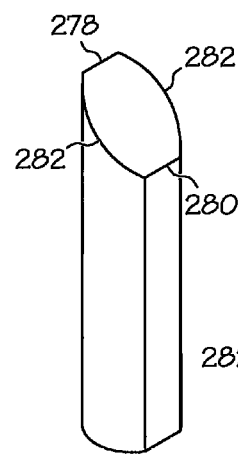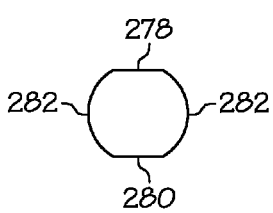
FIG. 54    FIG. 55    FIG. 56    FIG. 57

SURGICAL STAPLE HAVING A SLIDABLE CROWN

The present application is related to the following commonly-owned U.S. patent applications, which are hereby incorporated by reference in their entirety:

(1) U.S. patent application Ser. No. 11/824,389 now U.S. Pat. No. 7,669,747, entitled WASHER FOR USE WITH A SURGICAL STAPLING INSTRUMENT, filed simultaneously herewith;

(2) U.S. patent application Ser. No. 11/824,252 now U.S. Pat. No. 7,735,703, entitled RE-LOADABLE SURGICAL STAPLING INSTRUMENT, filed simultaneously herewith;

(3) U.S. patent application Ser. No. 11/824,363 now U.S. Publication No. 2008/0082115, entitled METHOD OF MANUFACTURING STAPLES, filed simultaneously herewith;

(4) U.S. patent application Ser. No. 11/824,415 now U.S. Pat. No. 7,604,151, entitled SURGICAL STAPLES WITH IMPROVED TISSUE COMPRESSION FEATURES, filed simultaneously herewith;

(5) U.S. patent application Ser. No. 11/824,274 now U.S. Publication No. 2009/0001124, entitled STAPLE CARTRIDGE CAVITY CONFIGURATIONS, filed simultaneously herewith;

(6) U.S. patent application Ser. No. 11/824,275 now U.S. Publication No. 2009/0005808, entitled STAPLE CARTRIDGE CAVITY CONFIGURATION WITH COOPERATIVE SURGICAL STAPLE, filed simultaneously herewith;

(7) U.S. patent application Ser. No. 11/823,988 now U.S. Publication No. 2009/0005809, entitled SURGICAL STAPLE HAVING A SLIDABLE CROWN, filed simultaneously herewith;

(8) U.S. patent application Ser. No. 11/824,079 now U.S. Pat. No. 7,438,209, entitled SURGICAL STAPLING INSTRUMENTS HAVING A RELEASABLE STAPLE-FORMING POCKET, filed simultaneously herewith;

(9) U.S. patent application Ser. No. 11/824,524 now U.S. Publication No. 2009/0001130, entitled SURGICAL PROCEDURE USING A CUTTING AND STAPLING INSTRUMENT HAVING RELEASABLE STAPLE-FORMING POCKETS, filed simultaneously herewith;

(10) U.S. patent application Ser. No. 11/824,299 now U.S. Publication No. 2008/0082125, entitled SURGICAL STAPLE HAVING A DEFORMABLE MEMBER WITH A NON-CIRCULAR CROSS-SECTIONAL GEOMETRY, filed simultaneously herewith;

(11) U.S. patent application Ser. No. 11/824,136 now U.S. Publication No. 2008/0082126, entitled SURGICAL STAPLE HAVING A DEFORMABLE MEMBER WITH A NON-CIRCULAR CROSS-SECTIONAL GEOMETRY, filed simultaneously herewith;

(12) U.S. patent application Ser. No. 11/824,298 now U.S. Pat. No. 7,673,782, entitled SURGICAL STAPLING INSTRUMENT HAVING A RELEASABLE BUTTRESS MATERIAL, filed simultaneously herewith; and

(13) U.S. patent application Ser. No. 11/824,446 now U.S. Publication No. 2009/0001121, entitled SURGICAL STAPLE HAVING AN EXPANDABLE PORTION, filed simultaneously herewith.

BACKGROUND

1. Field of the Invention

The present invention generally relates to surgical instruments and, more particularly, to surgical stapling instruments and staples for use therewith.

2. Description of Related Art

Surgical staplers can be used during a variety of surgical techniques. During at least one surgical technique, a surgical stapler can be inserted through a cannula, or tube, positioned within a small incision in a patient's body. These surgical techniques are referred to as endoscopic and/or laparoscopic surgical techniques and are often preferred over traditional, or open, surgical techniques as they can reduce the recovery time of the patient. Surgical staplers used during such techniques often include an end effector which can be used to achieve a variety of diagnostic and/or therapeutic effects. In various embodiments, such surgical staplers can include an end effector that can incise soft tissue and insert staples into the soft tissue on opposing sides of the incision. In at least one embodiment, the end effector can include a pair of cooperating jaw members that can be passed through the cannula where one of the jaw members can include a staple cartridge and the other jaw member can include an anvil. In at least one such embodiment, the staple cartridge can be configured to deploy at least two rows of staples into the tissue and the anvil can include staple-forming pockets which can be configured to deform the staples as they are deployed.

Some surgical staplers, such as those described in U.S. Pat. No. 5,465,895, entitled SURGICAL STAPLER INSTRUMENT, issued on Nov. 14, 1995, the disclosure of which is hereby incorporated by reference herein, can include an end effector having a cutting member and staple driver, for example, where the cutting member and staple driver can be moved along a linear, curved, and/or curvilinear path within the end effector. Such surgical staplers are often referred to as endocutters and can be utilized during gastric bypass surgical techniques in which the size of a patient's stomach can be reduced, for example. One of the most common gastric bypass surgical techniques is a Roux-en-Y gastric bypass. In such a technique, the stomach can be transected into at least two portions where one of the portions can be formed into a small pouch which can be connected directly to a middle portion of the patient's small intestine, i.e., the jejunum. In various circumstances, the endocutter can be used to cut the stomach along a desired path and deploy staples into the stomach tissue in order to hold the stomach tissue together. As a result of the above-described technique, food passing through the digestive tract can bypass the other transected portion of the stomach and an upper portion of the small intestine, i.e., the duodenum.

Other surgical staplers, such as intra-luminal, or circular, staplers, for example, have been developed to assist a surgeon during a surgical technique known as an anastomosis. An anastomosis is a surgical technique in which a small and/or large intestine is transected, a portion thereof is excised, and the remaining portions are joined together. This technique often requires a surgeon to transect the small intestine, for example, at two locations creating a first end, a second end, and an intermediate portion. Thereafter, the intermediate portion can be removed and the first and second ends can be positioned adjacent to each other. In order to join the first and second ends, the first and second ends can be positioned within an intra-luminal, or circular, stapler such that staples can be deployed into the first and second ends around the perimeter thereof to hold the first and second ends together. Such staplers are disclosed in U.S. Pat. No. 5,104,025, entitled INTRALUMINAL ANASTOMOTIC SURGICAL STAPLER WITH DETACHED ANVIL, issued on Apr. 14, 1992, and U.S. Pat. No. 5,309,927, entitled CIRCULAR STAPLER TISSUE RETENTION SPRING METHOD, issued on May 10, 1994, the disclosures of which are hereby incorporated by reference herein.

SUMMARY OF THE INVENTION

In various forms of the invention, an end effector of a surgical stapler can include an anvil and a staple cartridge where the staple cartridge can be configured to removably store staples therein. In various embodiments, the staple cartridge can include cavities configured to store the staples until they are deployed therefrom by a staple driver which can be configured to traverse the staple cartridge and move the staples toward the anvil. In at least one embodiment, the staples can each include at least one deformable member which can be deformed when it contacts the anvil such that the deformable member can capture soft tissue, for example, between a crown of the staple and the deformable member. In at least one form of the invention, the deformable member can include a non-circular cross-section which can, in various embodiments, dictate the direction and manner in which the deformable member is bent. In at least one embodiment, the non-circular cross-section can include a flat portion which can cause the deformable member to bend in the direction of the flat portion. In various embodiments, the non-circular portion of the cross-section can be configured to abut the soft tissue and apply a compressive force or pressure thereto. In at least one such embodiment, the crown of the surgical staple can be at least partially comprised of a dissolvable or bioabsorbable material such that the crown can dissolve as the soft tissue heals and can, depending on the cross-sectional geometry of the deformable member, reduce the force or pressure applied to the soft tissue by the deformable member.

In at least one form of the invention, a surgical staple can include a deformnable member and a crown, wherein the deformable member can be slid relative to the crown. In at least one embodiment, a staple cartridge can include a cavity and a deck, where the cavity can be configured to receive at least a portion of the deformable member and the crown can be positioned within an opening in the deck. In various embodiments, when soft tissue is captured between the anvil and the staple cartridge, the crown can apply a compressive force or pressure to the soft tissue even before the deformable member is deployed toward the anvil by the staple driver. In at least one such embodiment, as a result, the purchase and/or compressive force, or pressure, between the surgical staple and the soft tissue can be improved. In various embodiments, the crowns of two or more adjacent staples can be connected. In at least one such embodiment, the crowns can apply a uniform pressure to the soft tissue and, in various circumstances, increase the stiffness of the soft tissue after the staples have been deployed therein.

In various forms of the invention, surgical staples can be deployed into soft tissue, for example, in order to reduce, or eliminate, bleeding therefrom especially after the soft tissue has been incised. In various embodiments, the staples can be arranged within a staple cartridge such that they are deployed into the soft tissue in at least two rows, or lines, in order to constrict blood vessels in the soft tissue. In at least one embodiment, a staple cartridge can include first and second staple cavities therein where the first cavity can define a first axis, the second cavity can define a second axis, and the first axis can be transverse to the second axis. In at least one such embodiment, the first and second cavities can extend in directions which are not parallel to each other and, owing to the arrangement of the staples positioned therein, the staples can better constrict the blood vessels in the soft tissue and reduce the flow of blood therethrough. In various forms of the invention, surgical staples can include features which can cooperate with staple cavities in a staple cartridge in order to reduce, or even prevent, the staples from rocking, or tilting, within the staple cavities when the staples are deployed by a staple driver, for example, especially when the staples are oriented in different directions. In at least one such embodiment, the crowns of the staples can include arcuate and/or cylindrical features which can cooperate with arcuate and/or cylindrical features of the staple cavities in order to reduce unwanted relative movement, or rotation, between the staples and the staple cavities.

In various forms of the invention, a surgical staple can include features which can further reduce bleeding from the soft tissue, for example. In at least one embodiment, the staple can include at least one deformable member which can puncture a hole in the soft tissue as it is inserted therethrough and, in various embodiments, the deformable member can include a material thereon, or can be comprised of a material, which can expand and substantially fill the puncture hole in the soft tissue. In various embodiments, at least a portion of the deformable member can be coated with a hydrophilic material, for example, which can expand when exposed to water, or other fluids in the body, and apply a compression force to the perimeter of the puncture hole. Such a compression force can reduce bleeding from the puncture hole and thereby reduce any potential complications resulting therefrom. In at least one form of the invention, a crown of the surgical staple can include features surrounding, or positioned adjacent to, the deformable members which can compress the soft tissue surrounding the deformable members and increase the compressive force or pressure applied thereto. As a result of the increased compressive force or pressure, the flow of blood from the puncture holes created by the deformable members can be reduced.

In various forms of the invention, a surgical stapler can include an anvil, a staple cartridge, and a buttress material removably retained to the anvil and/or staple cartridge. In various embodiments, the staple cartridge can include at least one staple removably stored therein which can, when deployed, or fired, therefrom, contact the buttress material and remove the buttress material from the anvil and/or staple cartridge. In at least one embodiment, the anvil can include at least one lip and/or groove configured to removably retain the buttress material to the anvil until deformable members extending from the surgical staple, for example, are bent by the anvil and are directed toward and contact the buttress material. In various embodiments, the buttress material can be configured to stiffen the soft tissue and/or at least inhibit the staples from tearing the soft tissue. In at least one form of the invention, the anvil of the surgical stapler can include releasable pocket elements that can capture the ends of the deployed, or fired, staples. In various embodiments, the pocket elements can be released from the anvil such that the pocket elements remain with the staples and the stapled tissue after the stapler has been fired. When deployed, the ends of the staples may be turned, or bent, by the pocket elements in the anvil and, thereafter, the ends of the staples may contact a staple-end retaining surface of the pocket element that prevents the ends of the staples from re-puncturing or otherwise re-penetrating the soft tissue. In at least one embodiment, the forces created during the stapling and/or cutting actions of the stapler can overcome a pressure-fit force retaining the pocket elements in the anvil such that the pocket elements are released upon firing. The releasable pocket elements may be made from the same material as the crowns of the staples which can be comprised of, for example, a bioabsorbable material and/or a non-bioabsorbable material.

In yet another general aspect, various forms of the present invention are directed to surgical procedures, such as Roux-en-Y gastric bypass procedures or other procedures, using staples and stapling devices described herein. In particular, various surgical procedures can be performed where a band is placed around soft tissue, for example, that has been incised and stapled. In such techniques, staples and/or stapling devices can be used where the staple ends are not exposed after being inserted into the soft tissue such that the staple ends do not snag or otherwise damage the band which can, in various circumstances, irritate the soft tissue. For example, an instrument having the releasable pocket elements described above may be used to staple the tissue in the area where the band is to be placed. The releasable pocket elements, once released from the anvil, may protect the soft tissue and the band from the staple ends. In various circumstances, a clinician could use two instruments for such a procedure: one not having releasable pocket elements for incisions that are made in areas of the soft tissue where the band will not be placed; and another instrument having releasable pocket elements for incisions that are made in the area of the soft tissue where the band is to be placed. In other embodiments, the clinician could use one instrument and selectively load the instrument with an anvil having the releasable pocket elements for the incisions that are to be made in the area of the soft tissue where the band is to be placed.

In yet another aspect, various forms of the invention are directed to a stapler having a so-called "breakaway" washer inserted into the anvil. In various embodiments, the washer can include a circular outer portion and a circular inner portion. In at least one such embodiment, the outer portion may include a number of staple guide sections that define openings through which the staple ends of surgical staples are driven when the instrument is fired and are thereafter bent, or turned, by the anvil. After being turned, the staple ends may contact and may be retained by the staple guide sections so that the staple ends do not re-penetrate or otherwise re-puncture the stapled tissue. In various embodiments, the surgical instrument may further include a knife which can cut the washer when the surgical instrument is fired so that the inner portion is separated from the outer portion and, as a result, the outer portion can remain with the staples after they have been fired into the soft tissue. As a result, the outer portion of the washer may provide a fixed staple line, which may be particularly beneficial for certain types of anastomotic procedures. In various embodiments, the washer can be made of a non-bioabsorbable material although, in other embodiments, the washer can be made of a bioabsorbable material.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 5 is an elevational view of a surgical staple in an undeformed shape;

FIG. 6 is an elevational view of the staple of FIG. 5 in a first deformed shape;

FIG. 42 is a perspective view of an end portion of another deformable member in accordance with one non-limiting embodiment of the present invention;

FIG. 43 is a cross-sectional view of the deformable member of FIG. 42;

FIG. 44 is a perspective view of an end portion of another deformable member in accordance with one non-limiting embodiment of the present invention;

FIG. 45 is a cross-sectional view of the deformable member of FIG. 44;

FIG. 46 is a perspective view of an end portion of another deformable member in accordance with one non-limiting embodiment of the present invention;

FIG. 47 is a cross-sectional view of the deformable member of FIG. 46;

FIG. 48 is a perspective view of an end portion of another deformable member in accordance with one non-limiting embodiment of the present invention;

FIG. 49 is a cross-sectional view of the deformable member of FIG. 48;

FIG. 50 is a perspective view of an end portion of another deformable member in accordance with one non-limiting embodiment of the present invention;

FIG. 51 is a cross-sectional view of the deformable member of FIG. 50;

FIG. 52 is a perspective view of an end portion of another deformable member in accordance with one non-limiting embodiment of the present invention;

FIG. 53 is a cross-sectional view of the deformable member of FIG. 52;

FIG. 54 is a perspective view of an end portion of another deformable member in accordance with one non-limiting embodiment of the present invention;

FIG. 55 is a cross-sectional view of the deformable member of FIG. 54;

FIG. 56 is a perspective view of an end portion of another deformable member in accordance with one non-limiting embodiment of the present invention;

FIG. 57 is a cross-sectional view of the deformable member of FIG. 56;

FIG. 122 is a perspective view of portions of an anvil, a staple cartridge, and a buttress material removably retained to the anvil in accordance with one non-limiting embodiment of the present invention;

FIG. 123 is a cross-sectional view of the anvil and the buttress material of FIG. 122;

FIG. 124 is a cross-sectional view of an anvil and a buttress material in accordance with one alternate non-limiting embodiment of the present invention;

FIG. 125 is a cross-sectional view of the anvil, staple cartridge and buttress material of the embodiment of FIG. 122 positioned relative to soft tissue and surgical staples in an undeployed position;

FIG. 126 is an additional cross-sectional view of the embodiment of FIG. 125 illustrating the staples in a deployed position;

FIG. 127 is an additional cross-sectional view of the embodiment of FIG. 125 illustrating the anvil in an open position;

FIG. 128 is a diagram illustrating a stomach and a small intestine after a Roux-en-Y gastric bypass surgical technique has been performed thereon;

FIG. 129 is a flow chart illustrating the steps of a gastric bypass surgical technique in accordance with one non-limiting embodiment of the present invention;

FIG. 130 is a cross-sectional view of an anvil having portions thereof which can be broken away by a surgical staple in accordance with one non-limiting embodiment of the present invention;

FIG. 131 is an additional view of the embodiment of FIG. 130 illustrating surgical staples in a deployed configuration;

FIG. 132 is a cross-sectional view of an anvil having portions thereof which can be broken away by a surgical staple in accordance with one alternate non-limiting embodiment of the present invention;

FIG. 133 is an additional view of the embodiment of FIG. 120 illustrating surgical staples in a deployed configuration;

Figure 134:
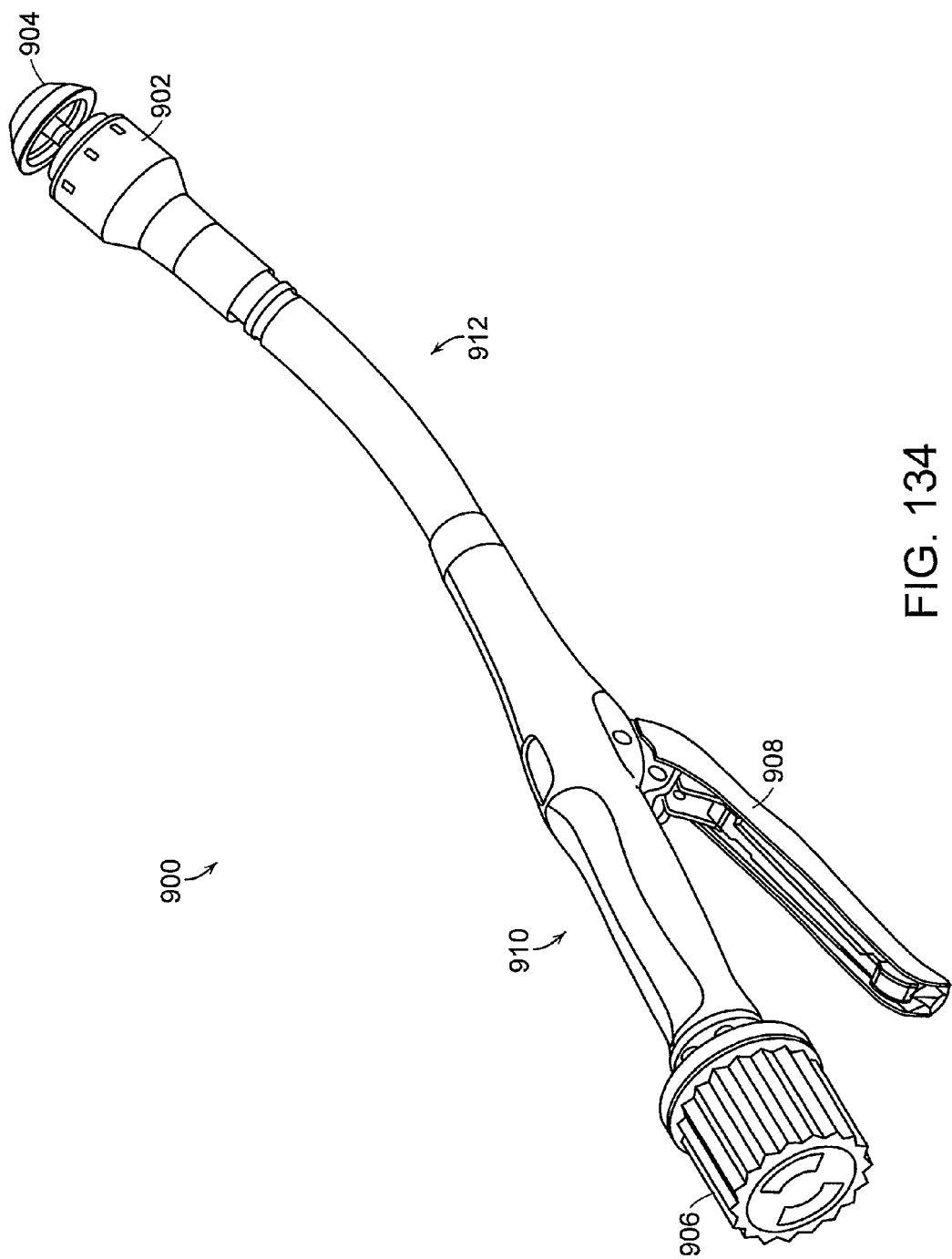
Figure 135:
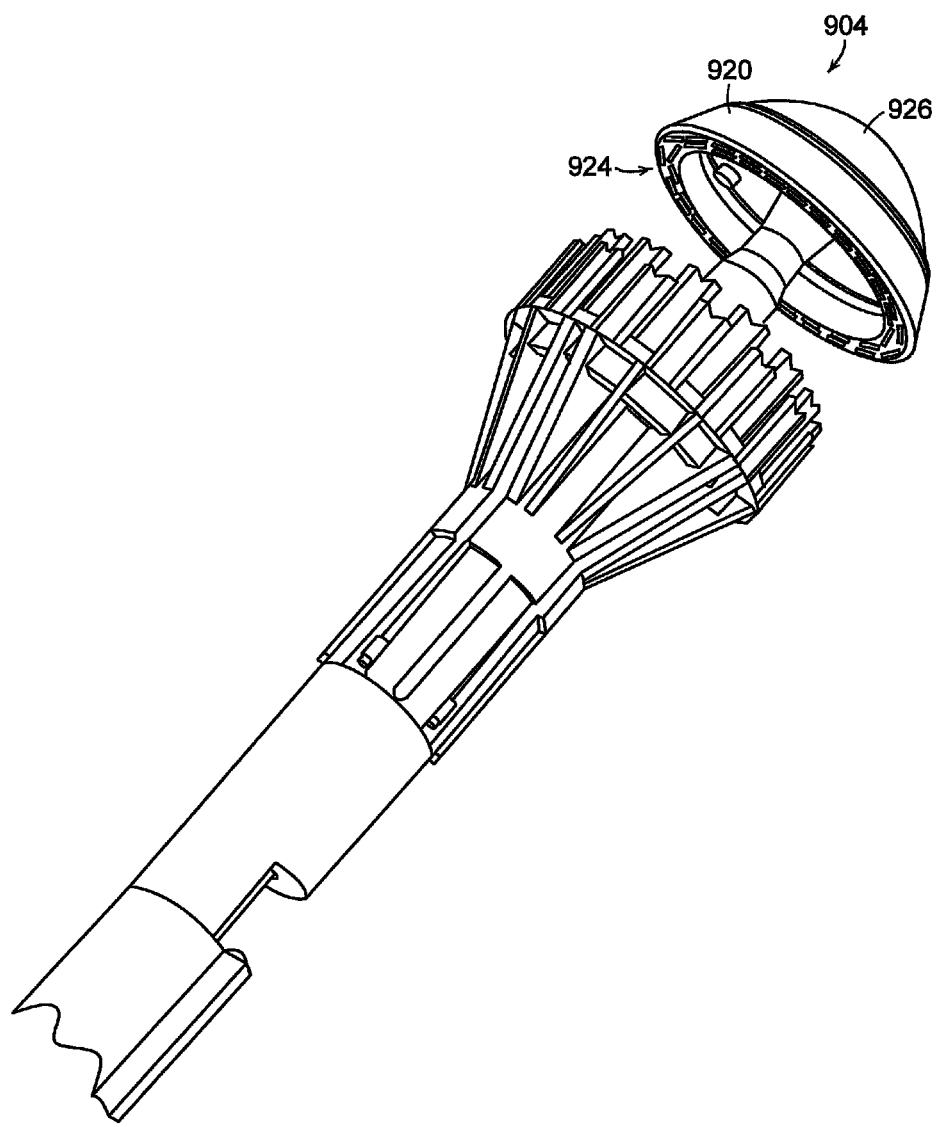
Figure 136:
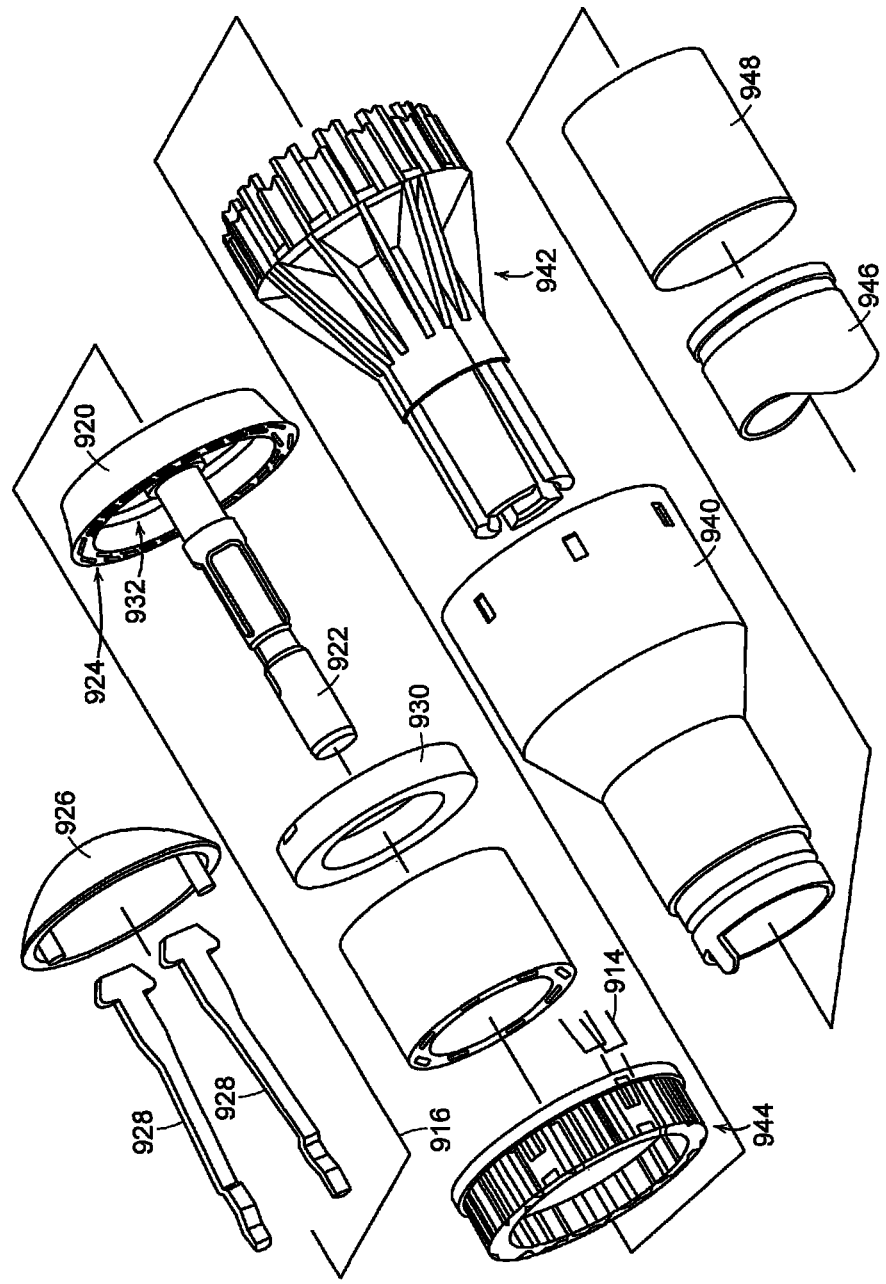
Figure 137:
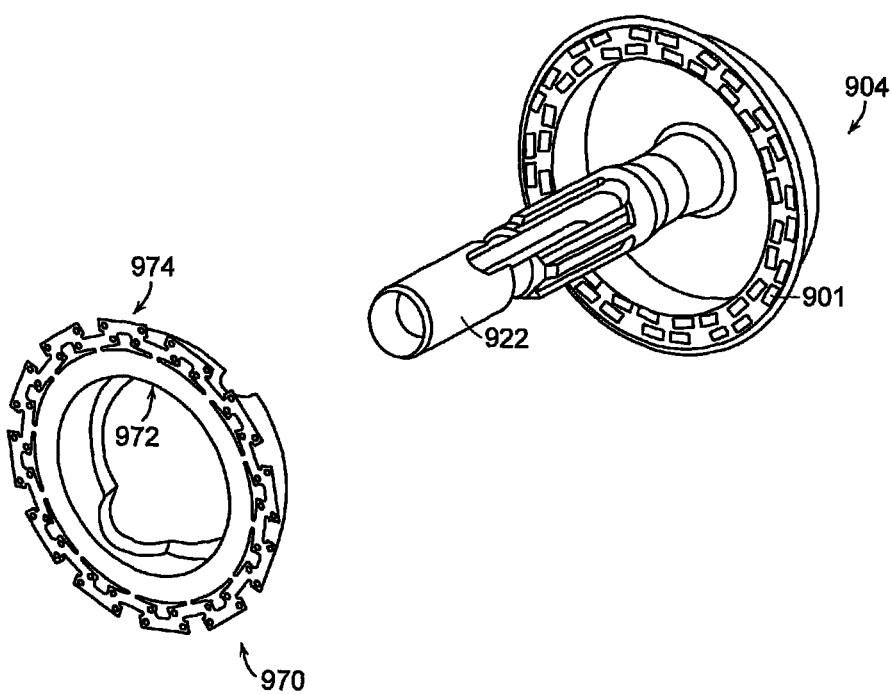
Figure 138:
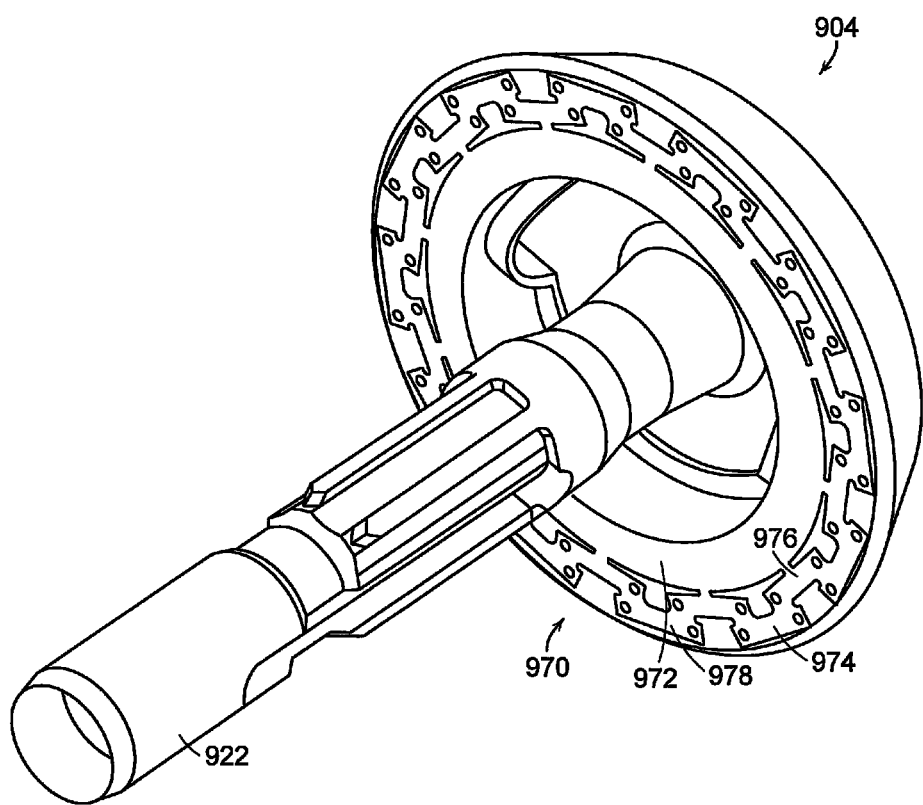
Figure 139:
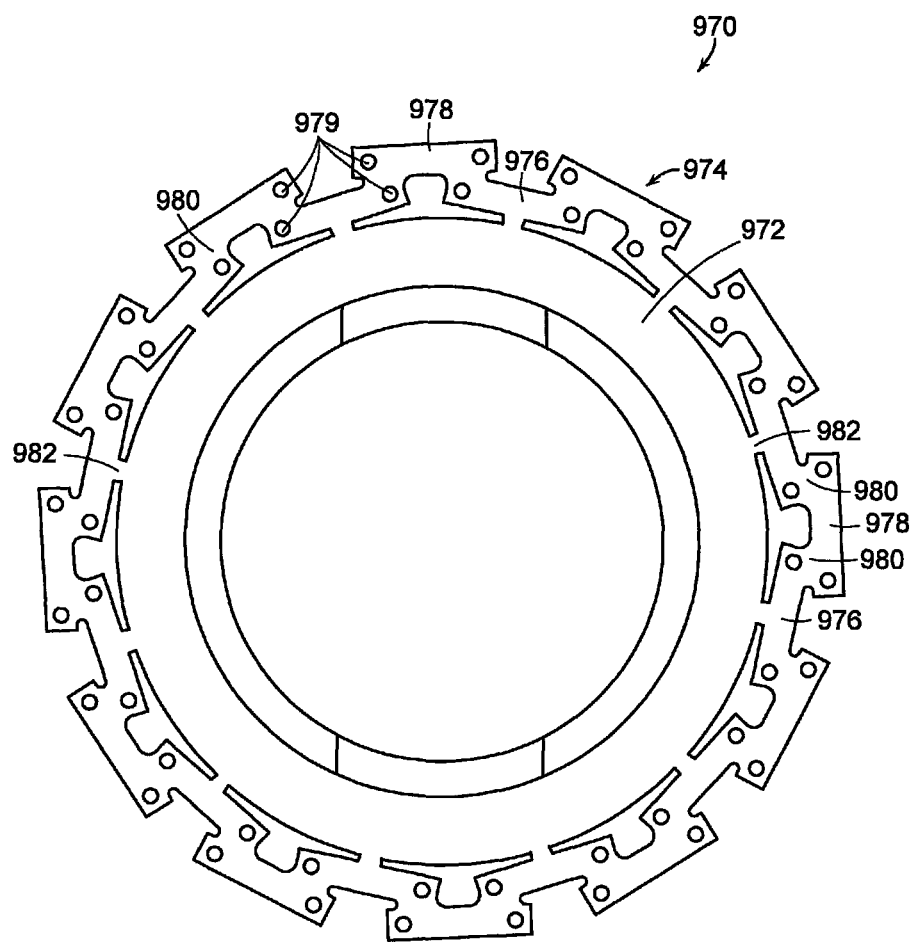
Figure 140:
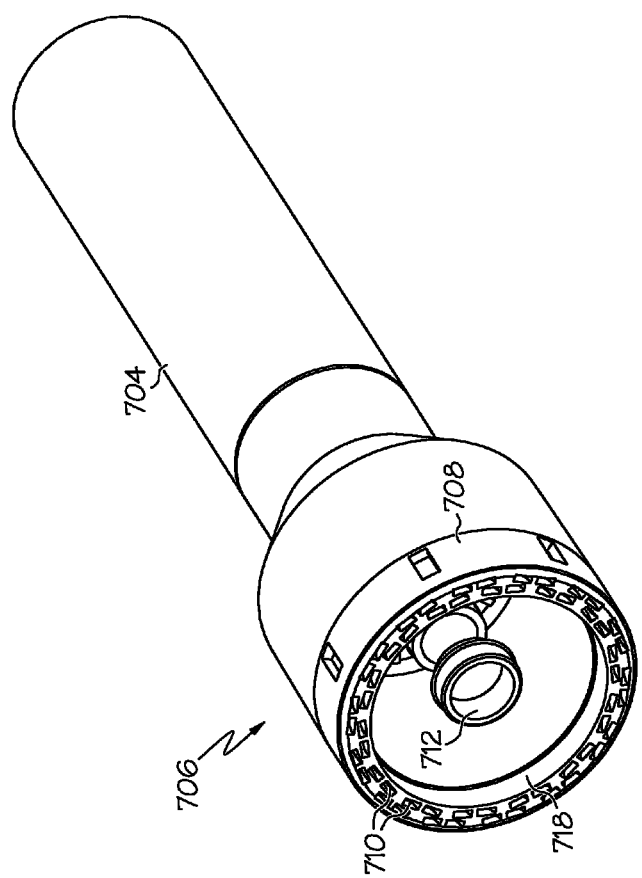
Figure 141:
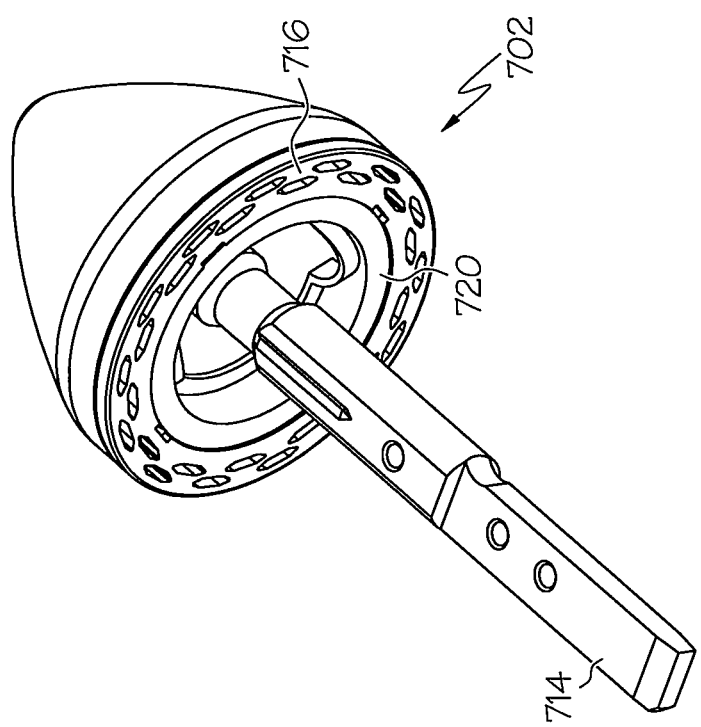
Figure 142:
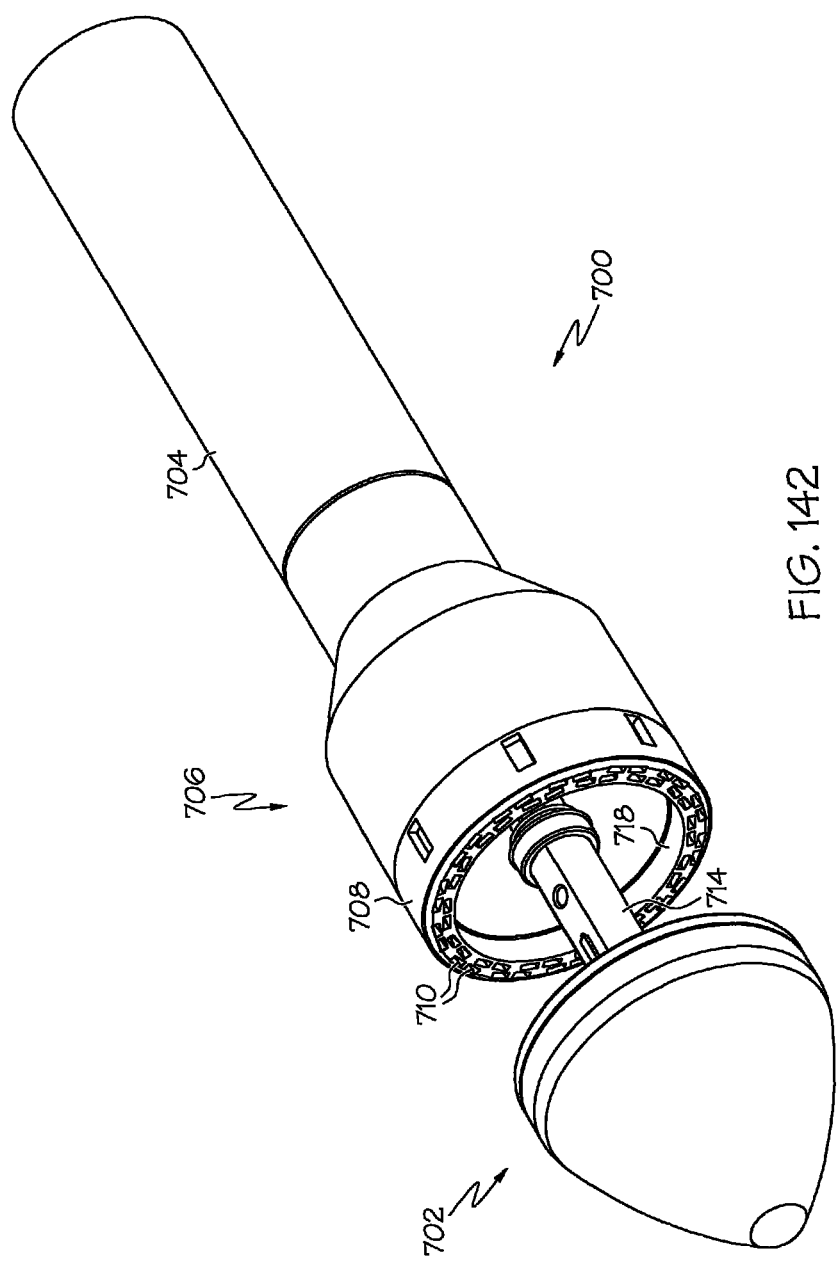
Figure 143:
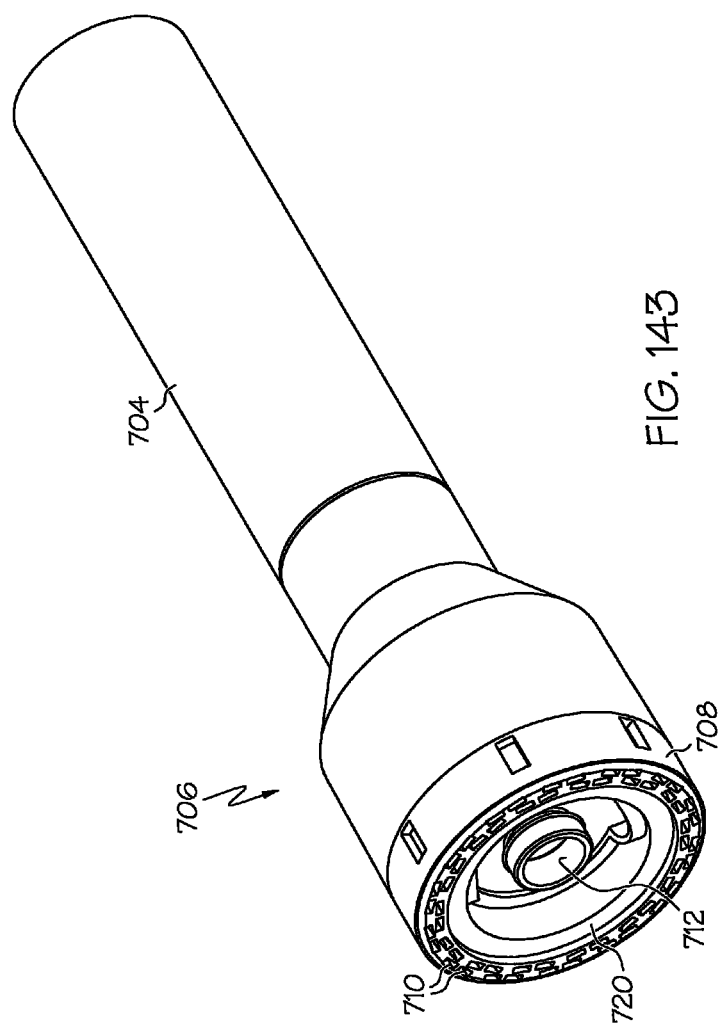
Figure 144:
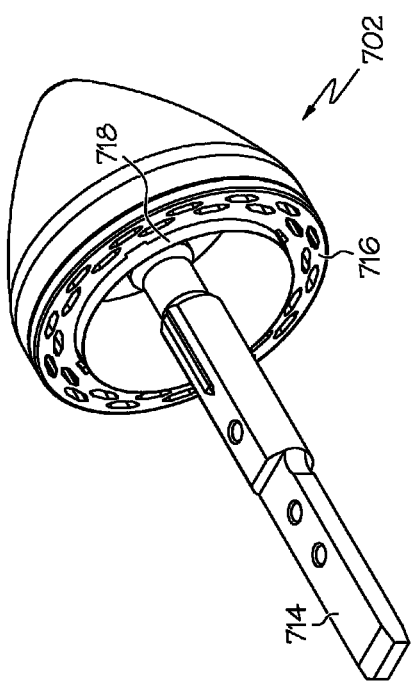
Figure 145:
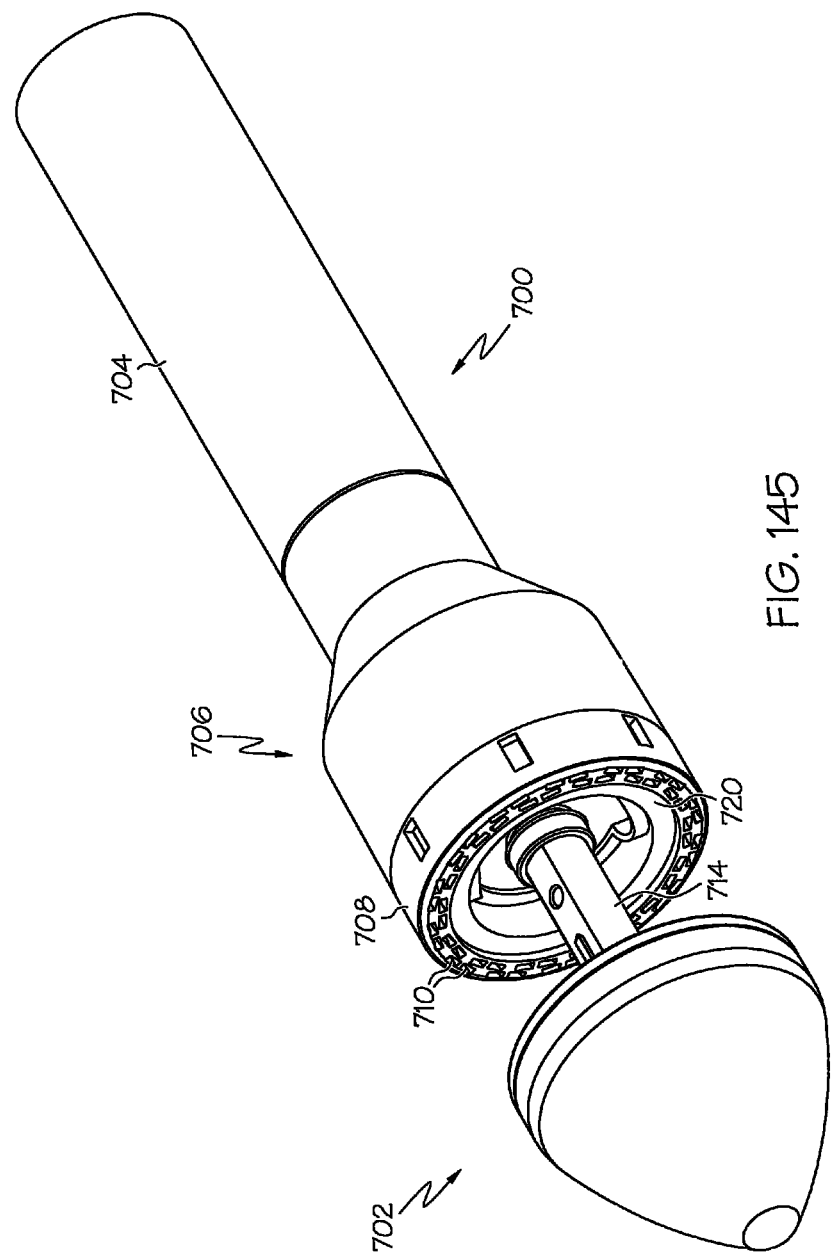
Figure 146:
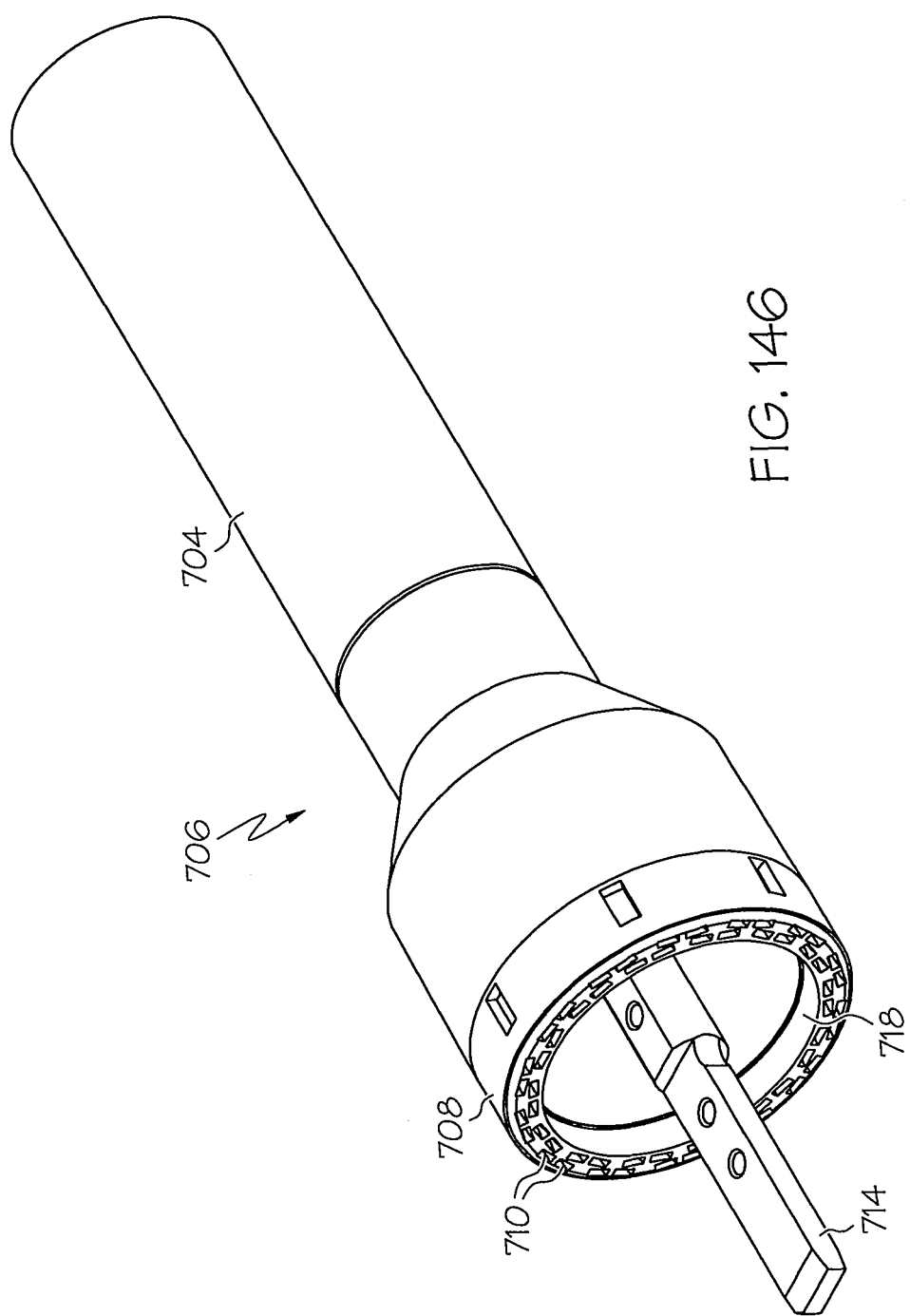
Figure 147:
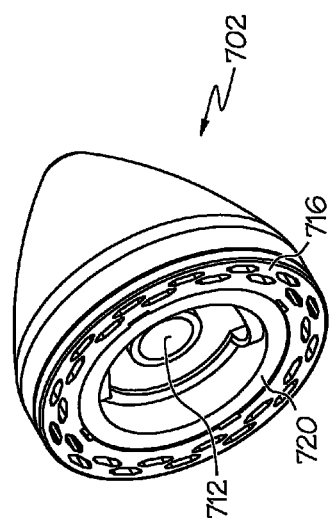
Figure 148:
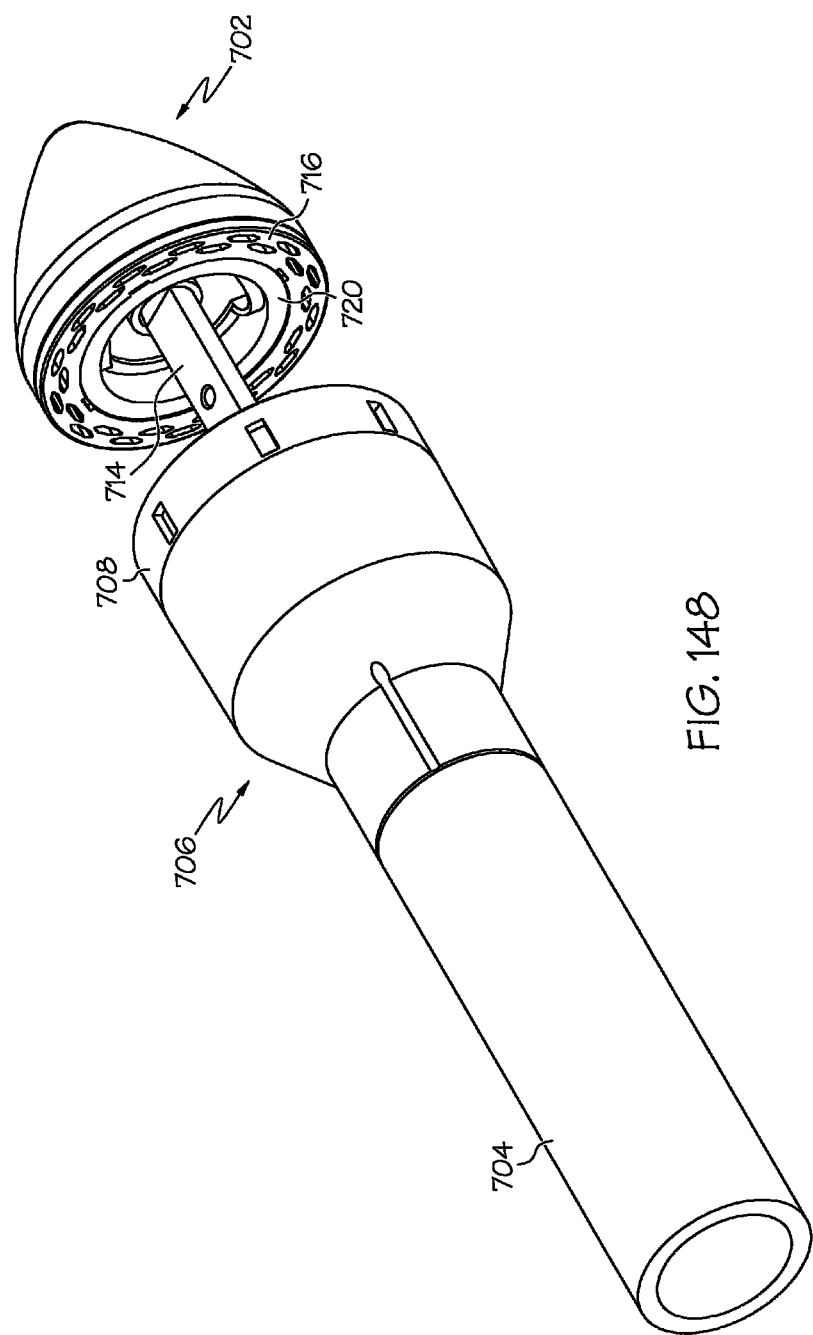

FIG. 134 is a perspective view of a circular surgical stapling instrument in accordance with one non-limiting embodiment of the present invention;

FIG. 135 is a partial perspective view of the stapling instrument of FIG. 134 with portions of the stapling instrument removed;

FIG. 136 is an exploded view of the stapling instrument of FIG. 134;

FIG. 137 is an exploded view of an anvil and a 'breakaway' washer of the surgical instrument of FIG. 134;

FIG. 138 is an assembly view of the anvil and the washer of FIG. 137;

FIG. 139 is a plan view of the assembly of FIG. 138;

FIG. 140 is a perspective view of an anvil member of a circular stapler in accordance with one non-limiting embodiment of the present invention;

FIG. 141 is a perspective view of a staple cartridge mechanism of a circular stapler in accordance with one non-limiting embodiment of the present invention;

FIG. 142 is a perspective view of the staple cartridge mechanism of FIG. 141 assembled to the anvil member of FIG. 140 in accordance with one non-limiting embodiment of the present invention;

FIG. 143 is a perspective view of an anvil member of a circular stapler in accordance with one alternate non-limiting embodiment of the present invention;

FIG. 144 is a perspective view of a staple cartridge mechanism of a circular stapler in accordance with one alternate non-limiting embodiment of the present invention;

FIG. 145 is a perspective view of view of the staple cartridge mechanism of FIG. 143 assembled to the anvil member of FIG. 144 in accordance with one non-limiting embodiment of the present invention;

FIG. 146 is a perspective view of an anvil member of a circular stapler in accordance with another alternate non-limiting embodiment of the present invention;

FIG. 147 is a perspective view of a staple cartridge mechanism of a circular stapler in accordance with another alternate non-limiting embodiment of the present invention; and FIG. 148 is a perspective view of the staple cartridge mechanism of FIG. 146 assembled to the anvil member of FIG. 147 in accordance with one non-limiting embodiment of the present invention.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Figure 1:
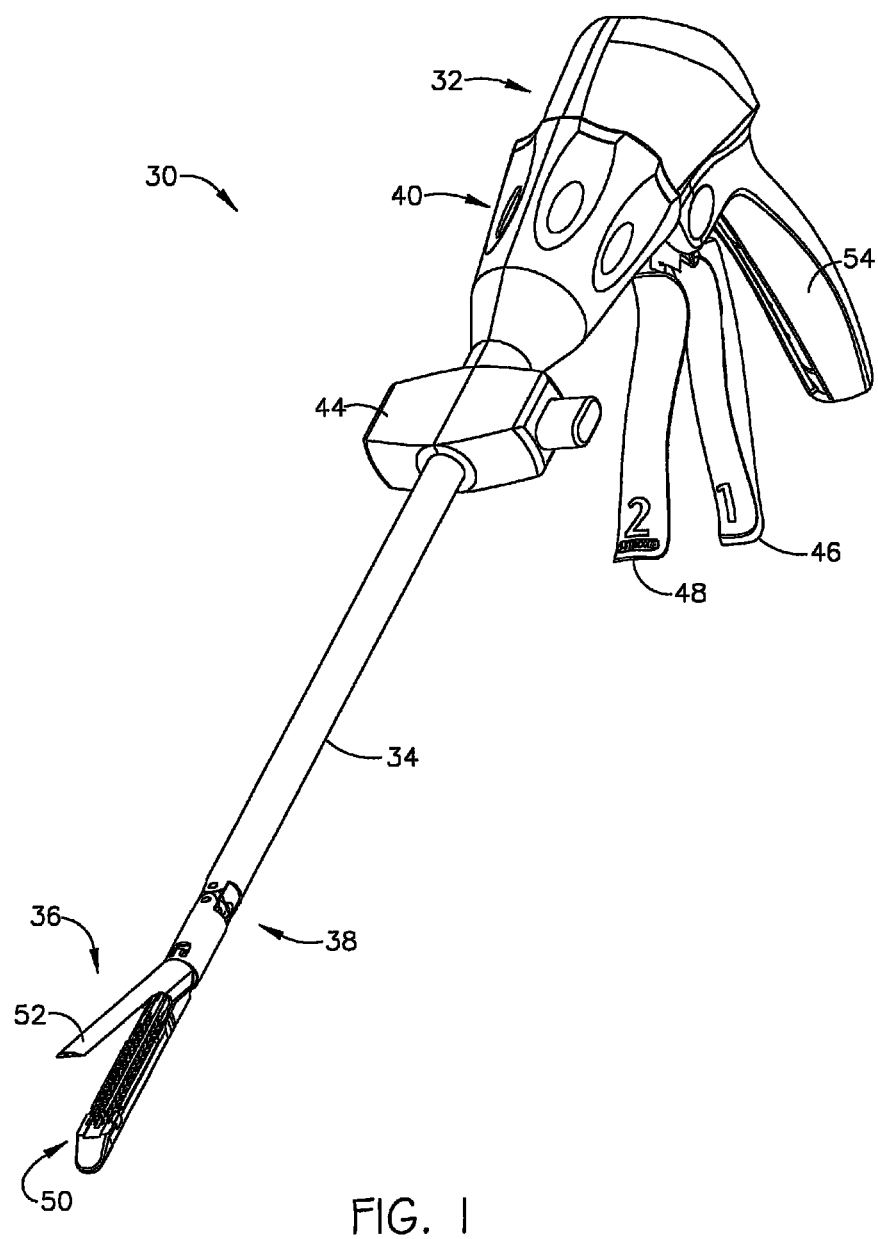
FIG. 1 is a perspective view of a surgical instrument in accordance with one non-limiting embodiment of the present invention.
Figure 2:
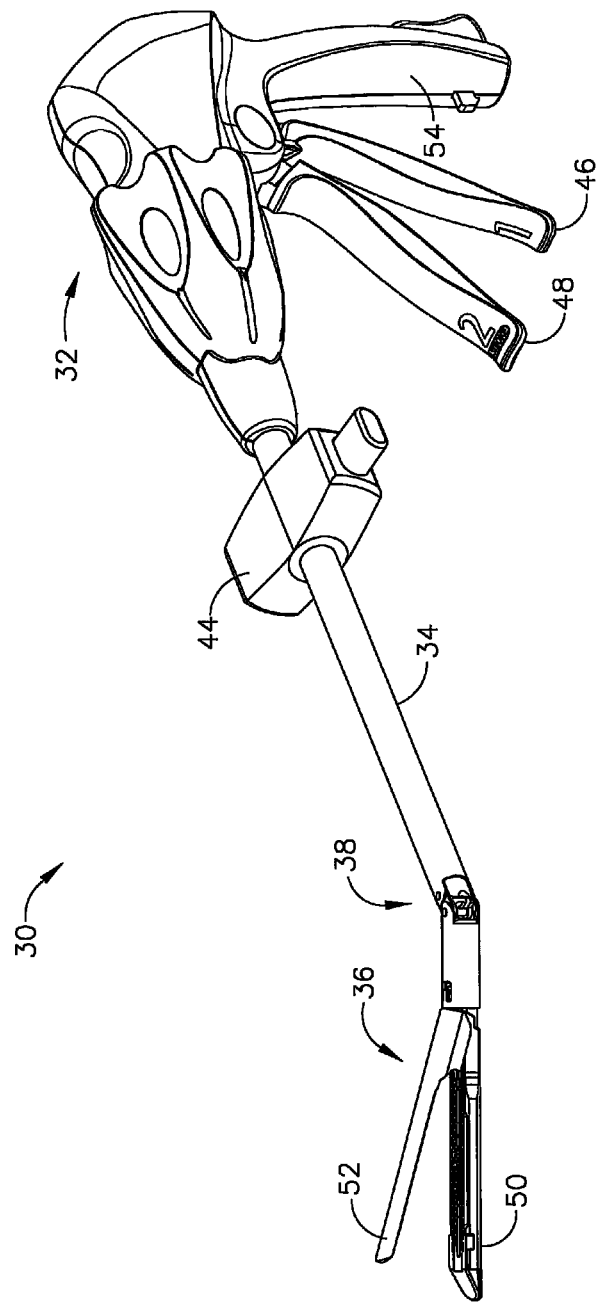
FIG. 2 is a perspective view of the surgical instrument of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention. FIGS. 1 and 2 depict one embodiment of a surgical stapling and severing instrument, i.e., endocutter 30, which is capable of practicing the unique benefits of the present invention. It should be recognized, however, that the unique and novel aspects of the present invention may be advantageously employed in connection with a variety of other staplers and stapling instruments without departing from the spirit and scope of the present invention. Accordingly, the scope of protection afforded to the various embodiments of the present invention should not be limited to use only with the specific types of surgical stapling and severing instruments described herein.

Referring to FIGS. 1 and 2, surgical instrument 30 can comprise handle 32, shaft 34, and articulating end effector 36 pivotally connected to shaft 34 at articulation pivot 38. The placement and orientation of end effector 36 may be facilitated by controls on handle 32, including (a) rotation knob 40 for rotating shaft 34 and end effector 36 about an axis, and (b) articulation control 44 for effecting the rotation, or articulation, of end effector 36 with respect to shaft 34 about articulation pivot 38 as described in greater detail in commonly-owned, co-pending U.S. patent application Ser. No. 11/329,020, entitled SURGICAL INSTRUMENT HAVING AN ARTICULATING END EFFECTOR, which was filed on Jan. 10, 2006, the disclosure of which is incorporated by reference herein. In various embodiments, handle 32 of instrument 30 may include closure trigger 46 and firing trigger 48 for actuating end effector 36 as described in greater detail below. It will be appreciated, however, that instruments having end effectors configured to perform different surgical tasks may have different numbers or types of triggers or other suitable controls for operating end effector 36. Furthermore, it will be appreciated that the terms "proximal" and "distal" are used herein with reference to a clinician gripping handle 32 of instrument 30. Thus, end effector 36 is distal with respect to handle 32.

In the illustrated embodiment, end effector 36 can be configured to clamp, sever, and staple soft tissue, for example. In other embodiments, different types of end effectors may be used such as graspers, cutters, staplers, clip appliers, access devices, drug/gene therapy devices, ultrasound, RF and/or laser devices, for example. End effector 36 can include, among other things, staple channel 50 and a translatable clamping member, such as anvil 52, for example, where staple channel 50 and anvil 52 can be relatively positioned, or spaced, in order to assure that soft tissue clamped in end effector 36 is properly stapled and incised. Handle 32 can include pistol grip 54 towards which closure trigger 46 can be pivotally drawn in order to move anvil 52 toward staple channel 50 and clamp tissue positioned between anvil 52 and channel 50. Stated another way, once the clinician is satisfied with the positioning of end effector 36, the clinician may draw back closure trigger 46 to a position in which anvil 52 is fully closed and trigger 46 is locked into position. Such devices are further described in U.S. patent application Ser. No. 11/343,321, entitled SURGICAL CUTTING AND FASTENING INSTRUMENT WITH CLOSURE TRIGGER LOCKING MECHANISM, which was filed on January 31, the disclosure of which is hereby incorporated by reference herein.

Thereafter, firing trigger 48 may be pivotally drawn toward pistol grip 54 to staple and sever the soft tissue clamped in end effector 36. More particularly, referring to FIG. 3, end effector 36 may further include cutting member or knife 60, sled 62, staple cartridge 64 removably positioned within channel 50, and helical screw shaft 66. Upon an actuation of firing trigger 48, screw shaft 66 can be rotated in order to motivate cutting member 60 and sled 62 relative to channel 50 such that cutting member 60 can incise tissue clamped within end effector 36 and sled 62 can deploy staples removably stored in staple cartridge 64. In various embodiments, sled 62 can include a number of sloped surfaces which can be configured to drive the staples removably stored in staple cartridge 64 into the clamped tissue. In at least one embodiment, anvil 52 can be configured to deform at least a portion of the staples after the staples have been inserted into the tissue. Such instruments are disclosed in U.S. Pat. No. 6,978,921, entitled SURGICAL STAPLING INSTRUMENT INCORPORATING AN E-BEAM FIRING MECHANISM, which issued on Dec. 27, 2005, and U.S. patent application Ser. No. 11/216,562, entitled STAPLE CARTRIDGES FOR FORMING STAPLES HAVING DIFFERING FORMED STAPLE HEIGHTS, which was filed Aug. 31, 2005, the disclosures of which are hereby incorporated by reference herein. In various embodiments, screw shaft 66 can be powered by a hand-powered gear assembly as described in U.S. Pat. No. 5,465,895 mentioned above or by a motor as described in U.S. patent application Ser. No. 11/343,498, entitled MOTOR-DRIVEN SURGICAL CUTTING AND FASTENING INSTRUMENT WITH USER FEEDBACK SYSTEM, which was filed Jan. 31, 2006, the disclosure of which is hereby incorporated by reference herein.

Figure 10:
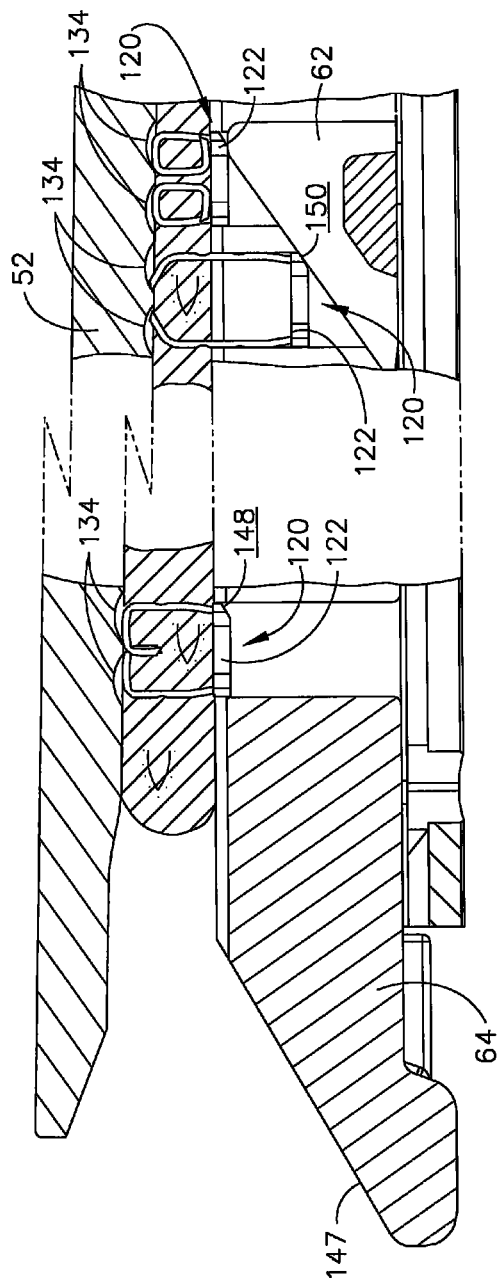
FIG. 10 is a partial cross-sectional view of the surgical stapler of FIG. 1 being used to deploy the surgical staples of FIG. 5 into soft tissue.

In various embodiments, staple cartridge 64 can include staple drivers (not illustrated) positioned therein which can be lifted by sled 62 and can be configured to drive the surgical staples toward anvil 52. In other various embodiments, the surgical staples can be lifted directly by anvil 52. In such embodiments, the crown of the surgical staples can include angled, or beveled, surfaces thereon which can cooperate with sled 62 to lift the surgical staples as described above. Such surgical staples are described in greater detail in U.S. patent application Ser. No. 11/529,935, entitled SURGICAL STAPLES HAVING ATTACHED DRIVERS AND STAPLING INSTRUMENTS FOR DEPLOYING THE SAME, which was filed on Sep. 29, 2006, the disclosure of which is hereby incorporated by reference herein. In various embodiments, referring to FIG. 10, sled 62 can be progressed through staple cartridge 64 from the position illustrated in FIG. 10 toward distal end 147 of staple cartridge 64. As sled 62 is moved distally along cartridge 64, sled 62 can engage crowns 122 of staples 120 such that staples 120 are successively lifted by sled 62 toward anvil 52. More particularly, crowns 122 can include beveled surfaces 148 (FIGS. 5 and 6) which can be configured to cooperate with angled surface 150 of sled 62 such that crowns 122 can slide up sled surface 150.

Figure 4:
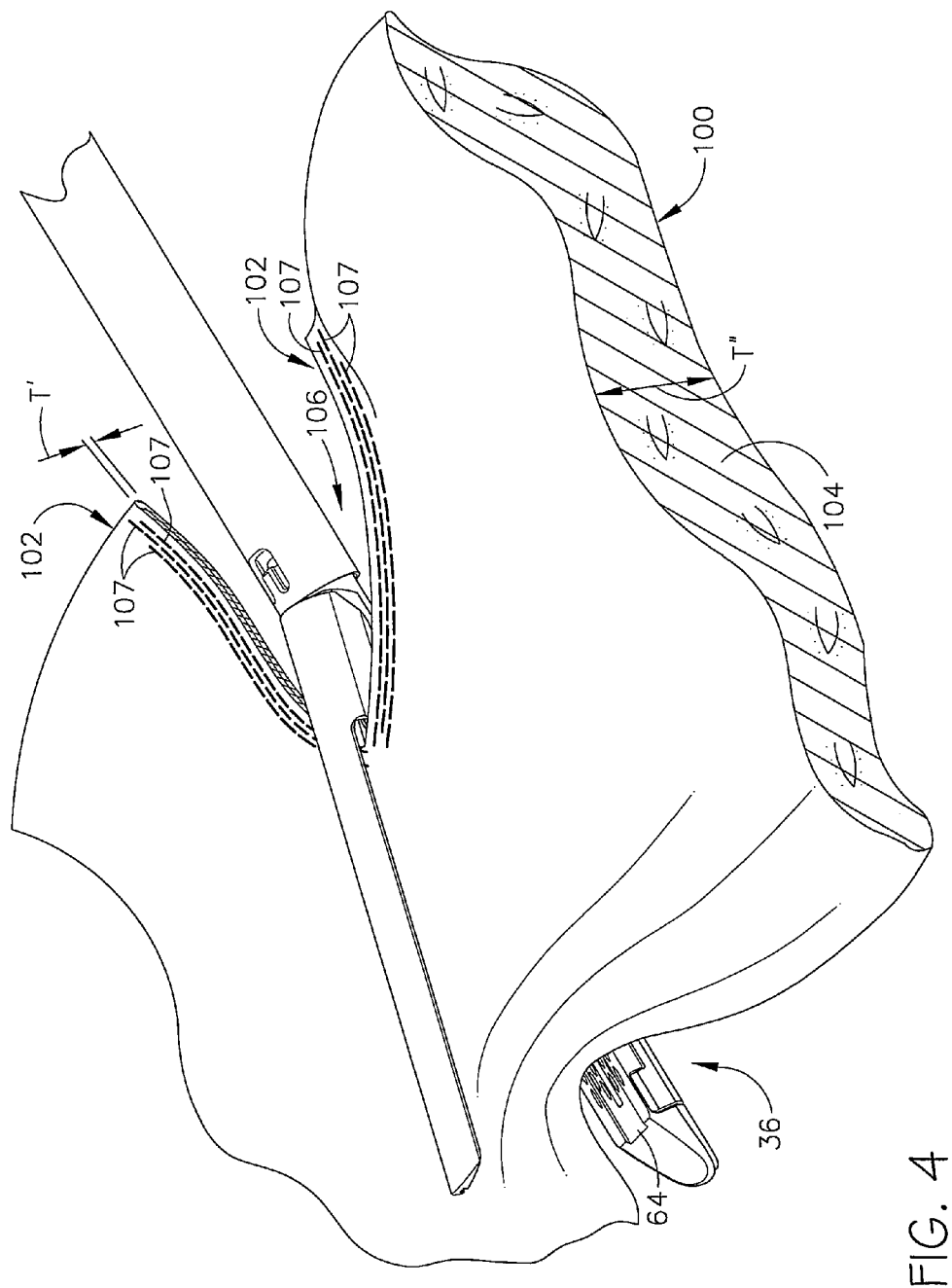
FIG. 4 is a perspective view of the surgical instrument of FIG. 1 being used to incise and staple soft tissue.

FIG. 4 illustrates the cutting and stapling of tissue 100 with any one of the various surgical cutting and stapling instruments described herein. Portion 102 of tissue 100, as illustrated in FIG. 4, has already been cut and stapled along incision 106. Three rows of staples 107 have been inserted by an endocutter 30 into tissue 100 on each side of cut path 106. After the clinician has cut and stapled first portion 102, the instrument would be withdrawn to enable new staple cartridge 64 to be installed. FIG. 4 illustrates the position of end effector 36 prior to commencing the second cutting and stapling process. As can be seen in FIG. 4, portion 102 of tissue 100 that has been stapled has a thickness T' that is less than the thickness T" of other portions 104 of tissue 100.

Figure 10A:
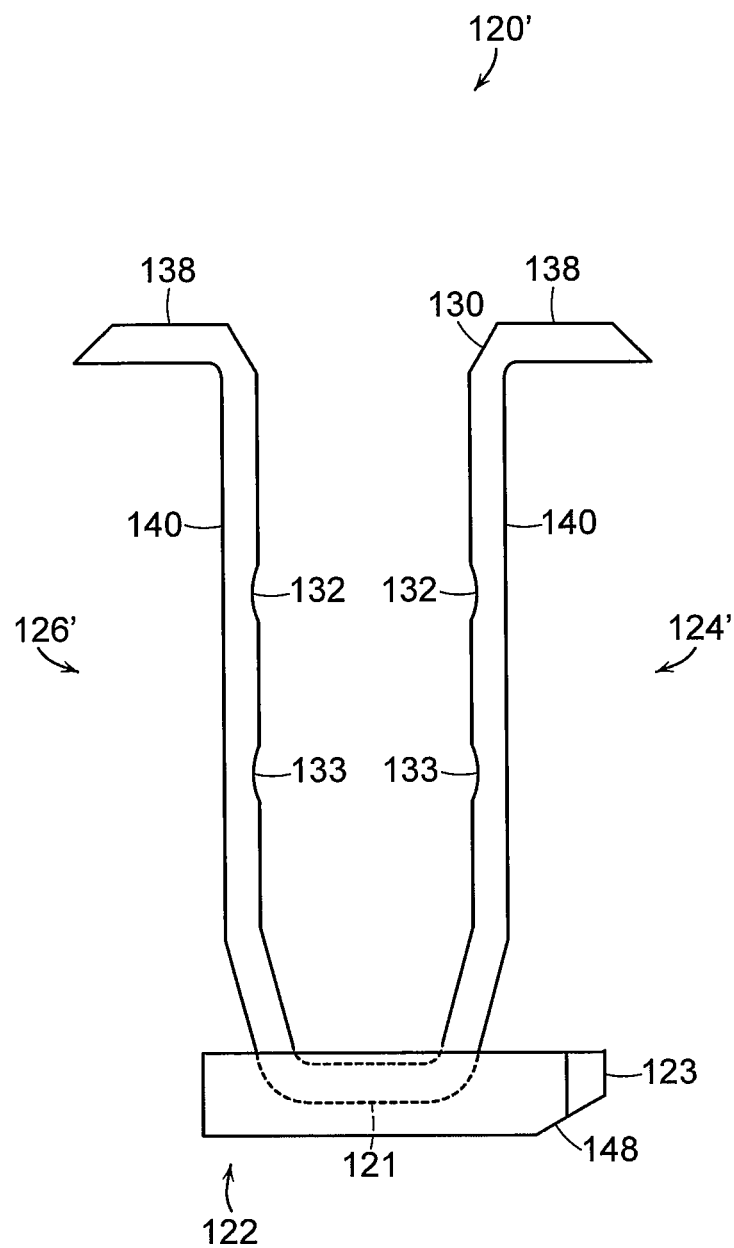
FIG. 10A is an elevational view of a surgical staple in a partially deformed shape.
Figure 11:
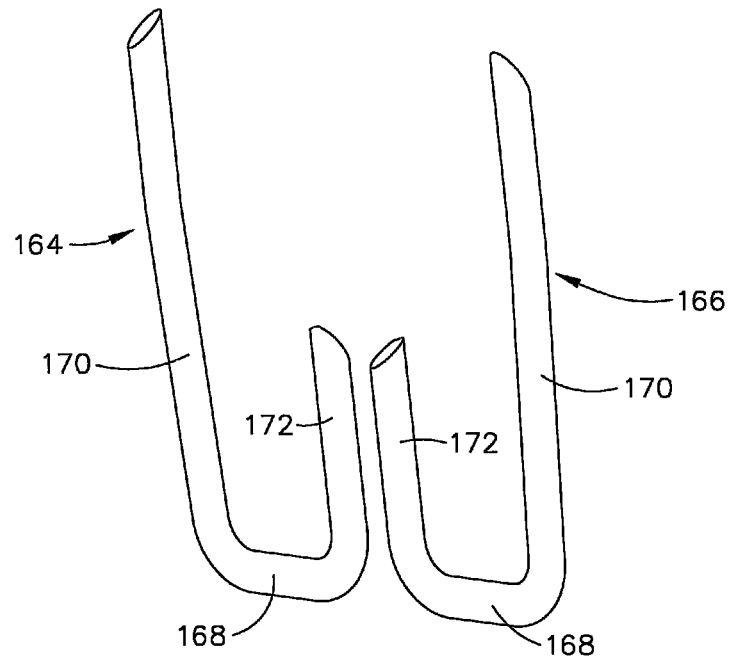
FIG. 11 is a perspective view of first and second deformable members of a surgical staple.

In at least one embodiment, referring to FIGS. 5-9, staple 120 may include crown 122 and deformable legs, or members, 124 and 126 extending therefrom. In various embodiments, the deformable members may be comprised of an elongate wire having a substantially consistent cross-section. In other various embodiments, legs 124 and 126 can include first notches 130, second notches 132, and third notches 133 therein. Referring to FIG. 6 owing to the reduced cross-section of legs 124 and 126 at first notches 130, for example, legs 124 and 126 can be more susceptible to deformation at these locations. In at least one embodiment, when legs 124 and 126 are bent at notches 130, first segments 138 may bend at an approximately 90 degree angle, for example, with respect to second segments 140 of legs 124 and 126. In other embodiments, first segments 138 may be bent at any suitable angle with respect to second segments 140. In use, referring to FIGS. 5 and 10, when ends 128 of legs 124 and 126 contact pockets 134 of anvil 52, legs 124 and 126 may bend inwardly at first notches 130, second notches 132, and third notches 133. In other various embodiments, referring to FIG. 10A, staple 120' can include legs 124' and 126' which can be configured such that they are deformed in an outwardly direction, i.e., away from each other. In at least one such embodiment, the bases of these staples can have a length which is shorter than base 121 such that legs 124' and 126' can contact a portion of anvil pocket 134 and be deformed outwardly. In various embodiments, as a result, these staples can be used with the same anvil which is used to deform staples 120 inwardly as described above. In addition to the above, although not illustrated, any other suitable staples described herein can also include legs which can be configured to be deformed outwardly.

Figure 7:
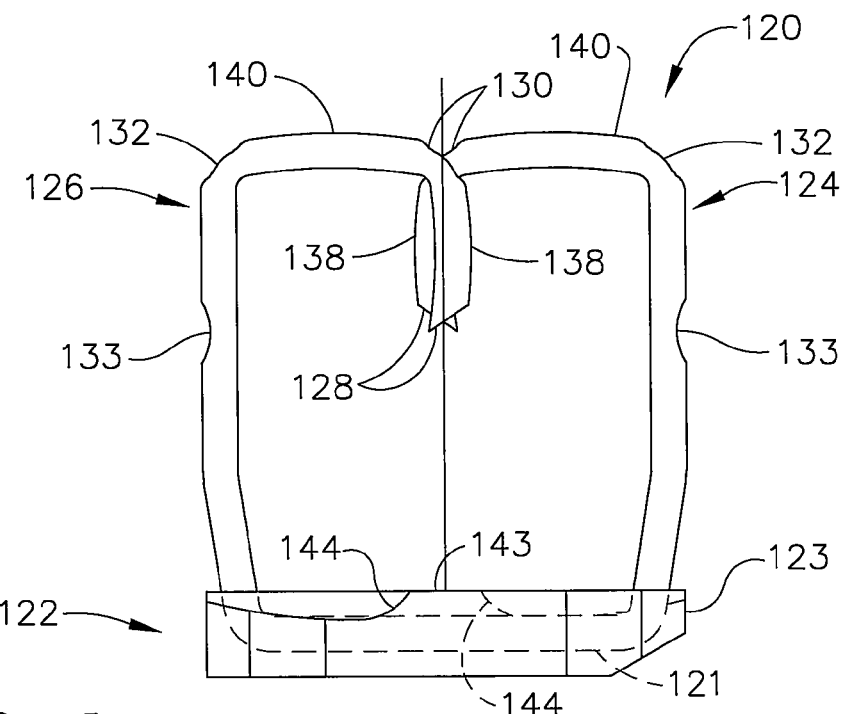
FIG. 7 is an elevational view of the staple of FIG. 5 in a second deformed shape.
Figure 8:
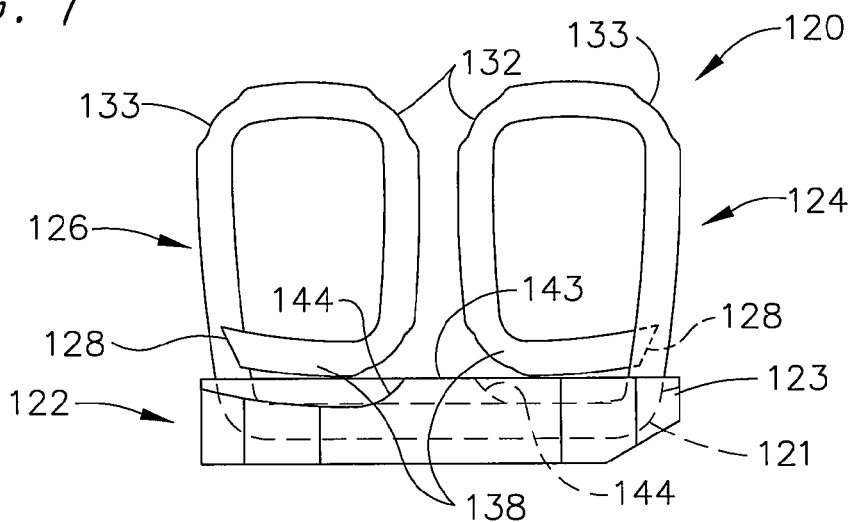
FIG. 8 is an elevational view of the staple of FIG. 5 in a third deformed shape.
Figure 9:
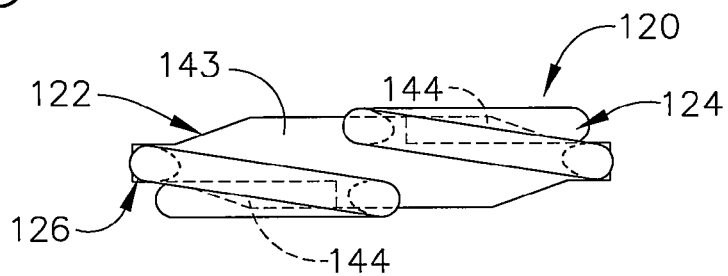
FIG. 9 is a top view of the staple of FIG. 5 in the third deformed shape of FIG. 8.

In various embodiments, referring to FIG. 8, as legs 124 and 126 are being deformed from the shape illustrated in FIG. 7 to the shape illustrated in FIG. 8, ends 128 of deformable members 124 and 126 may contact crown 122. To facilitate the bending of the deformable members, crown 122 may include a forming surface, or anvil, for guiding and/or deforming legs 124 and 126 when they contact crown 122. In order to guide ends 128, anvil 143 of crown 122 can include recesses 144 which can direct ends 128 to move outwardly as illustrated in FIG. 8 or in any other suitable direction. In various embodiments, recesses 144 may not deform legs 124 and 126 significantly, however, in the illustrated embodiment, recesses 144 can be configured to deform legs 124 and 126 at an approximately 90 degree angle. In various embodiments, as a result, anvil 52 of stapler 30 and anvil 143 of crown 122 can cooperate to deform staple 120 into the shape illustrated in FIG. 8, for example, or any other suitable shape.

Referring to FIGS. 5 and 6, base 121 of staple 120 can be embedded in crown 122. In various embodiments, crown 122 can be overmolded onto base 121, such that crown 122 can tightly surround and envelop base 121. In at least one embodiment, material 123 can be formed around a single continuous wire comprising base 121 and deformable members 124 and 126. In other embodiments, deformable members 124 and 126 can be separately embedded in material 123. In either event, in at least one embodiment, crown 122 can include material 123 overmolded onto base 121 where material 123 can be comprised of a plastic material, such as, for example, a dissolvable, biofragmentable, or bioabsorbable plastic material. In embodiments using such materials, the plastic material may include Vicryl or PDS from Ethicon, Inc., for example. As used herein, the terms dissolvable, bioabsorbable, and biofragmentable generally refer to materials that can be at least partially assimilated by the body after being implanted into a patient, for example. In various embodiments, in addition to or in lieu of the above, the plastic material can include a non-dissolvable, non-biofragmentable, or non-bioabsorbable plastic material. In either event, in various other embodiments, crown 122 may be separately manufactured and then assembled to base 121.

Further to the above, in at least one embodiment, the dissolvable, biofragmentable, or bioabsorbable materials can at least partially dissolve during the healing process thereby allowing the tissue compressed within staple 120 to expand and grow. In at least one embodiment, referring to FIGS. 11-15, staple 160 can include crown 162, first deformable member 164, and second deformable member 166, where deformable members 164 and 166 can each include base 168, deformable leg 170, and second leg 172. When staple 160 is initially deployed, deformable members 164 and 166 may apply significant compressive forces to the soft tissue positioned within staple 160 in order to limit bleeding therefrom. As crown 162 deteriorates, however, the gap between deformed members 164 and 166 and crown 162 may increase, thereby relaxing the compressive forces acting on the soft tissue. In some applications, relaxing these compression forces during the healing process may allow the tissue to slowly expand and return to its normal thickness over a period of time. In some embodiments, crown 162 can be coated with a hydrophilic material that initially expands to compress the tissue captured within the staple before dissolving away thereafter. In these embodiments, the hydrophilic material can expand by absorbing water from the surrounding tissue and fluids, for example.

Figure 15:
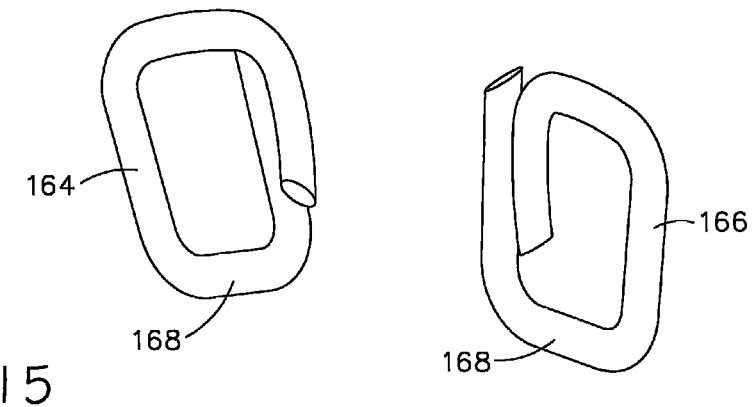
FIG. 15 is a perspective view of the staple of FIG. 12 after the dissolvable material has completely dissolved.
Figure 16:
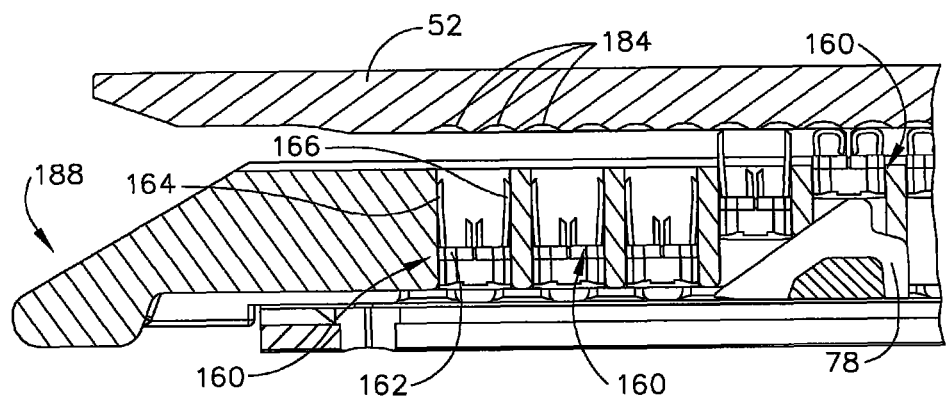
FIG. 16 is a partial cross-sectional view of a surgical stapler being used to deploy the surgical staples of FIG. 12 into soft tissue.
Figure 17:
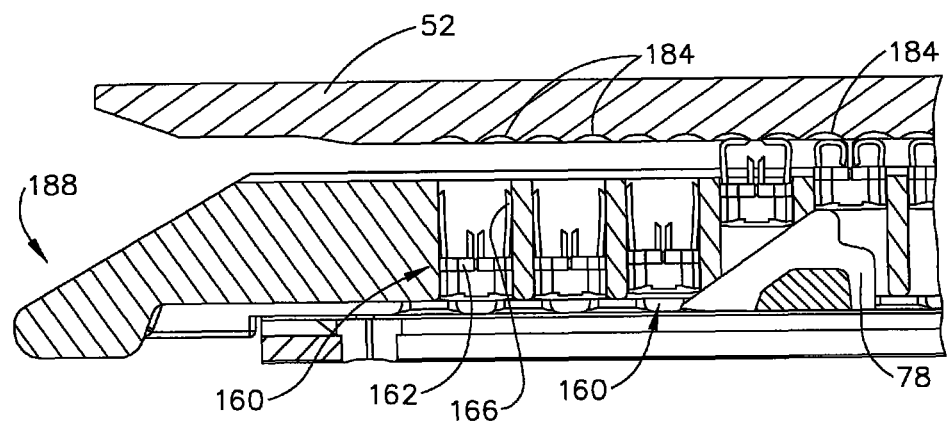
FIG. 17 is an additional partial cross-sectional view of the surgical stapler of FIG. 16.

As a result of the above, when a plurality of staples 160 are inserted into the soft tissue, staples 160 may cause the soft tissue to become stiff and, in various circumstances, the tissue may not be permitted to move and expand during the healing process. However, after crowns 162 of staples 160 have been at least partially dissolved, deformable members 164 and 166 of staples 160 may be able to move relative to each other while still holding the underlying tissue together. More particularly, referring to FIG. 14, the material of crown 162 can deteriorate to the point where first member 164 and second deformable member 166 can become disconnected from each other as illustrated in FIG. 15. Once first member 164 and second member 166 have become disconnected, they can move relative to one another and the soft tissue can become less stiff. In various embodiments, the time required for crown 162 to sufficiently dissolve may depend on the material used and/or the size of crown 162. Polyglatin 910 material, sold under the trade name Vicryl, for example, may dissolve in seven to fourteen days.

In various embodiments, deformable members 164 and 166 can be comprised of a substantially non-dissolvable or non-bioabsorbable material such as, for example, titanium, titanium alloy, or stainless steel. In other embodiments, at least one of deformable members 164 and 166 may be comprised of a bioabsorbable material such as magnesium or iron, for example. In at least one embodiment, the iron is pure iron. In either event, the dissolvable material of members 164 and 166 can be selected such that they dissolve at the same rate as, slower than, or faster than the dissolvable material of crown 162. For example, the material of crown 162 can be selected such that it completely dissolves away while deformable members 164 and 166 are still holding soft tissue together, for example. Further, in various embodiments, the material of first deformable member 164 can be selected such that it dissolves faster than the material of second deformable member 166. Accordingly, deformable members of 164 and 166 in these embodiments may allow for a staggered release of the tissue. Further to the above, in various embodiments, at least two adjacent staples 160 can be connected by a bridge before and/or after the staples 160 have been deployed into the tissue. In these embodiments, a first staple 160 can be comprised of bioabsorbable materials that dissolve away at a faster rate than the materials of a second staple 160 attached thereto. Similarly, the bridge connecting the staples 160 can be comprised of materials that dissolve away at the same rate, and/or a different rate, than the first and second staples 160. In these embodiments, the first staples 160 can dissolve away before the second staples 160 allowing for a staggered release of the tissue similar to the above.

Figure 12:
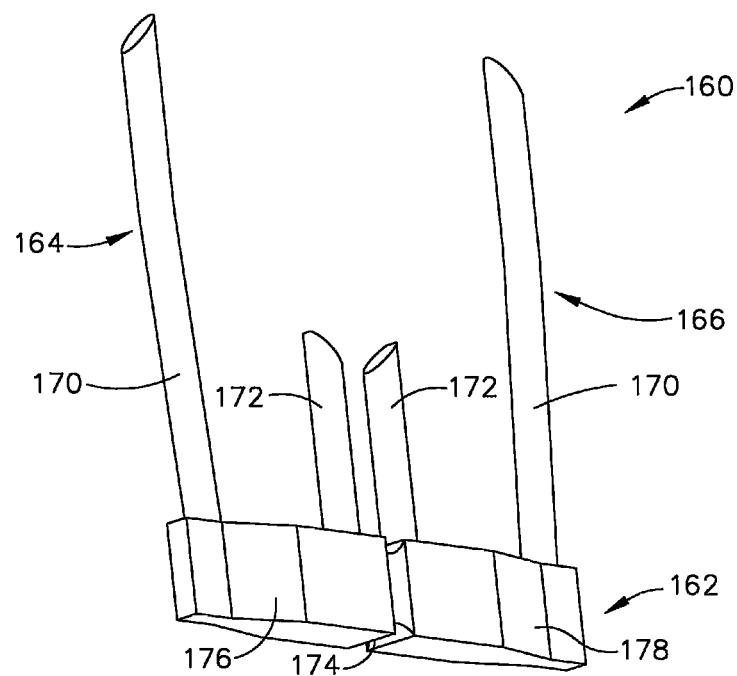
FIG. 12 is a perspective view of a dissolvable, or bioabsorbable, material overmolded onto the deformable members of FIG. 12.
Figure 13:
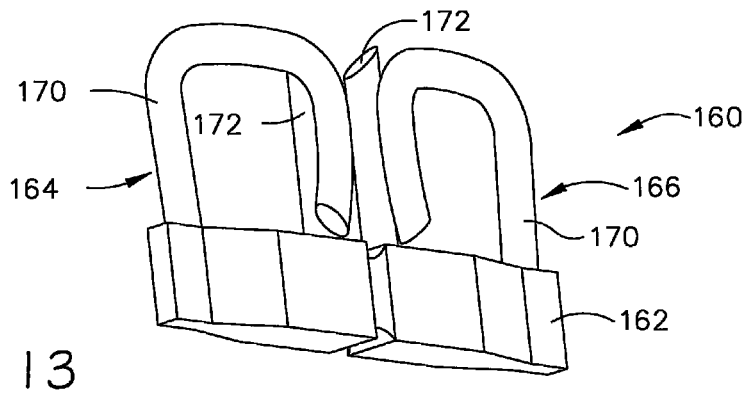
FIG. 13 is a perspective view of the staple of FIG. 12 in a deformed shape.
Figure 14:
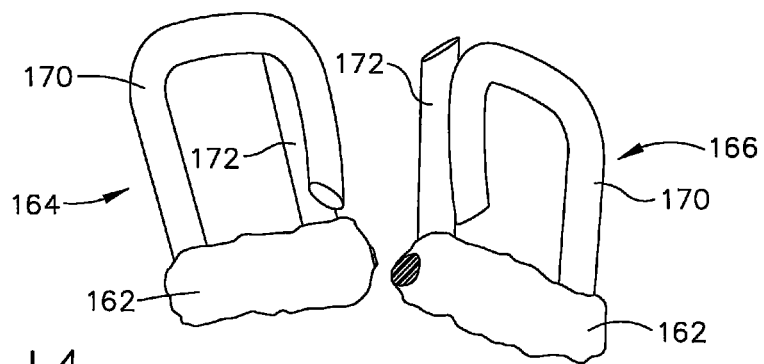
FIG. 14 is a perspective view of the staple of FIG. 12 where a portion of the dissolvable material has been dissolved and the first and second deformable members have moved relative to one another.

In various embodiments, referring to FIG. 12, crown 162 can include reduced cross-section 174 intermediate portions 176 and 178. In use, intermediate section 174, as it has a smaller cross-section than portions 176 and 178, may completely dissolve away before sections 176 and 178 thereby allowing first member 164 to become unconnected from second member 166 before the entirety of crown 162 has dissolved (FIG. 15). In at least one embodiment, the cross-sections of sections 174, 176, and 178 can be selected such that deformable members 164 and 166 become unconnected at a desired stage in the healing process. In other embodiments, crown 162 can include score marks (not shown), which may reduce the thickness of crown 162 in the scored areas. In at least one embodiment, crown 122 of staple 120 (FIGS. 5-9) and/or crown 162 of staple 160 (FIGS. 11-15) may comprise at least one therapeutic drug. In these embodiments, as the dissolvable material deteriorates, the therapeutic drug can be absorbed by tissue surrounding the staple. In some embodiments, the drug is dispersed throughout the dissolvable material such that the drug is steadily released during the healing process, however, in other embodiments, the therapeutic drug may be unevenly dispersed throughout the dissolvable material, or layered within and/or on the material, to provide an increased dosage of the drug at a particular stage in the healing process.

Figure 18:
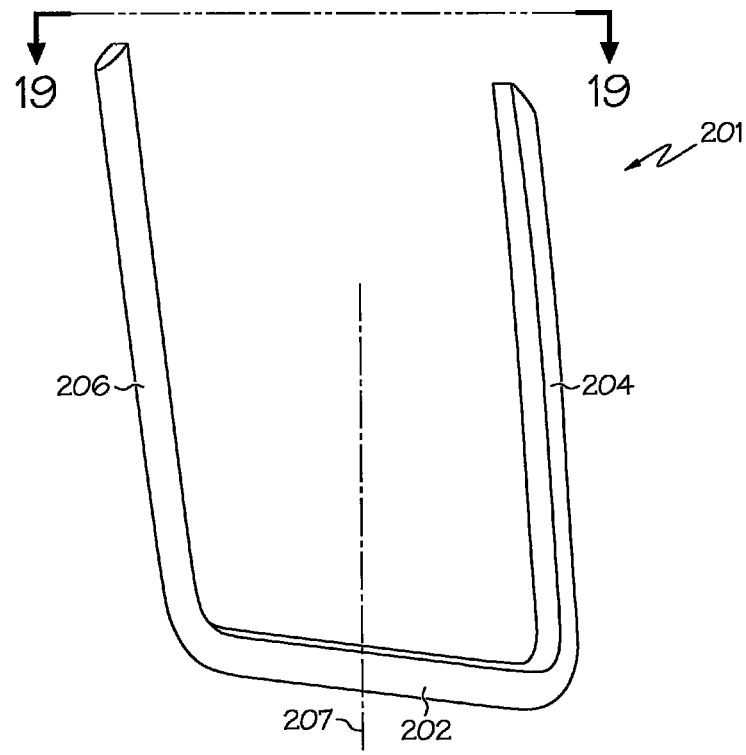
FIG. 18 is a perspective view of a deformable member of a staple in accordance with one non-limiting embodiment of the present invention.
Figure 19:
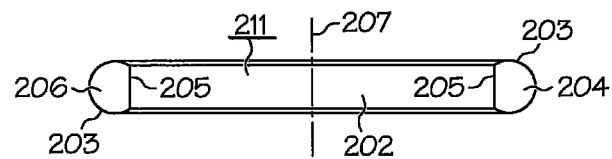
FIG. 19 is a top view of the deformable member of FIG. 18.
Figure 20:
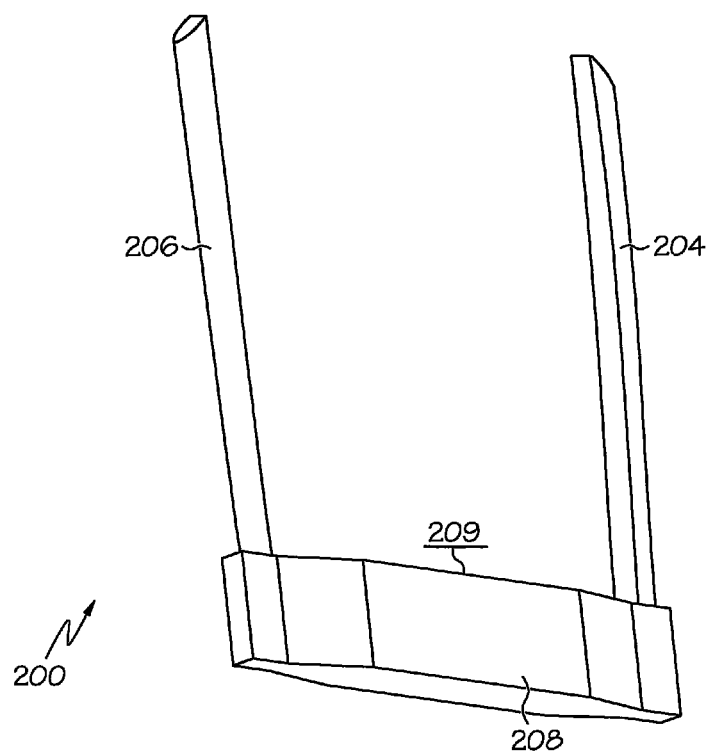
FIG. 20 is a perspective view of a dissolvable, or bioabsorbable, material overmolded onto the deformable member of FIG. 18 in accordance with one non-limiting embodiment of the present invention.
Figure 21:
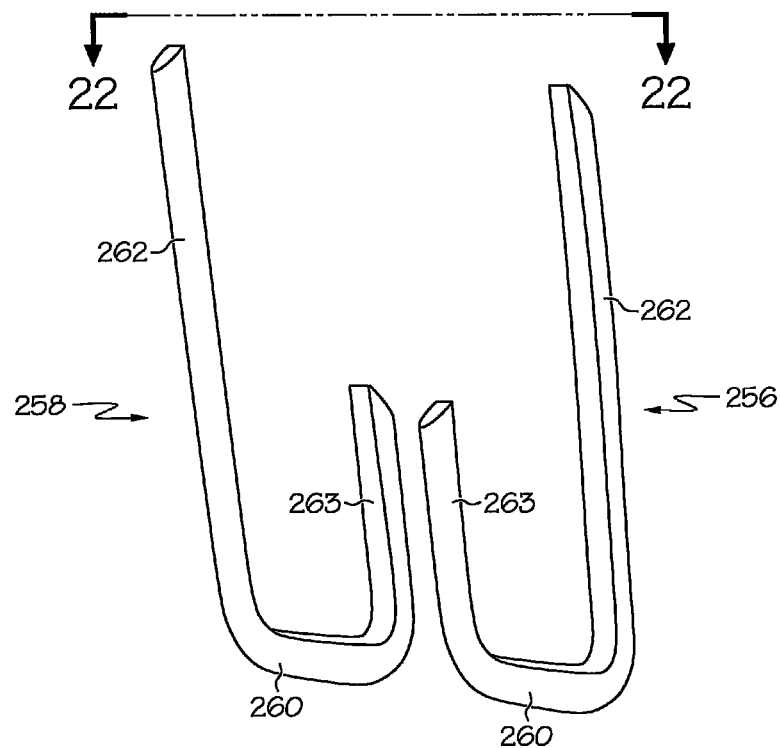
FIG. 21 is a perspective view of first and second deformable members of a staple in accordance with one non-limiting embodiment of the present invention.
Figure 22:
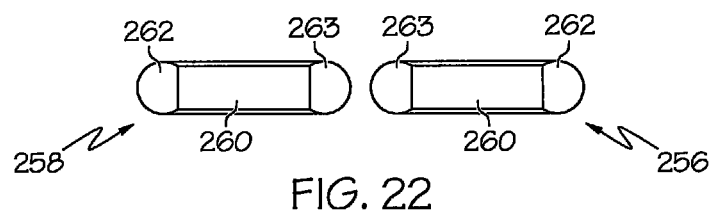
FIG. 22 is a top view of the deformable members of FIG. 21.
Figure 23:
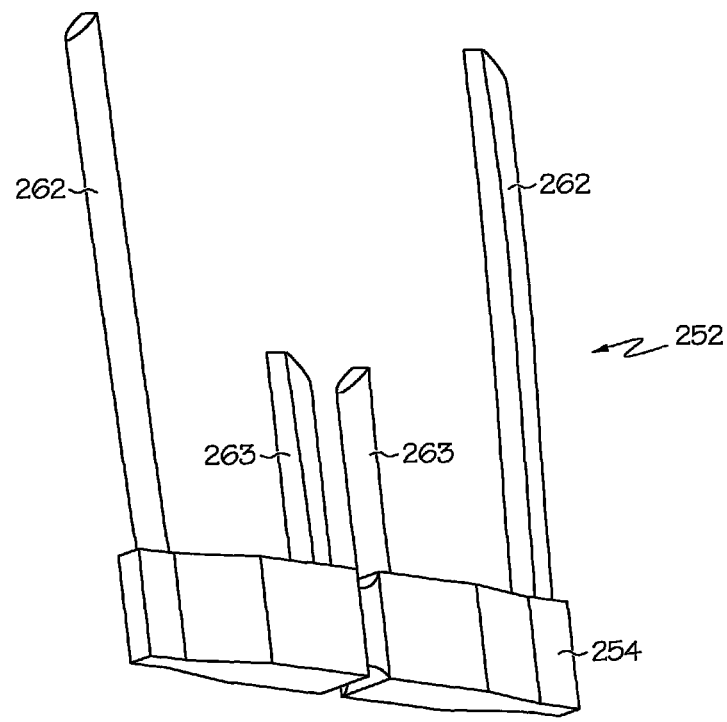
FIG. 23 is a perspective view of a dissolvable, or bioabsorbable, material overmolded onto the deformable members of FIG. 21 in accordance with one non-limiting embodiment of the present invention.
Figure 24:
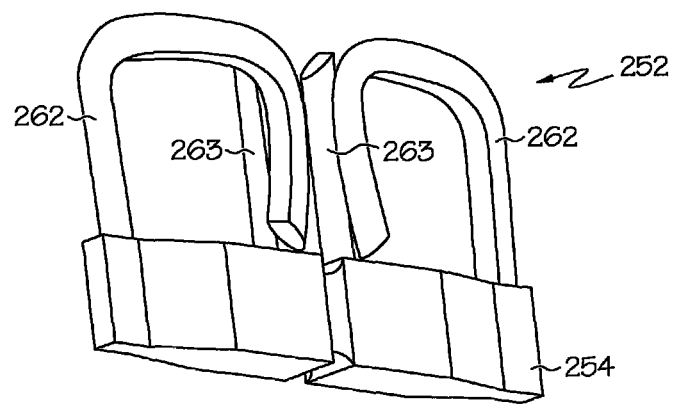
FIG. 24 is a perspective view of the staple of FIG. 23 in a deformed shape.
Figure 25:
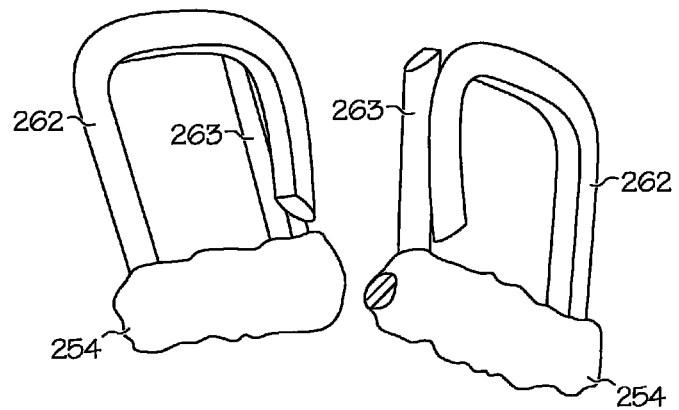
FIG. 25 is a perspective view of the staple of FIG. 23 wherein a portion of the dissolvable material has been dissolved and the first and second deformable members have moved relative to one another.
Figure 26:
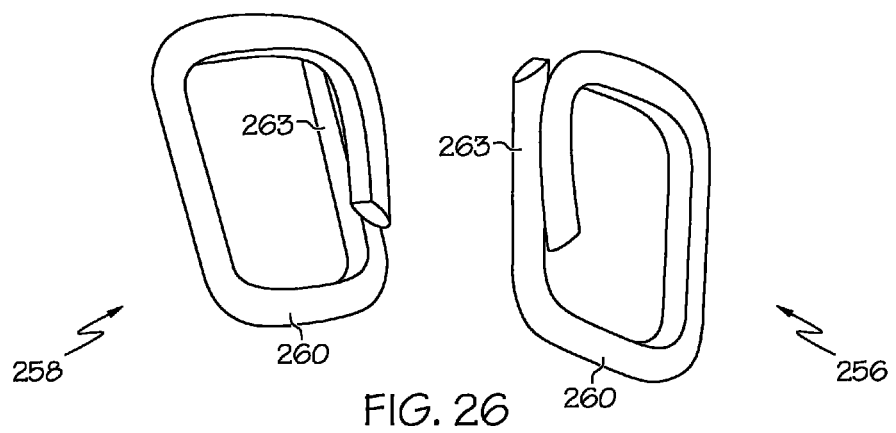
FIG. 26 is a perspective view of the staple of FIG. 24 after the dissolvable or bioabsorbable material has completely dissolved.
Figure 27:
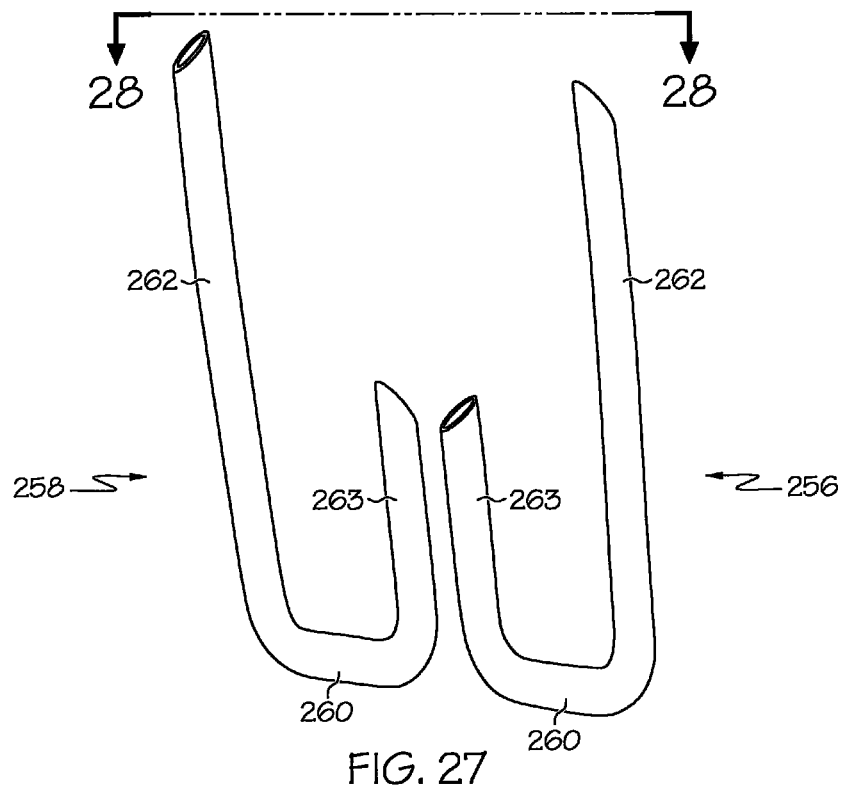
FIG. 27 is a perspective view of first and second deformable members having an expandable coating formed thereon in accordance with one non-limiting embodiment of the present invention.

In various embodiments, referring to FIGS. 18-20, surgical staple 200 can include base 202, first deformable member 204, and second deformable member 206 where deformable members 204 and 206 can extend from base 202. In at least one embodiment, at least a portion of base 202, first deformable member 204 and/or second deformable member 206 can have a non-circular cross-section. More particularly, referring to FIG. 19, the cross-section of deformable member 204, for example, can include arcuate portion 203 and flat portion 205. In various embodiments, referring to FIG. 18, base 202 and deformable members 204 and 206 can comprise wire 201, where wire 201 can include a cross-section which is substantially constant throughout the length of wire 201. In other embodiments, however, first deformable member 204 and second deformable member 206, for example, can have different cross-sections. In at least one such embodiment, first deformable member 204 can include a substantially circular cross-section and second deformable member 206 can include a non-circular cross-section. In other various embodiments, first deformable member 204 can include a non-circular cross-section which is different than a non-circular cross-section of second deformable member 206.

In various embodiments, the cross-sectional geometry of deformable members 204 and 206 can control the manner and direction in which deformable members 204 and 206 are bent when they are deformed by anvil 52 as described above. In at least one embodiment, referring to FIG. 19, flat portions 205 can be oriented such that they are facing each other and/or axis 207 and, as a result, flat portions 205 can cause deformable members 204 and 206 to bend toward axis 207 when a force is applied thereto. In other various embodiments, flat portions 205 can be oriented in any suitable manner to allow the deformable members to bend in a desired direction. In effect, the size and location of flat portion 205 can affect the moment of inertia of the cross-section and, correspondingly, affect the manner in which the deformable members respond to the bending stress applied thereto. In such embodiments, the deformation of deformable members 204 and 206 can be controlled in order to apply a desired compressive force to the soft tissue captured within staple 200. More particularly, in at least one embodiment, the deformable members can be bent until they contact the soft tissue and apply a compressive force to the soft tissue where the amount of force is largely determined by the amount and direction in which deformable members 204 and 206 are deformed.

In at least one embodiment, referring to FIGS. 19 and 20, crown 208 can be molded onto or positioned onto base 202, where crown 208 can be comprised of a dissolvable, biofragmentable, or bioabsorbable material. In various embodiments, crown 208 can include a compression surface against which soft tissue can be pressed when the soft tissue is captured within staple 200. In at least one embodiment, referring to FIG. 20, staple 200 can include compression surface 209 where compression surface 209 can include a wider profile, or larger surface area, than surface 211 of base 202. In such embodiments, as a result, the wider surface area of compression surface 209 may reduce the stress applied to the soft tissue captured therein. More particularly, for a given compression force applied to the soft tissue, the resultant stress in the soft issue is inversely proportionate to the area against which the compression force is applied. Stated another way, when a force is applied to the soft tissue over a small area, the resultant stress is large, and, when the same force is applied to the soft tissue over a large area, the resultant stress is small. In view of the above, the dimensions of compression surface 209 can be selected in order to achieve a desired stress in the soft tissue captured in staple 200.

In various embodiments, flat portions 205, as described above, can cooperate with compression surface 209 of crown 208 to control and/or reduce the stress applied to the soft tissue captured within staple 200. More particularly, in embodiments where a round portion of the deformable members contacts the soft tissue, the compressive force applied to the soft tissue may be applied across a very small area potentially resulting in a very high stress concentration in the soft tissue. In embodiments where a flat portion of the deformable members contacts the soft tissue, the force applied to the soft tissue can be applied across a greater surface area resulting in a lower stress concentration. In view of the above, the cross-sectional geometry of deformable members 204 and 206 and the dimensions of compression surface 209 can be selected such that they cooperate to apply a desired stress to the soft tissue. In embodiments where crown 208 is comprised of a dissolvable, biofragmentable, or bioabsorbable material, as described above, the compressive force or stress applied to the soft tissue can be reduced as crown 208 is dissolved. More particularly, in at least one embodiment, flat portions 205 and compression surface 209 can define a first distance therebetween when staple 200 is initially inserted into the soft tissue which results in a first force, and stress, being applied to the soft tissue and, after at least a portion of compression surface 209 has dissolved away, flat portions 205 and compression surface 209 can define a larger distance therebetween which can reduce the compressive force and thus, stress, applied to the soft tissue. In various embodiments, at least one of deformable members 204 and 206 can be comprised of a dissolvable, biofragmentable, or bioabsorbable material. In such embodiments, portions of deformable members 204 and 206 can, similar to the above, dissolve away to reduce the compressive force and stress to the soft tissue.

Referring to FIGS. 21-26, staple 252 can include first deformable member 256 and second deformable member 258 where each deformable member can include base 260, first deformable leg 262, and second deformable leg 263. Staple 252 can also include crown 254 which can be comprised of at least one overmolded or co-molded material. In at least one embodiment, crown 254 may be comprised of a first material overmolded onto deformable members 256 and 258 and a second material overmolded onto the first material, for example. In at least one such embodiment, the second material can be configured to dissolve away quickly thereby allowing deformable members 256 and 258 to separate from each other early in the healing process. The first material, however, can be selected to dissolve at a slower rate than second material in order for crown 254 of staple 252 to continue to provide a compressive force on the tissue even after the second material has completely dissolved away. In at least one embodiment, the first material can be injection molded onto deformable members 256 and 258 and then permitted to cure, and/or substantially solidify, before the second material is injection molded onto the first material. In other various embodiments, the first material and the second material can be injection molded onto deformable members 256 and 258 at substantially the same time or in rapid succession. In these embodiments, the first and second materials can chemically bond together to provide sufficient strength therebetween so that staple 252 may be handled without the first and second materials separating from one another. In other embodiments, the first and second materials can form mechanically interlocking features to accomplish the same result.

Figure 37:
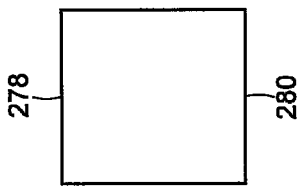
FIG. 37 is a cross-sectional view of the deformable member of FIG. 36.
Figure 36:
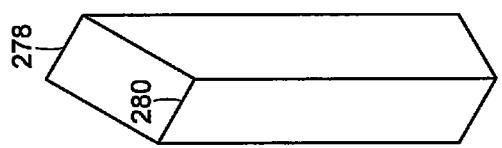
FIG. 36 is a perspective view of an end portion of another deformable member in accordance with one non-limiting embodiment of the present invention.
Figure 35:
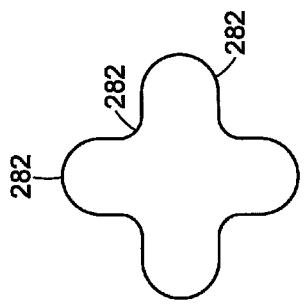
FIG. 35 is a cross-sectional view of the deformable member of FIG. 34.
Figure 34:
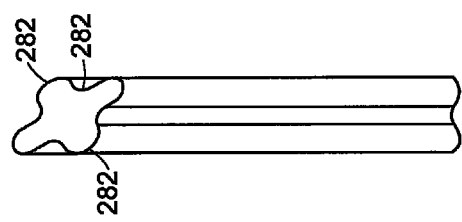
FIG. 34 is a perspective view of an end portion of a deformable member in accordance with one non-limiting embodiment of the present invention.
Figure 41:
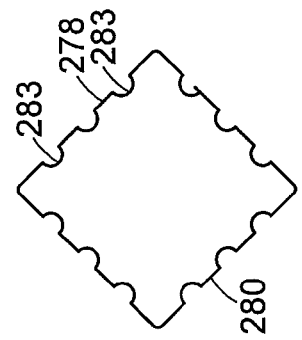
FIG. 41 is a cross-sectional view of the deformable member of FIG. 40.
Figure 40:
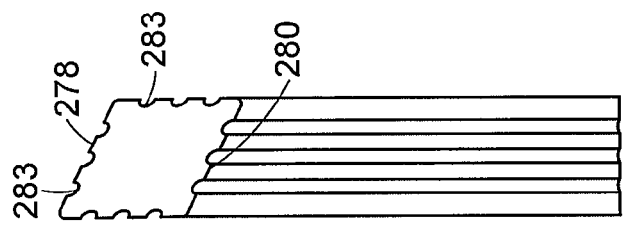
FIG. 40 is a perspective view of an end portion of another deformable member in accordance with one non-limiting embodiment of the present invention.
Figure 39:
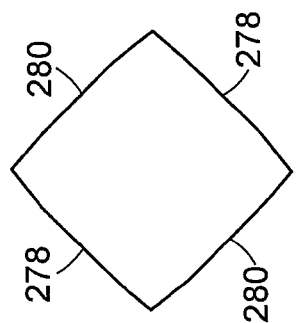
FIG. 39 is a cross-sectional view of the deformable member of FIG. 38.
Figure 38:
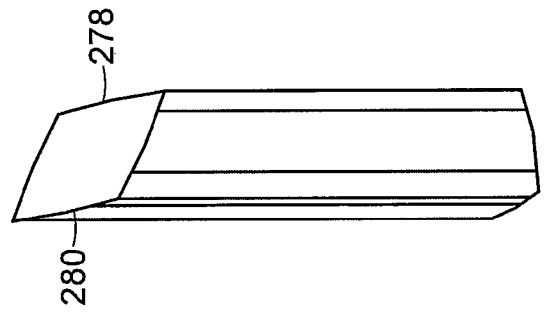
FIG. 38 is a perspective view of an end portion of another deformable member in accordance with one non-limiting embodiment of the present invention.
Figure 58:
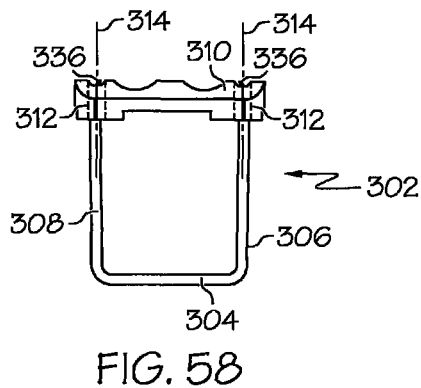
FIG. 58 is an elevational view of a surgical staple having a slidable crown in accordance with one non-limiting embodiment of the present invention.

Similar to the above, referring to FIGS. 21-26, at least portions of deformable members 256 and 258 can include a non-circular cross-section. In the various embodiments illustrated in FIGS. 34-57, the cross-sections of the deformable members can include various combinations of flat, arcuate, and/or radiused surfaces. In the embodiment illustrated in FIGS. 34 and 35, for example, the cross-section of a deformable member can include a plurality of arcuate surfaces 282. In the embodiment illustrated in FIGS. 36 and 37, the cross-section of a deformable member can include a plurality of substantially flat surfaces 278 and 280. In various embodiments, the cross-section can comprise a triangle, a rectangle, a square, an oval, a hexagon, a pentagon, a trapezoid or any other suitable shape. In either event, the cross-sections can be symmetrical or asymmetrical. In various embodiments, the cross-sections can be configured, as described above, to allow the deformable members to bend in a particular direction. In at least one embodiment, referring to FIGS. 40 and 41, flat surfaces 278 and 280 can include grooves, or recesses, 283 which can reduce the moment of inertia of the cross-section about at least one axis where the deformable member is more susceptible to bending about such an axis.

Figure 28:
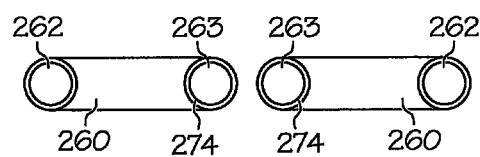
FIG. 28 is a top view of the deformable members of FIG. 27.
Figure 29:
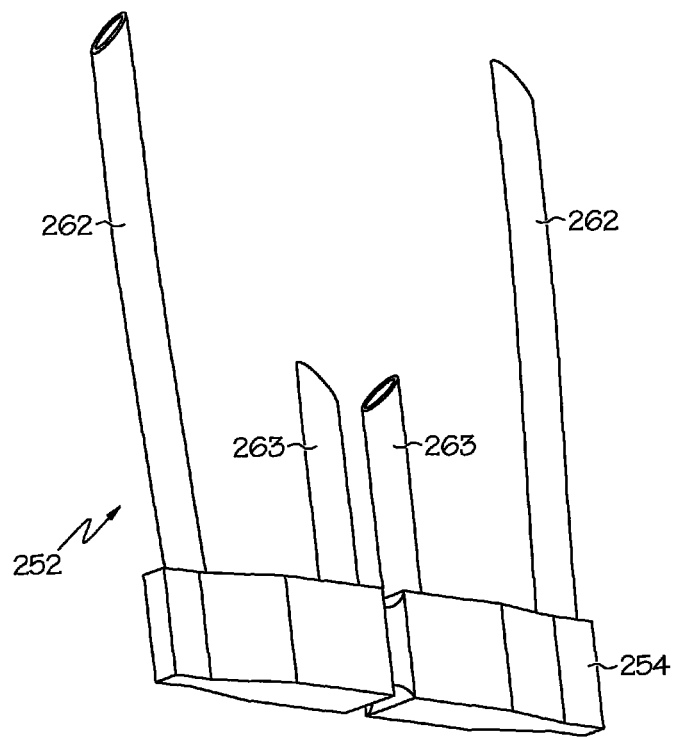
FIG. 29 is a perspective view of a dissolvable, or bioabsorbable, material overmolded onto the first and second deformable members of FIG. 27 in accordance with one non-limiting embodiment of the present invention.
Figure 30:
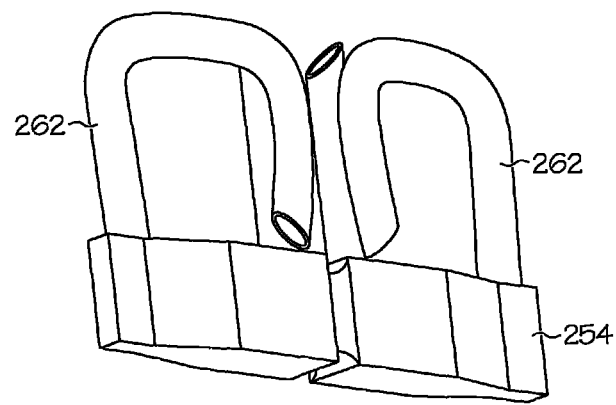
FIG. 30 is a perspective view of the staple of FIG. 29 in a deformed configuration.
Figure 31:
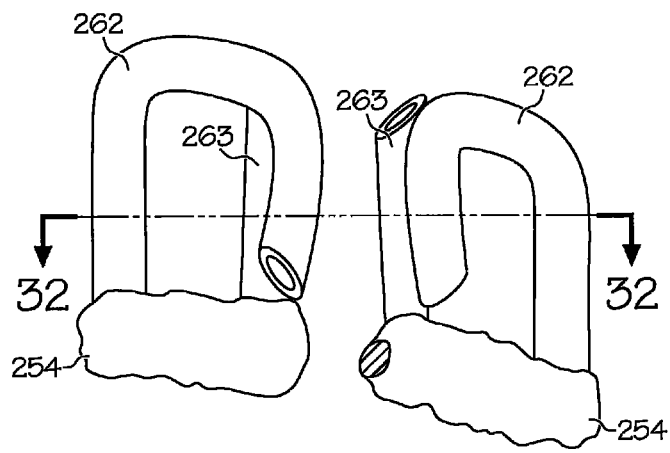
FIG. 31 is a perspective view of the staple of FIG. 29 after at least a portion of the dissolvable material has dissolved and the expandable material has expanded.
Figure 32:
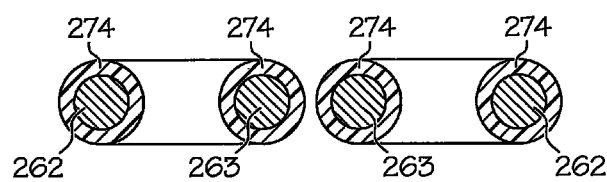
FIG. 32 is a top view of the staple of FIG. 29 illustrating the expandable coating in an expanded form.
Figure 33:
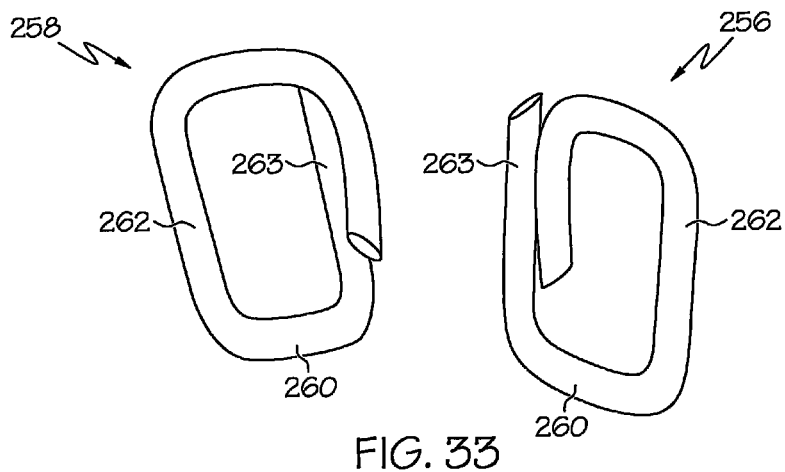
FIG. 33 is a perspective view of the staple of FIG. 29 after the dissolvable material and the expandable material has completely dissolved.

As described above, when deformable members 256 and 258, for example, are inserted through soft tissue, the deformable members can puncture the soft tissue creating holes therein. As a result, eventhough the deformable members can substantially fill the puncture holes, blood may flow, at least initially, from the soft tissue surrounding the puncture holes. In various embodiments of the present invention, at least a portion of the deformable members can expand and apply a compressive force against the soft tissue in order to stop, or at least reduce, bleeding from the soft tissue surrounding the puncture holes. In at least one embodiment, referring to FIGS. 27-33, at least a portion of first and second deformable members 256 and 258 can be coated with expandable coating 274. In various embodiments, referring to FIG. 28, expandable coating 274 can have a first diameter when it is initially inserted into the soft tissue and can apply, depending upon the size of the deformable members and the puncture holes, a first compressive force to the soft tissue surrounding the deformable members. Thereafter, referring to FIG. 32, expandable coating 274 can increase in size to apply a larger, or second, compressive force to the soft tissue surrounding the deformable members. In various embodiments, this second compressive force may be sufficient to close, or at least constrict, the blood vessels in the soft tissue surrounding the puncture hole to eliminate, or at least reduce, the flow of blood therethrough.

In various embodiments, expandable coating 274 can be comprised of a hydrophilic material, or any other suitable material which has an affinity for water, that can absorb blood, or other fluids in the surgical site, in order to expand as described above. In at least one embodiment, a fluid can be introduced into the surgical site which can cause expandable coating 274 to expand. In various embodiments, expandable coating 274 can be comprised of a cross-linked ester compound having a polyethylene glycol base polymer, for example. In at least one such embodiment, expandable coating 274 can be overmolded onto at least a portion of staple 252 using an injection molding process. In other various embodiments, the deformable members and/or crown can be entirely comprised of an expandable material. In either event, after expandable material 274 has expanded, at least a portion thereof can begin to dissolve and can be absorbed by the patient's body. In such embodiments, the second compressive force applied to the soft tissue can be relaxed and the soft tissue can be permitted to expand and grow in order to fill the puncture holes. Such embodiments can be particularly useful when the deformable members are also comprised of dissolvable or bioabsorbable materials as described above. In various embodiments, the expandable coating can also comprise a therapeutic agent, for example, which can be released as expandable coating 274 is dissolved.

While expandable coating 274 is demonstrated in connection with a staple having deformable members with substantially circular cross-sections, expandable coating 274 can also be applied to deformable members having a non-circular cross-section including, but not limited to, the cross-sections disclosed in FIGS. 34-57. In other various embodiments, expandable coating 274 can be applied to any other suitable type of surgical fastener. In at least one such embodiment, a suture, or surgical thread, can be at least partially coated with an expandable coating. In use, the suture, or thread, can create puncture holes in the soft tissue when they are inserted therein and the expandable coating can expand to fill the puncture holes as described above.

In various embodiments, referrring to FIGS. 58-66, staple 302 can include base 304, first deformable member 306, and second deformable member 308. In at least one embodiment, staple 302 can further include crown 310 having apertures 312 defined therein which can be configured to receive first deformable member 306 and second deformable member 308. As described in further detail below, deformable members 306 and 308 can be configured to move, or slide, within apertures 312 such that base 304 can be moved relative to crown 310. In at least one such embodiment, each aperture 312 can define an axis 314 extending therethrough where deformable members 306 and 308 can be configured to move along axes 314 when they are moved within apertures 312. In various embodiments, crown 310, referring to FIGS. 61-63, can include recess 320 which can be configured to receive base 304 and at least limit, if not prevent, relative movement between base 304 and crown 310. In at least one embodiment, base 304 can be movably positioned within recess 320 such that recess 320 can permit deformable members 304 and 306 to move along axes 314 but at least inhibit base 304 from moving transversely to axes 314. In various embodiments, recess 320 can be configured to receive base 304 in a press-fit and/or snap-fit configuration such that, once base 304 is positioned in recess 320, base 304 can be substantially immovable relative to crown 310.

In various embodiments, referring to FIGS. 67-70, staples 302 can be removably stored within a staple cartridge, such as staple cartridge 318, for example. In at least one embodiment, staple cartridge 318 can include body 326 having cavities 316 defined therein. Staple cartridge body 326 can further include deck 328 having top surface 330 where cavities 316 can include an opening in top surface 330. In various embodiments, each cavity 316 can be configured to receive at least a portion of a base 304 and deformable members 306 and 308 of a staple 302 where deck 328 can include recesses 334 which can be configured to receive crowns 310. In use, referring to FIG. 67, base 304 can be situated in a first position in cavity 316 before it is moved toward crown 310. In at least one embodiment, deformable members 306 and 308 can include ends 336 where, in this first position, ends 336 can be positioned within or proximal to apertures 312. In such embodiments, as a result, when deformable members 306 and 308 are moved relative to crown 310 as described above, deformable members 306 and 308 can already be aligned with axes 314 and the possibility of deformable members 306 and 308 becoming misaligned with apertures 312 can be reduced.

Figure 67:
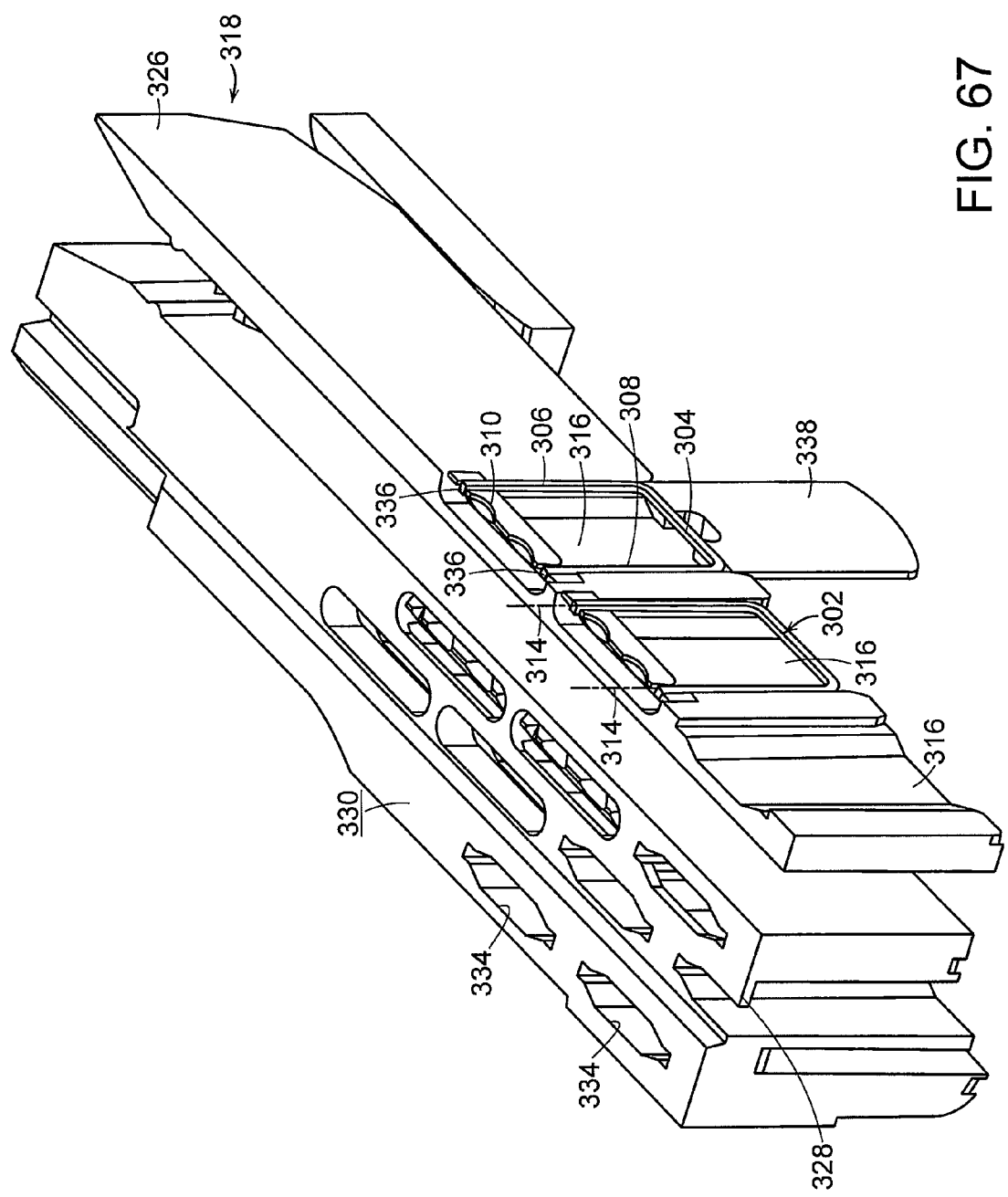
FIG. 67 is a perspective cross-sectional view of a non-deployed surgical staple of FIG. 58 positioned within a staple cartridge in accordance with one non-limiting embodiment of the present invention.
Figure 68:
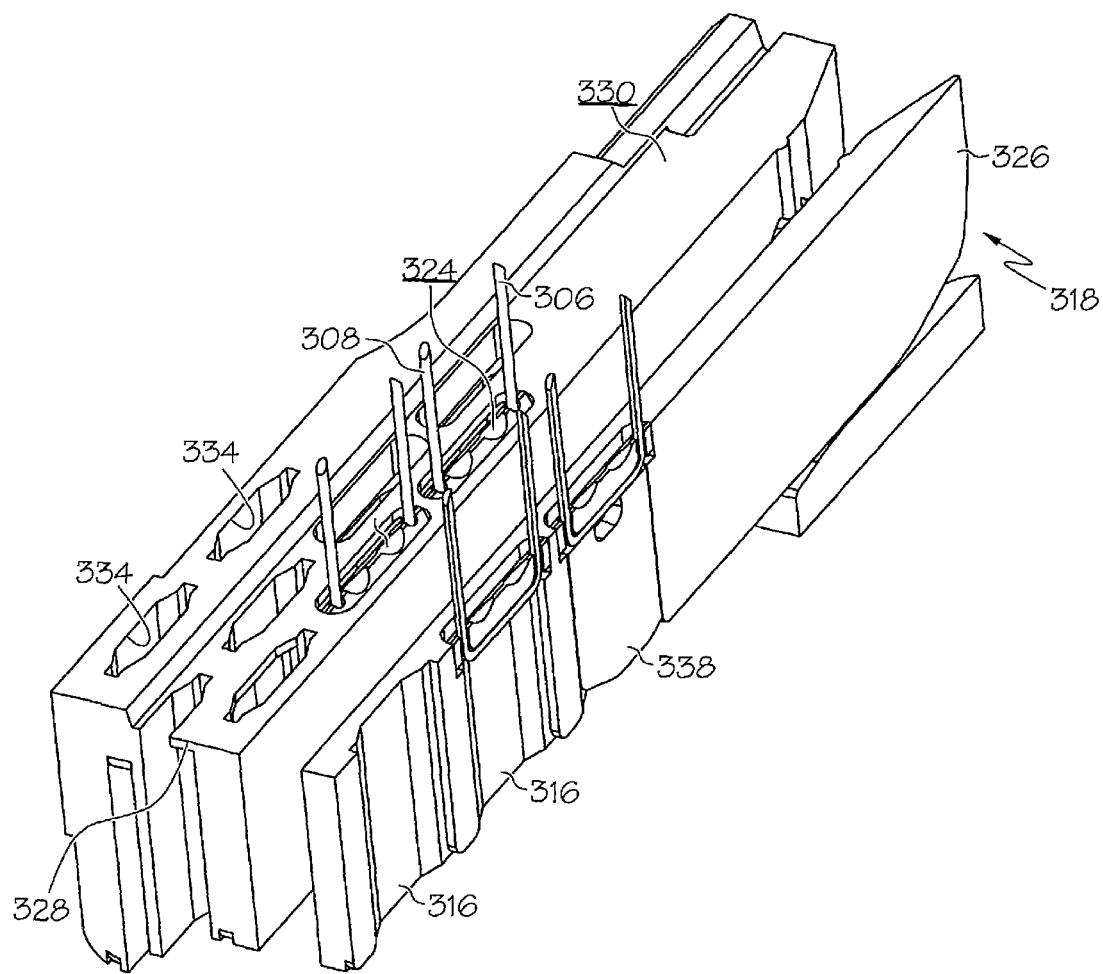
FIG. 68 is a perspective cross-sectional view of the staple of FIG. 67 in a partially deployed position.
Figure 69:
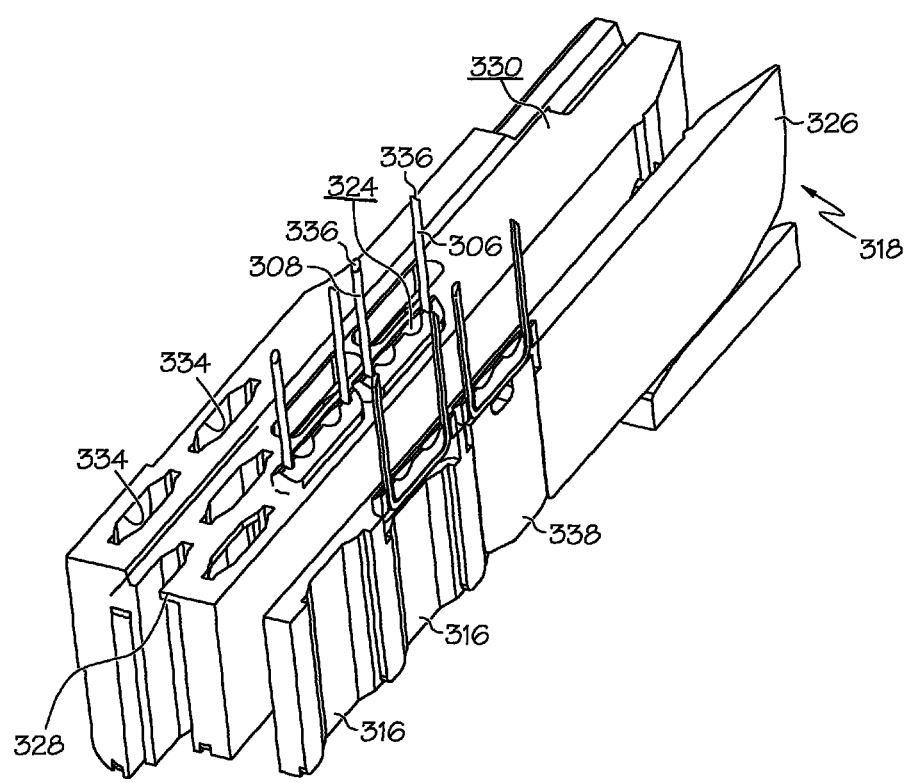
FIG. 69 is a perspective cross-sectional view of the staple of FIG. 67 in a fully deployed position.
Figure 70:
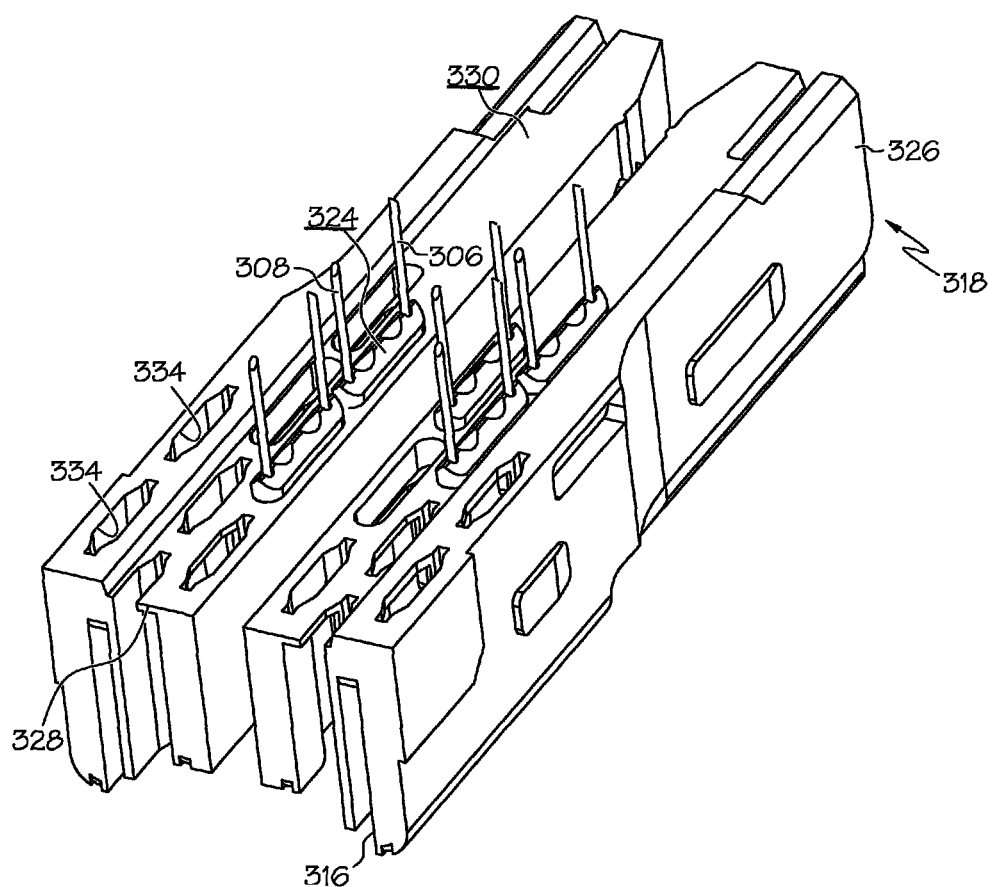
FIG. 70 is a perspective view of the staple of FIG. 67 in a fully deployed position.
Figure 71:
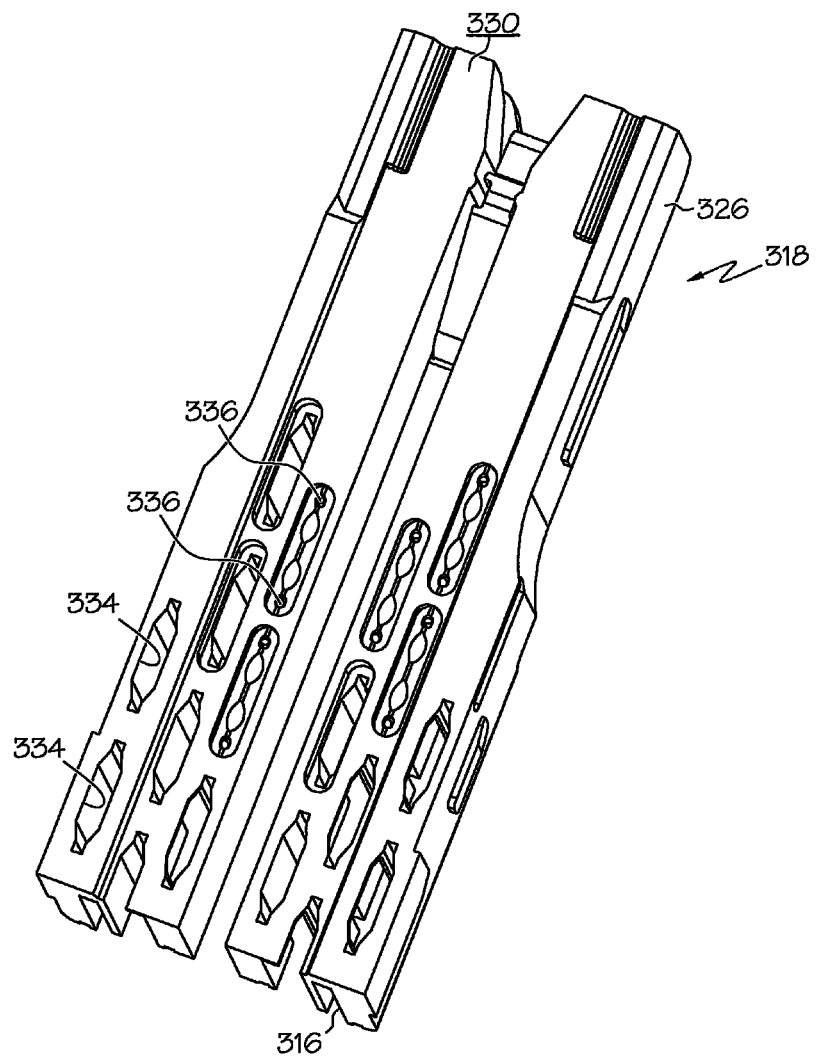
FIG. 71 is perspective view of the staple cartridge of FIG. 67 illustrating several surgical staples in an undeployed position.
Figure 72:
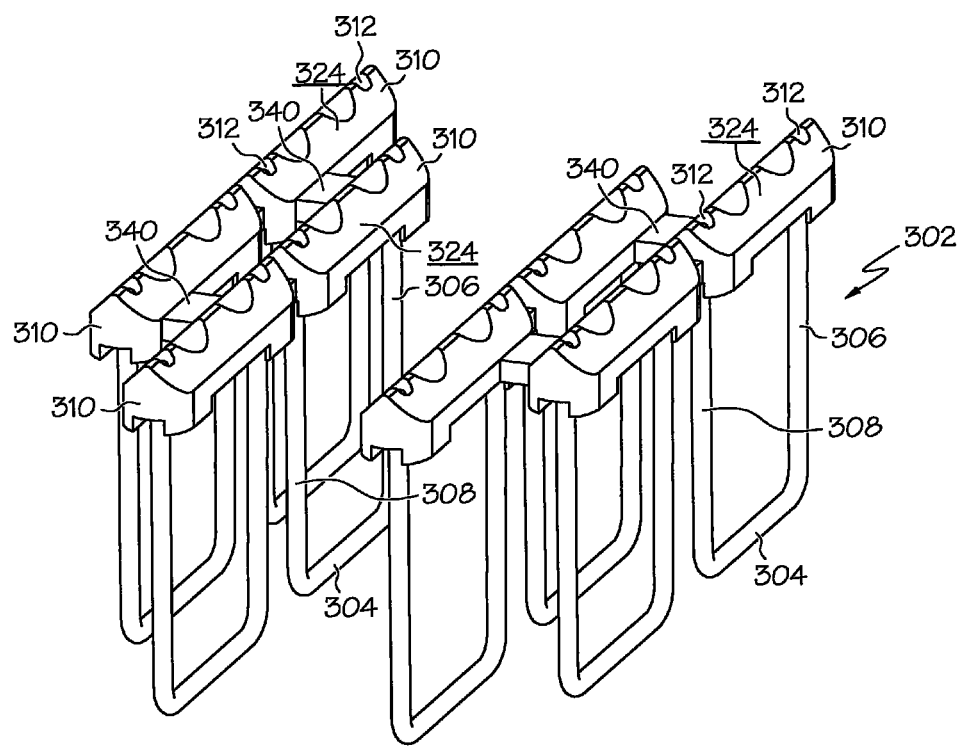
FIG. 72 is a perspective view of an assembly of a plurality of the staples of FIG. 58 connected by bridges in accordance with one non-limiting embodiment of the present invention.
Figure 73:
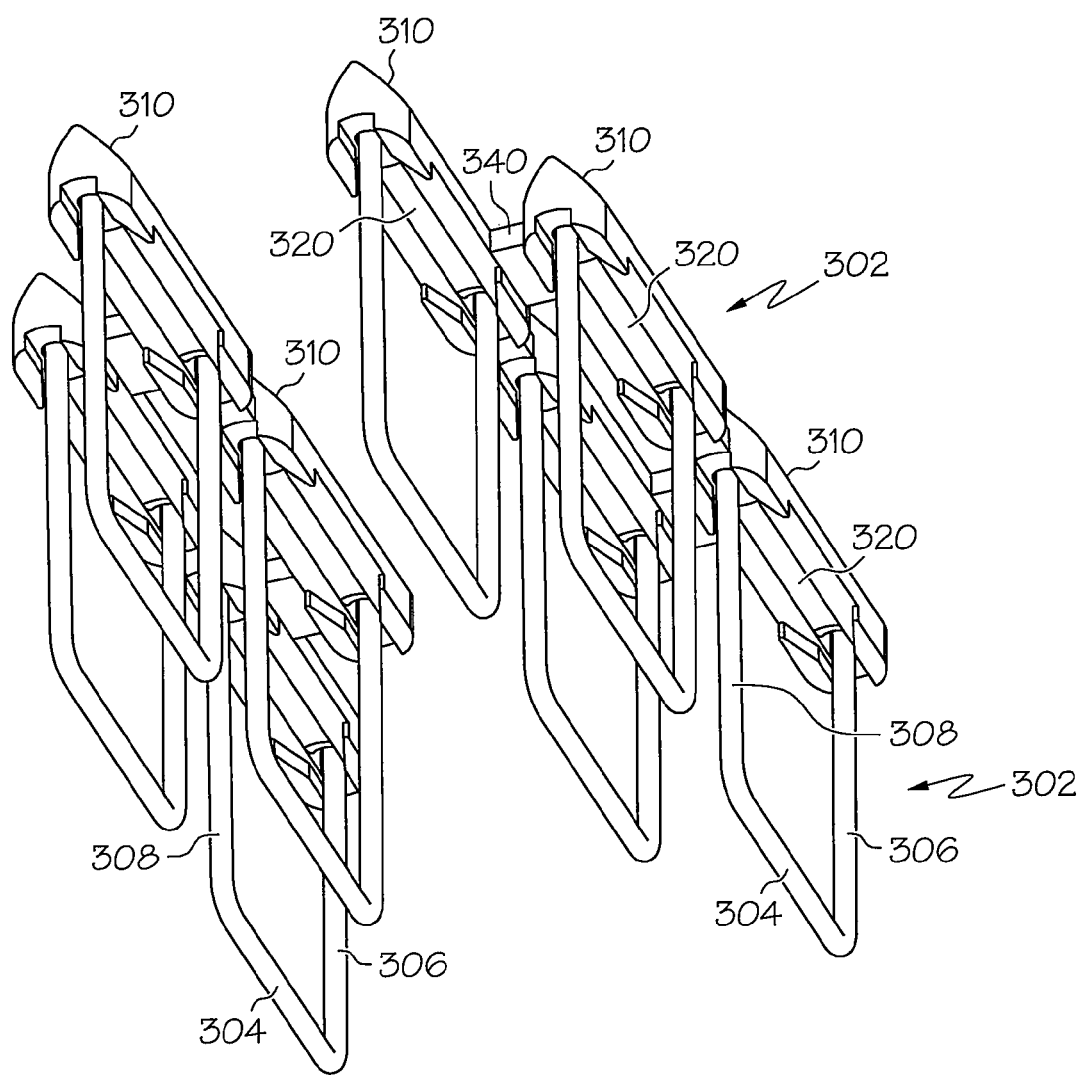
FIG. 73 is another perspective view of the assembly of FIG. 72.

In various embodiments, referring to FIGS. 67 and 68, deformable members 306 and 308 and base 304 can be moved, or slid, relative to crown 310 by driver 338. In at least one embodiment, the staple cartridge can further include a sled configured to lift driver 338 and move base 304 toward crown 310. Although the sled is not illustrated in FIGS. 67 and 68, exemplary sleds are described and illustrated in the present application including sled 62 in FIGS. 3 and 10. In various embodiments, referring to FIG. 68, driver 338 can push or slide base 304 until base 304 contacts crown 310 and engages recess 320 as described above and deformable members 306 and 308 are inserted into soft tissue positioned above top surface 330. Thereafter, referring to FIG. 69, base 304 and crown 310 can be forced upwardly by driver 338 such that crown 310 is removed, or ejected, from recess 334. In various embodiments, crown 310 can be press-fit or snap-fit within recesses 334 such that driver 338 must apply a sufficient force to dislodge crown 310 from recess 334. In other various embodiments, although not illustrated, crown 310 can be integrally molded with deck 328 such that driver 338 must apply a sufficient force to base 304 to break crown 310 away from staple cartridge body 326.

In various embodiments, driver 338 can be configured to drive deformable members 306 and 308 against an anvil such that the deformable members are deformed by the anvil, as described above. Thereafter, as described above, the deformable members can capture the soft tissue and compress it against crown 310. In various embodiments, crown 310 may further include tissue-contacting surface 324 which can be used to control the compressive pressure applied to the soft tissue. More particularly, when surface 324 includes a large area against which the soft tissue can be compressed, the compressive pressure applied to the soft tissue can be much less than when surface 324 includes a smaller area. In at least one embodiment, tissue-contacting surface 324 can have a first width and base 304 can have a second width. In at least one such embodiment, the first width of tissue-contacting surface 324 can be wider than the second width of base 304 such that only tissue-contacting surface 324 comes into contact with tissue during staple 302 deployment or firing.

In various embodiments, tissue can be captured and compressed between staple cartridge 318 and the anvil before staples 302 are deployed into the soft tissue. In at least one embodiment, crowns 310 can be positioned within recesses 334 of staple cartridge body 326 such that surfaces 324 of crowns 310 can be aligned, or substantially flush, with top surface 330 of deck 328. In at least one such embodiment, the compressive force, or pressure, applied to the soft tissue by deck 328 and crowns 310 can be substantially the same. In other various embodiments, crowns 310 can be positioned within recesses 334 such that surfaces 324 are positioned above top surface 330 of staple deck 328. In such embodiments, the compressive force, or pressure, applied to the soft tissue by crowns 310 can be greater than the compressive force, or pressure, applied by deck 318. In various embodiments, the relative distance between surfaces 324 and top surface 330 can be selected to provide a desired pre-deployment compression force, or pressure, to the soft tissue. In other various embodiments, surfaces 324 can be positioned below top surface 330 of deck 328 such that the compression force, or pressure, applied to the soft tissue by surfaces 324 is less than the compressive force, or pressure, applied by deck 328.

Figure 59:
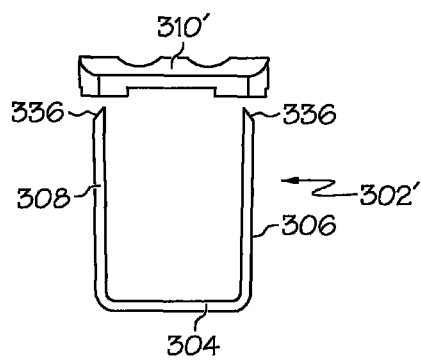
FIG. 59 is an elevational view of another surgical staple having a slidable crown in accordance with one non-limiting embodiment of the present invention.
Figure 60:
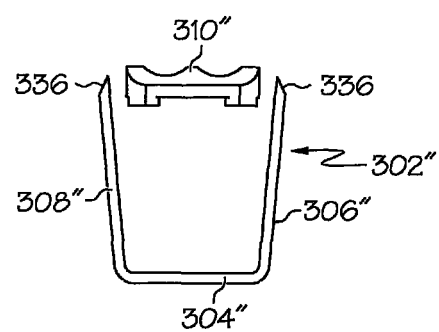
FIG. 60 is an elevational view of another surgical staple having a slidable crown in accordance with one non-limiting embodiment of the present invention.
Figure 61:
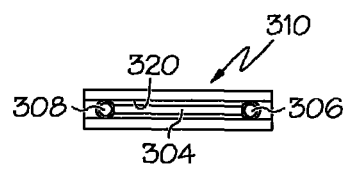
FIG. 61 is a bottom view of the surgical staple of FIG. 58.
Figure 62:
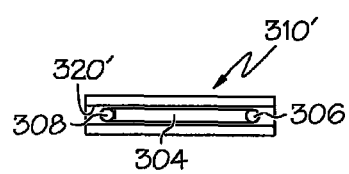
FIG. 62 is a bottom view of the surgical staple of FIG. 59.
Figure 63:
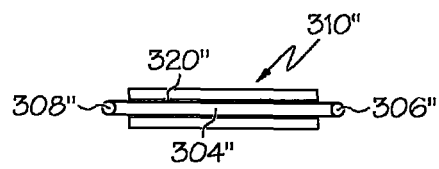
FIG. 63 is a bottom view of the surgical staple of FIG. 60.
Figure 64:
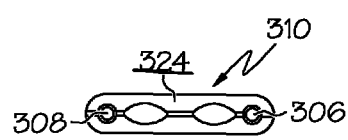
FIG. 64 is a top view of the surgical staple of FIG. 58.
Figure 65:
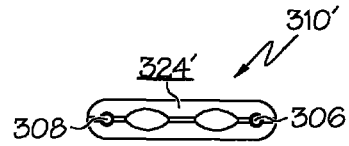
FIG. 65 is a top view of the surgical staple of FIG. 59.
Figure 66:
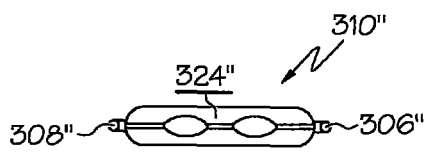
FIG. 66 is a top view of the surgical staple of FIG. 60.

In various embodiments, referring to FIGS. 59, 62, and 65, staple 302' can include deformable members 306 and 308 which may be configured to pierce crown 310' in lieu of passing through apertures 312. In such embodiments, ends 336 of the deformable members can be sharp enough to puncture crown 310' and create holes therein which can allow deformable members 306 and 308 to move, or slide, relative thereto. In other various embodiments, referring to FIGS. 60, 63, and 66, deformable members 306" and 308" can be positioned outside the perimeter of crown 310". In at least one such embodiment, although not illustrated, crown 310" can include recesses, or slots, which can be configured to slidably receive deformable members 306" and 308".

In various embodiments, referring to FIGS. 72-76, several staples can be connected together in order to control the distribution of the compressive force or pressure applied to the soft tissue captured within the staples. In at least one embodiment, the crowns 310 of several staples 302 can be connected together by bridges 340 such that bridges 340 and crowns 310 can apply a compresive force to the soft tissue over a larger area and reduce the pressure and stress applied to the soft tissue. In various embodiments, bridges 340 can also assist in preventing a staple 302 from tearing through or being pulled from the soft tissue. More particularly, when an excessively high force is applied to a particular staple 302, this force can be distributed to one or more other staples 302 in the soft tissue via bridges 340 and possibly prevent the soft tissue from being damaged. In various embodiments, tissue-contacting surfaces 324 can be positioned above bridges 340 such that bridges 340 apply a lesser compressive force, or pressure, to the soft tissue than crowns 310. In other various embodiments, although not illustrated, the top surfaces of bridges 340 can be aligned, or substantially flush, with surfaces 324 such that crowns 310 and bridges 340 can apply subtantially the same compressive force, or pressure, to the soft tissue. In various embodiments, bridges 340 can be flat, contoured, arcuate or any other suitable shape and can have any suitable cross-sectional arrangement.

Figure 74:
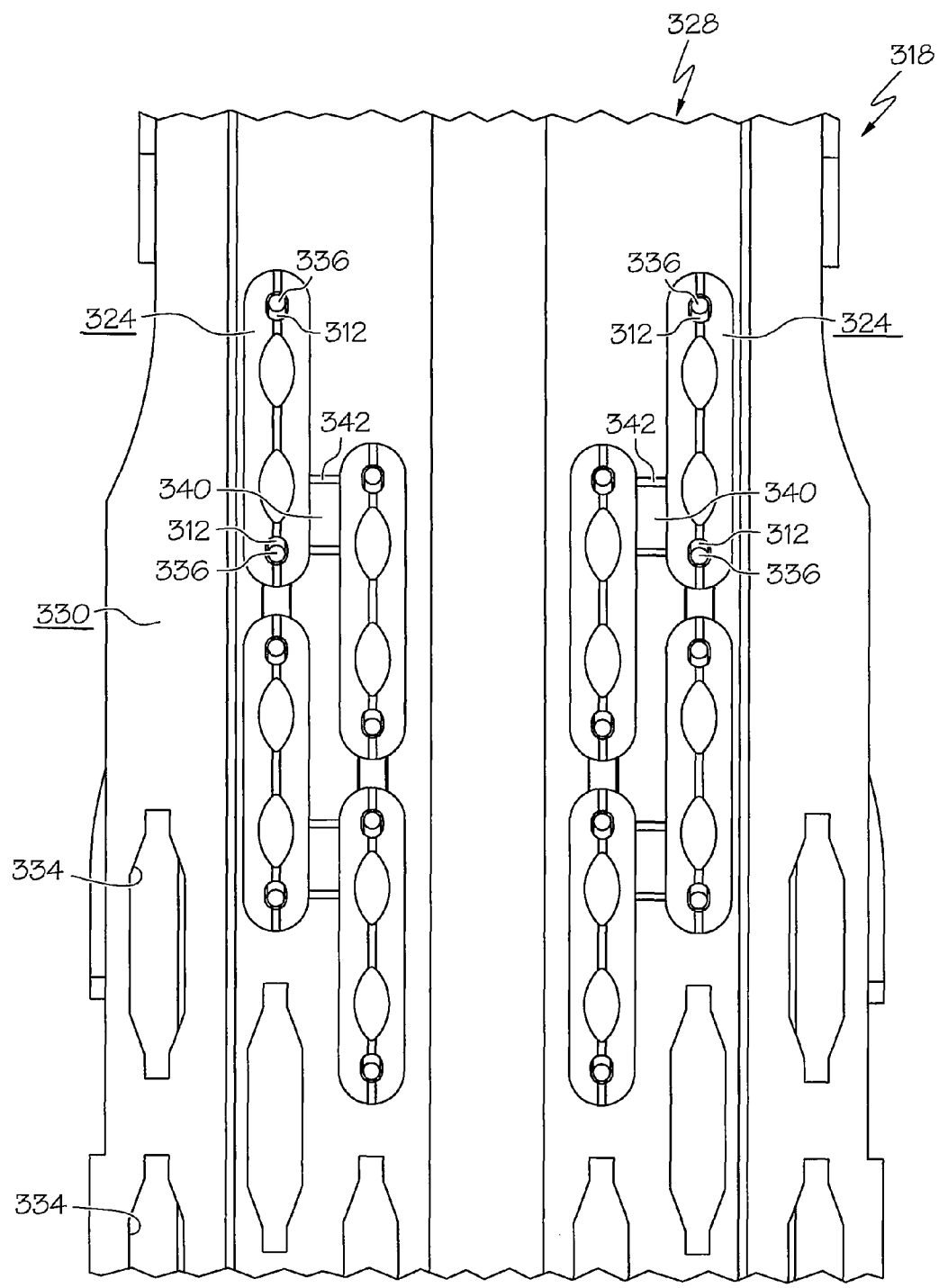
FIG. 74 is a top view of a staple cartridge with the assembly of FIG. 72 situated therein in accordance with one non-limiting embodiment of the present invention.
Figure 75:
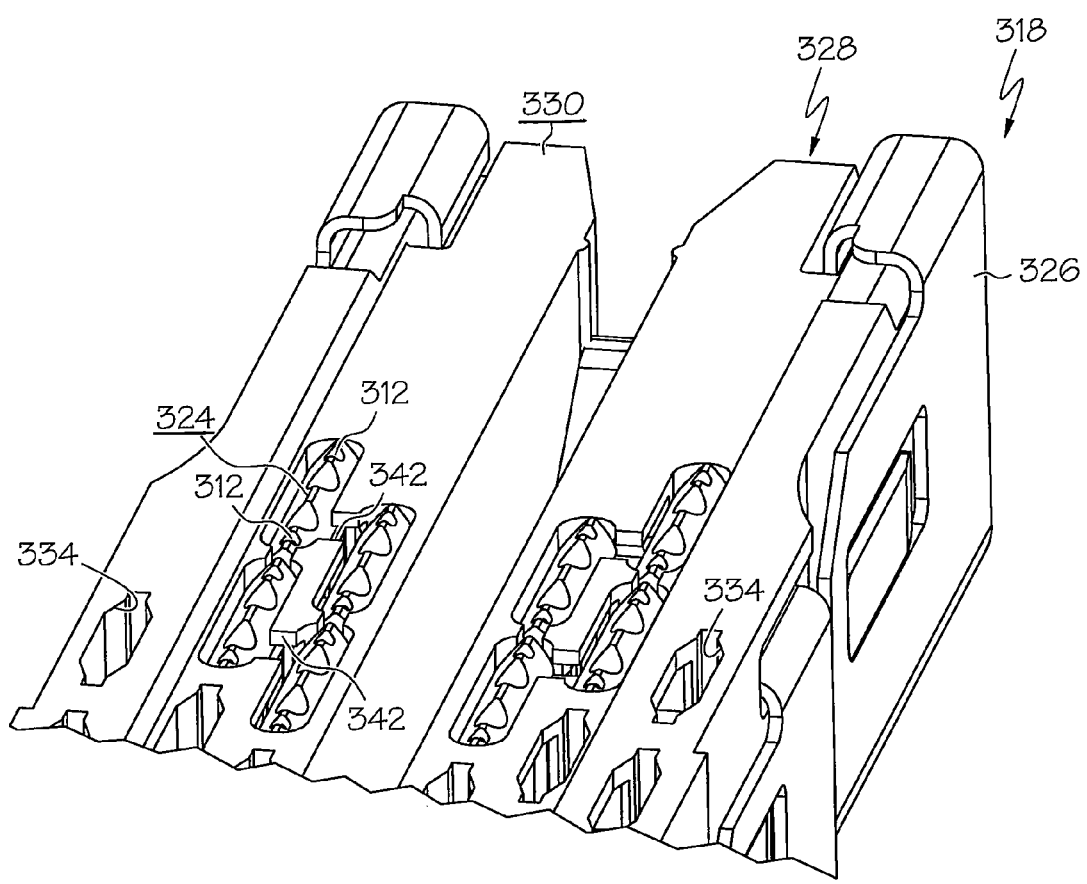
FIG. 75 is a partial perspective view of the staple cartridge of FIG. 74.
Figure 76:
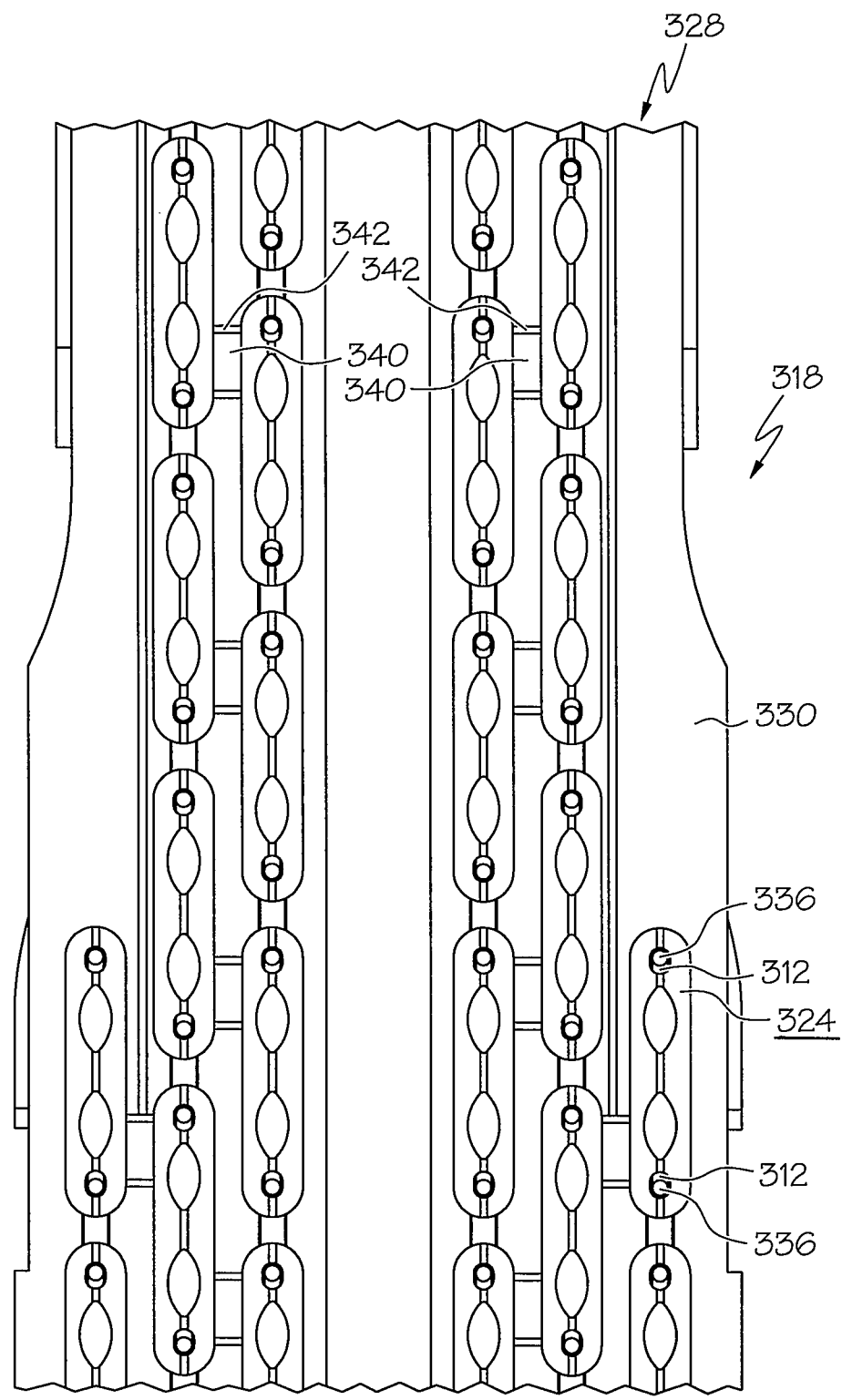
FIG. 76 is a top view of a staple cartridge and staple assemblies in accordance with one non-limiting embodiment of the present invention.

In various embodiments, referring to FIGS. 74 and 75, staple cartridge 318 can further include intermediate recesses 342 defined in deck 328 where recesses 342 can be configured to accept bridges 340. In various embodiments, bridges 340 can be positioned within recesses 342 such that they can be removed therefrom when staples 302 are deployed as described above. In other various embodiments, bridges 340 can be press-fit, snap-fit, or integrally molded with deck 328. Similar to the above, a staple driver can be configured to apply a sufficient force to staples 302 and/or bridges 340 to dislodge bridges 340 from deck 328. In either event, the driver, although not illustrated in FIGS. 72-76, can be configured to deploy the connected staples 302 at substantially the same time. In other various embodiments, bridges 340 can be flexible enough to permit the driver to deploy the connected staples 302 in series. In various embodiments, although not illustrated, more than one bridge 340 can be used to connect the crowns 310 of adjacent staples 302. In at least one embodiment, four or more adjacent staples 302 can be connected to each other by bridges 340, however other embodiments are envisioned including more than or less than four connected staples.

In various embodiments, referring to FIG. 74, staples 302 can be positioned in several rows, or lines, where bridges 340 can connect staples 302 which are in the same row and/or in different rows. By way of example, referring to FIGS. 74-76, crowns 310 of staples 302 in a first row can be connected while, in the same embodiment, the crowns 310 of these staples can be connected to crowns 310 of staples 302 in a second and/or third row. In various embodiments, bridges 340 and crowns 310 can be injection molded onto bases 304. In at least one embodiment, bridges 340 and crowns 310, or portions thereof, can be comprised of an absorbable, biofragmentable, or dissolvable material. In various embodiments, bridges 340 and crowns 310 can be at least partially comprised of a therapeutic drug as discussed above.

Figure 84:
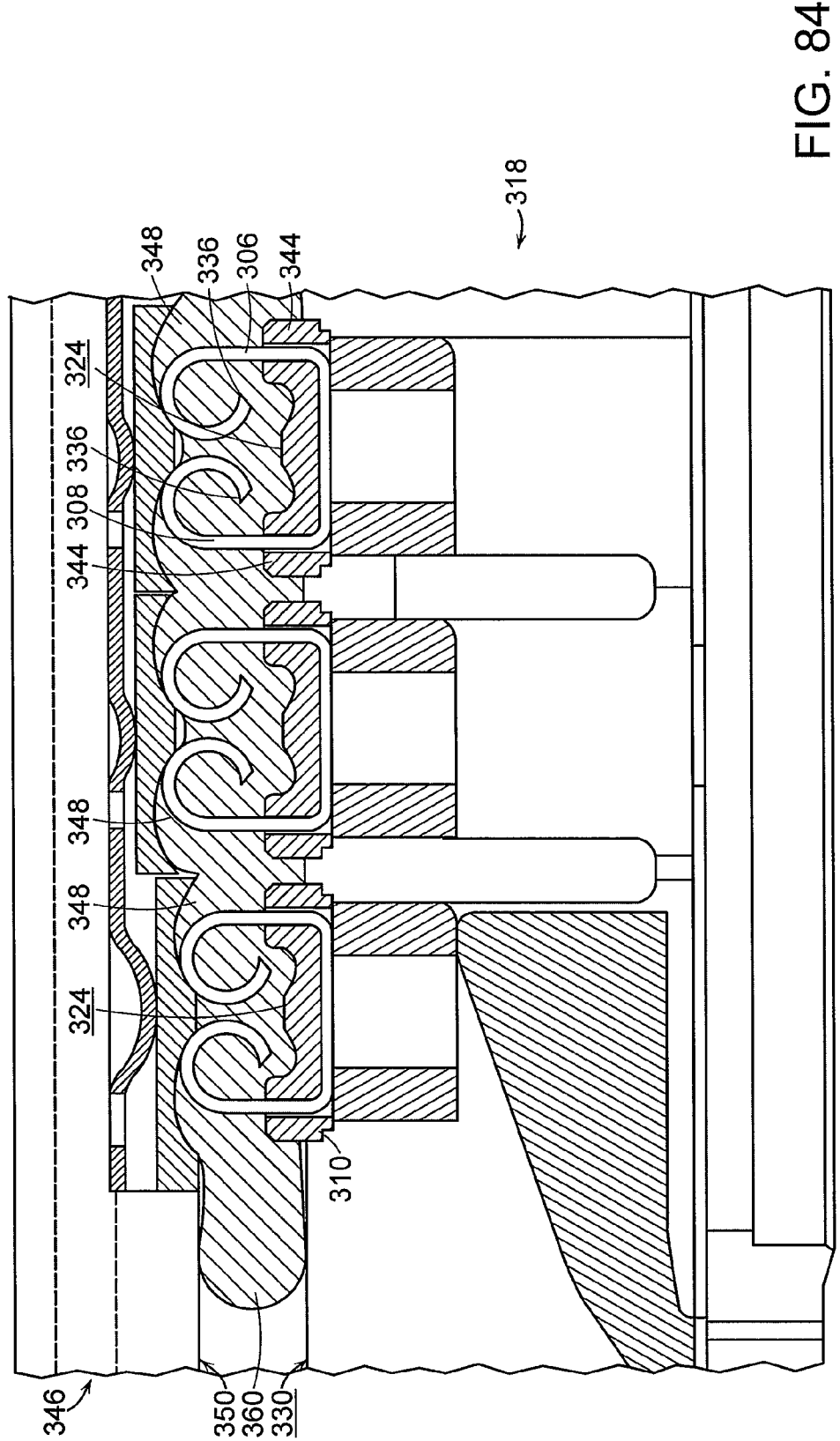
FIG. 84 is cross-sectional view of a surgical stapler deploying the staples of FIG. 77.

In various embodiments, as described above, soft tissue can be compressed between an anvil and a staple cartridge, for example, before staples are deployed from the staple cartridge. In various embodiments, referring to FIG. 84, soft tissue 360 can be compressed between anvil 346, top surface 330 of staple cartridge 318, and tissue contacting surfaces 324 of staple crowns 310. In at least one embodiment, such compression can push blood, or other fluids, out of soft tissue 360 and reduce the thickness of soft tissue 360 before the staples are inserted therein which can allow the staples to achieve a greater clamping force, or purchase, in the soft tissue. In at least one embodiment, anvil 346 can include compression surface 350 which can be configured to contact soft tissue 360 as described above. In various embodiments, compression surface 350 can include anvil pockets 348 defined therein which can be configured to receive and deform ends 336 of deformable members 306 and 308 such that staples 302 can capture soft tissue 360 therein. In at least one embodiment, however, soft tissue 360 can flow into anvil pockets 348 thereby allowing the soft tissue to expand before the staples are inserted therein. As a result, the soft tissue may be thicker in the areas underlying pockets 348, and, correspondingly, the soft tissue surrounding deformable members 306 and 308, which can reduce the clamping force or purchase of the staples in the soft tissue.

Figure 77:
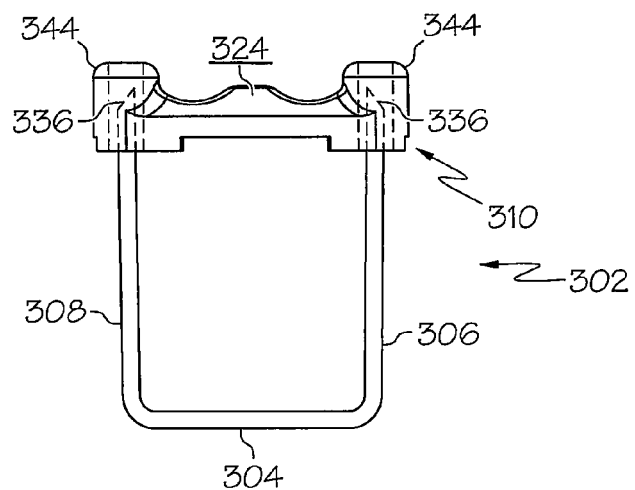
FIG. 77 is an elevational view of a staple having a slidable crown and projections extending therefrom in accordance with one non-limiting embodiment of the present invention.
Figure 78:
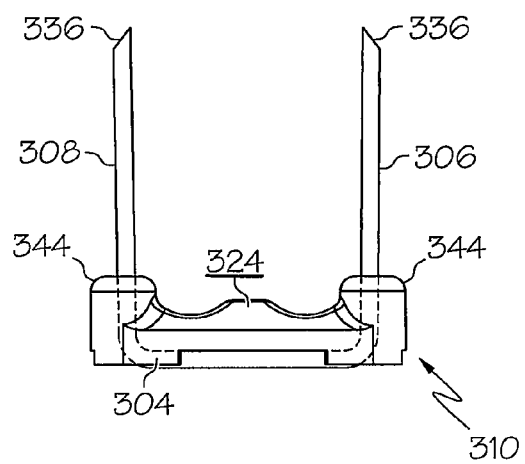
FIG. 78 is an elevational view of the staple of FIG. 77 in a deployed position.
Figure 79:
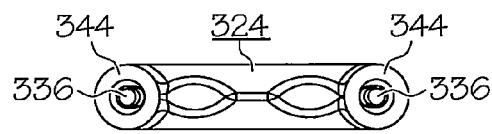
FIG. 79 is a top view of the staple of FIG. 77.
Figure 80:
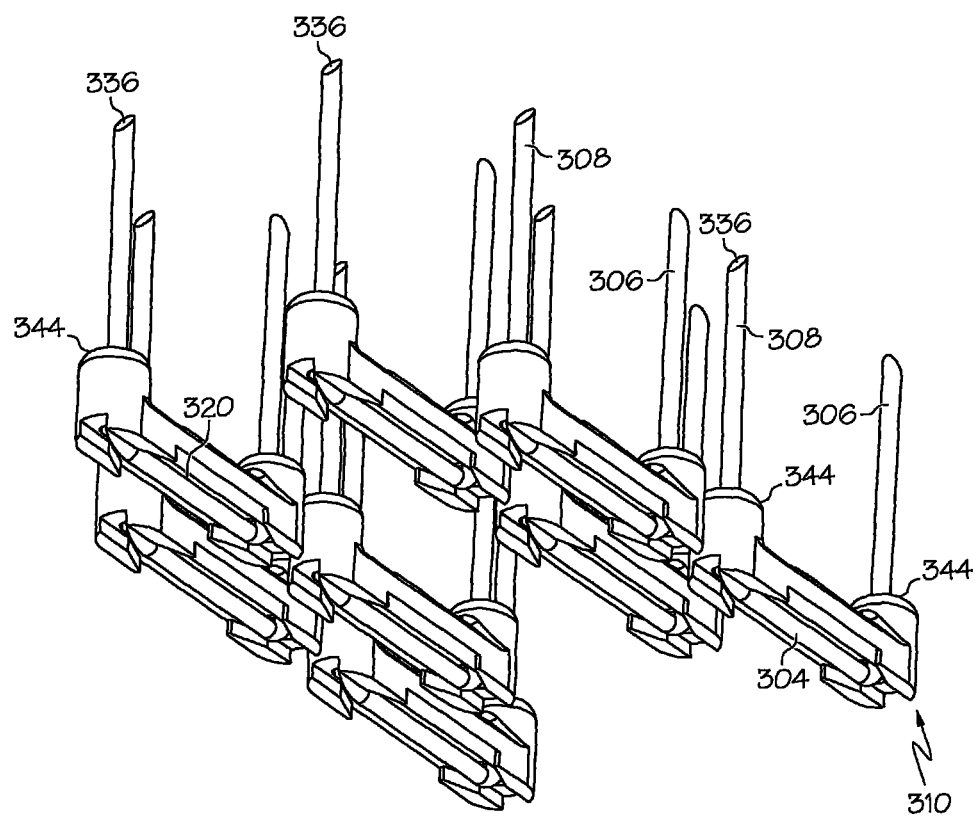
FIG. 80 is a perspective view of several assemblies of the surgical staples of FIG. 77 connected by bridges in accordance with one non-limiting embodiment of the present invention.
Figure 81:
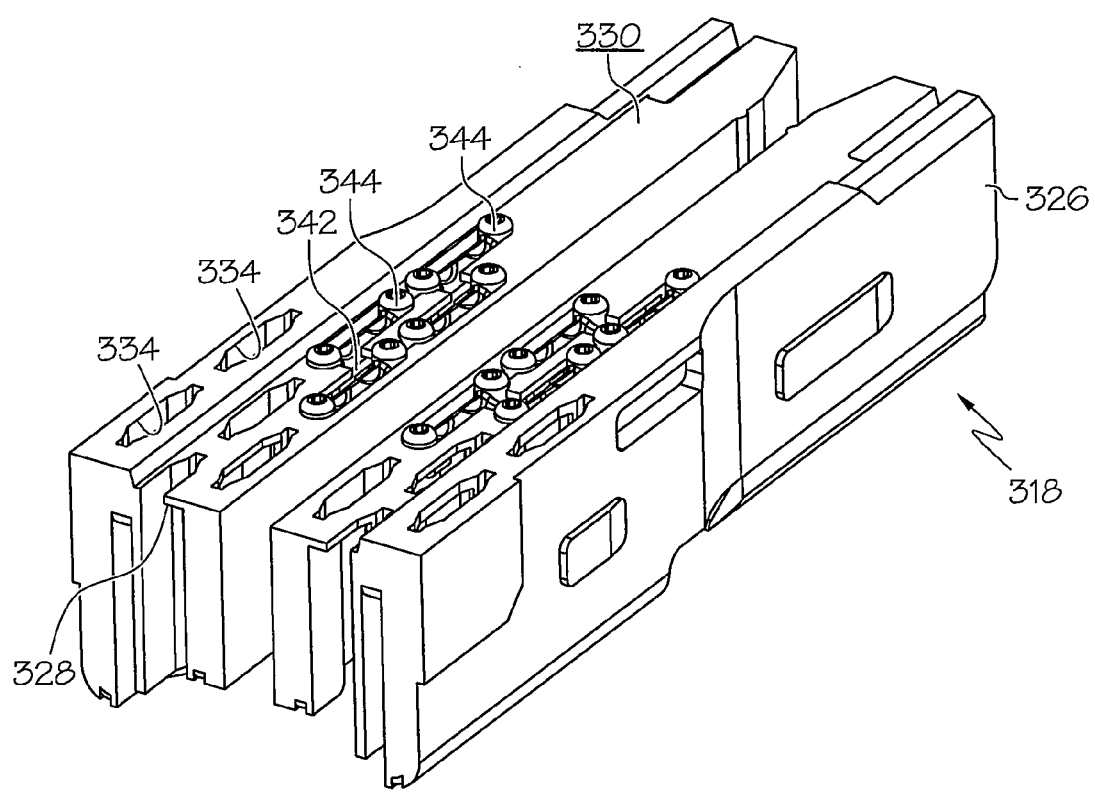
FIG. 81 is a partial perspective view of the assemblies of FIG. 80 positioned within a staple cartridge in accordance with one non-limiting embodiment of the present invention.
Figure 82:
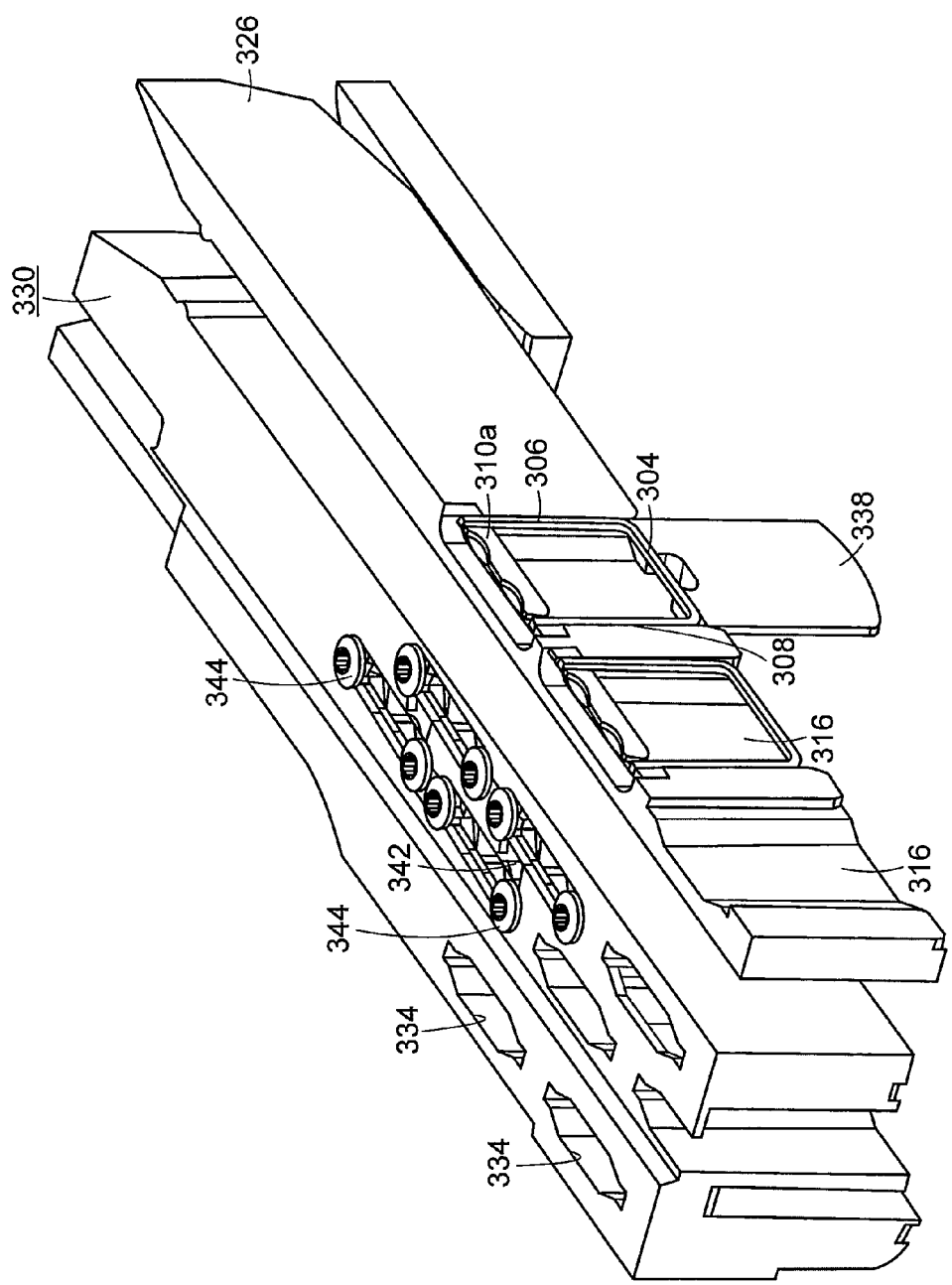
FIG. 82 is a perspective cross-sectional view of the staple cartridge of FIG. 81 with the staple assemblies in an undeployed position.
Figure 83:
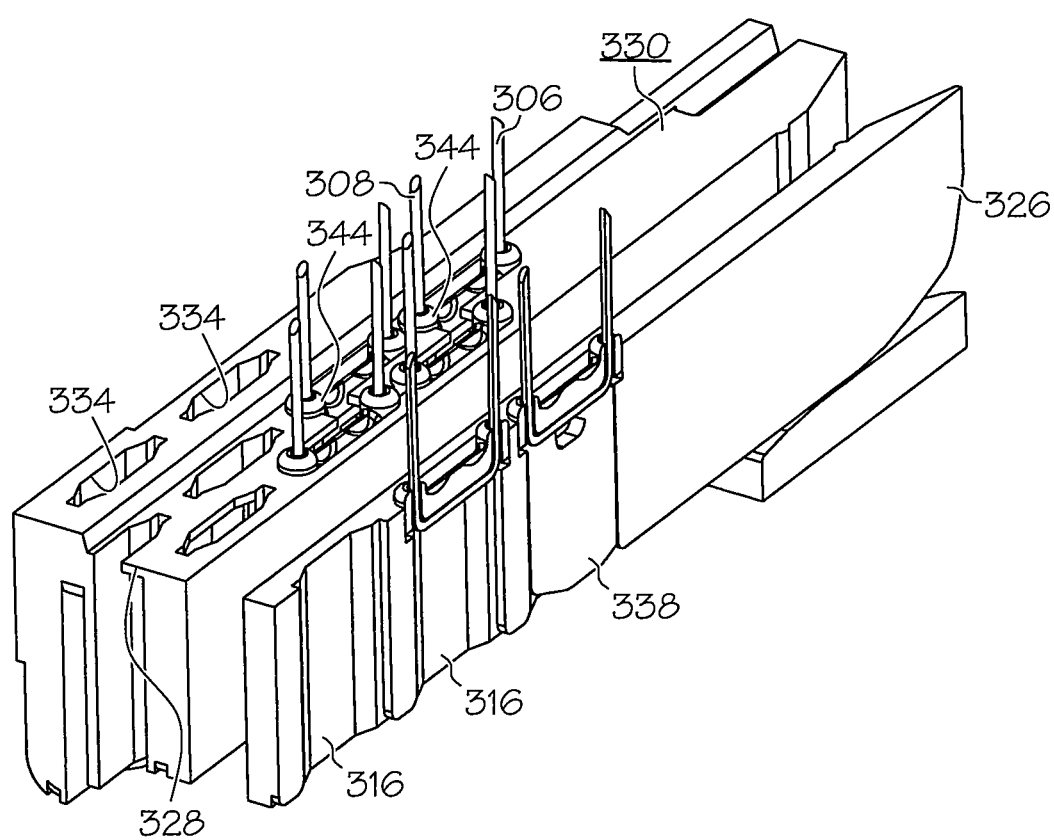
FIG. 83 is a perspective cross-sectional view of the staple cartridge of FIG. 81 with the staple assemblies in a deployed position.

In various embodiments, the surgical staples, for example, can include features which can inhibit, or even prevent, this phenomenon from occurring. More particularly, referring to FIGS. 77-79, staples 302 can include projections 344 extending from crown 310 which can cooperate with anvil pockets 348 to determine the pressure of the soft tissue positioned therebetween. In at least one embodiment, projections 344 can be configured such that the distance between projections 344 and anvil pockets 348 is substantially the same distance as the distance between tissue contacting surfaces 324 of crowns 310 and tissue compression surface 350 of anvil 346. In these embodiments, as a result, the force, or pressure, applied to the soft tissue can be substantially uniform before staples 302 are deployed therein. In other various embodiments, the distance between projections 344 and anvil pockets 348 can be smaller than the distance between staple surfaces 324 and anvil compression surface 350. In such embodiments, the force, or pressure, applied to the soft tissue can be greater in the areas of the soft tissue surrounding deformable members 306 and 308. In at least one embodiment, as a result, a greater amount of blood, or fluids, can be removed from the soft tissue surrounding deformable members 306 and 308 and a greater clamping force or pressure can be generated by staples 302. In various embodiments, projections 344 can also cooperate with anvil pockets 348 to reduce bleeding from the soft tissue at puncture holes created in the soft tissue by deformable members 306 and 308. In such embodiments, projections 344 can essentially act as a clamp and can ameliorate problems associated with bleeding from the soft tissue surrounding the puncture holes.

In various embodiments, as described above, projections 344 can be located adjacent to deformable members 306 and 308, however, other embodiments are envisioned in which one or more projections can be utilized in any suitable location on the staple to control the force, or pressure, applied to the soft tissue. In at least one embodiment, projections 344 can be integrally formed with crown 310a during an injection molding process, for example, and/or projections 344 can be assembled to staples 302. In either event, projections 344 can be comprised of the same material as, or a different material than, the material comprising crown 310. While projections 344 have been described and illustrated as being generally semicircular portions, projections 344 can include any other suitable shape that can compress tissue within anvil pockets 348, for example. In various embodiments, although not illustrated, projections 344, or any other suitable projections, can extend from deck 328 of staple cartridge 318 and/or deformable members 306 and 308.

Figure 85:
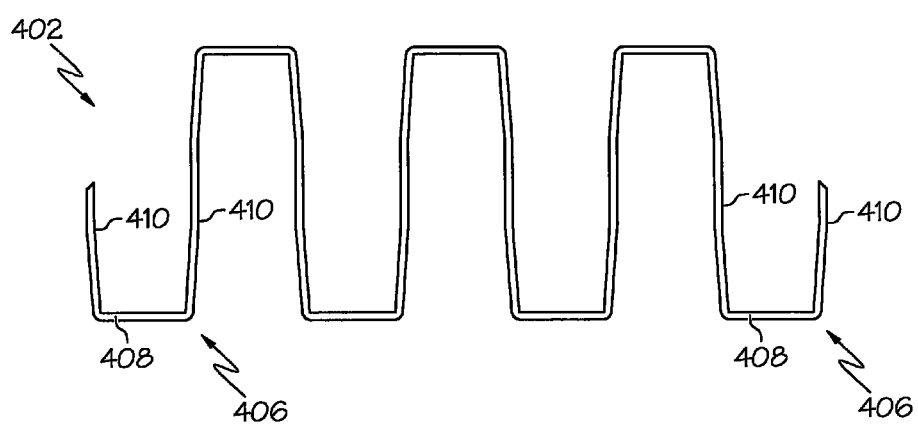
FIG. 85 is a plan view of an elongate member used to form staples in accordance with one non-limiting embodiment of the present invention.
Figure 86:
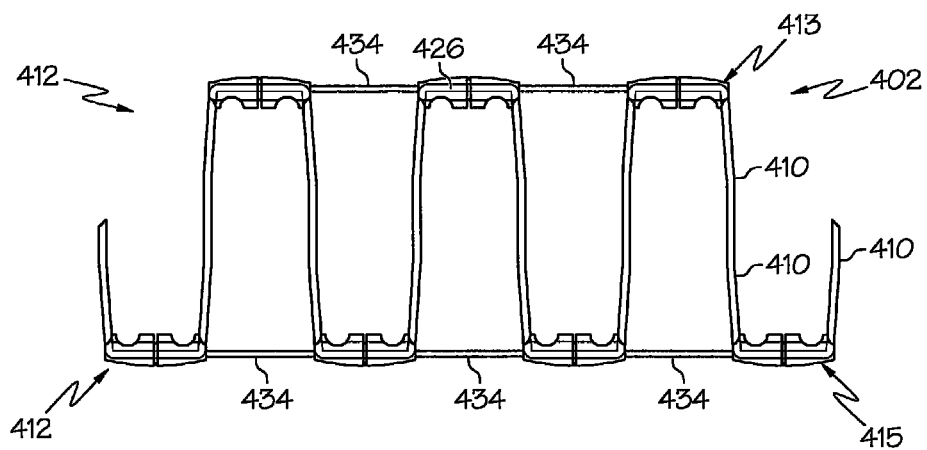
FIG. 86 is a plan view of the elongate member of FIG. 85 illustrating crowns overmolded onto the bases of the staples having connection segments interconnecting the crowns.

In various embodiments of the present invention, surgical staples can be produced by an injection molding process. In at least one embodiment, referring to FIGS. 85-88 and 105, elongate member 402 may be placed into a mold. In various embodiments, elongate member 402 can be placed directly into the mold or, alternatively, referring to FIG. 105, elongate member 402 can be placed into transfer block 404 and then transfer block 404 can then be placed into the mold as described in greater detail below. In either event, referring to FIG. 85, elongate member 402 can comprise a plurality of deformable members 406 where each deformable member 406 can include a base 408 and at least one leg 410.

In various embodiments, elongate member 402 may be comprised of any suitable material such as plastic, titanium, or any other suitable metal. In at least one embodiment, referring to FIG. 85, elongate member 402 can be comprised of a wire and can have a generally serpentine shape. In various embodiments, the term "serpentine shape" can include any non-linear shape which can allow the elongate member to be separated into two staple portions. In at least one embodiment, elongate member 402 can be formed into a generally serpentine shape before and/or during the placement of elongate 402 into the mold or transfer block 404. Further to the above, elongate member 402 can have a cross sectional-shape comprising any of the shapes discussed above or any other cross sectional-shape suitable for making staples.

Figure 105:
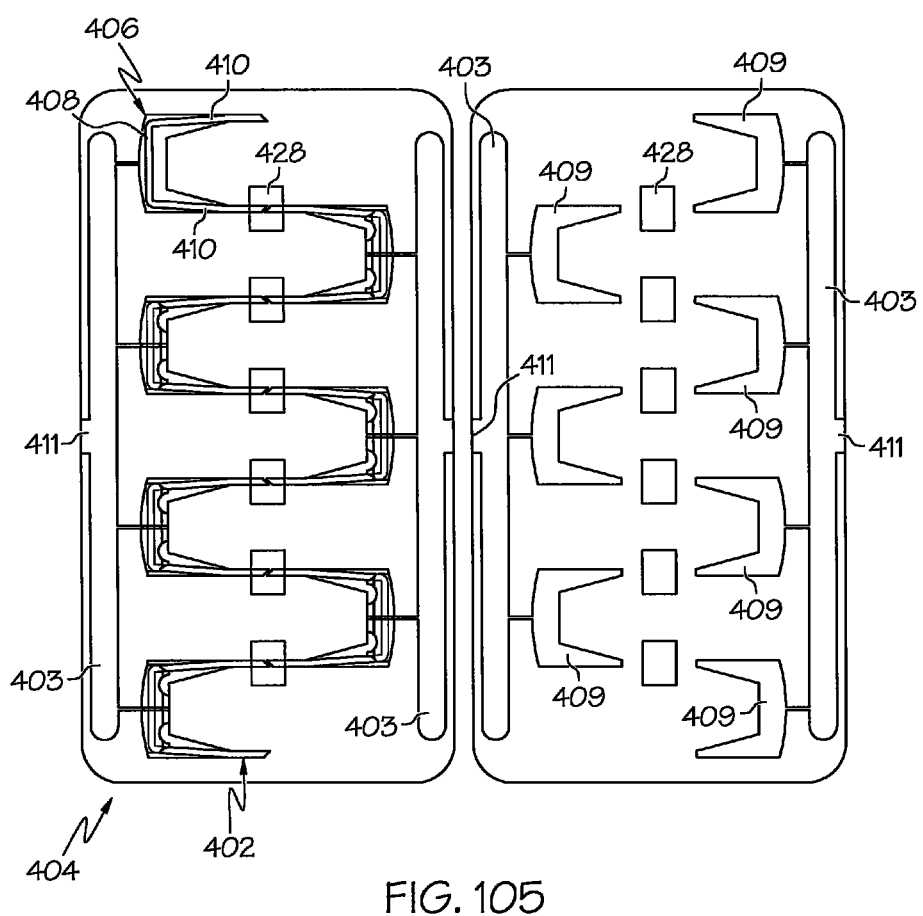
FIG. 105 is a plan view of an alternate transfer block in accordance with one non-limiting embodiment of the present invention.

In various embodiments, referring to FIG. 105, elongate member 402 can be placed in the mold or transfer block 404 such that the bases 408 of deformable members 406 can be situated in a plurality of pre-defined cavities 409. In at least one embodiment, the mold can be closed such that molten material can then be injected into sprue cavities 411 and flow into runner cavities 403 in order to fill cavities 409 with the molten material and at least partially encapsulate bases 408, for example. In various embodiments, the molten material can include a plastic, a metal, and/or any other suitable material. Once cavities 409 have been filled with the molten material, the flow of molten material may cease and, referring to FIG. 86, the molten material can then harden to form overmolded crowns 426. In various embodiments, crowns 426 may have the shape of cavities 409 and, in at least one embodiment, crowns 426 can also be formed onto at least a portion of legs 410. Thereafter, in various embodiments, elongate member 402 can comprise staple strips 412 which may be joined together by connection segments 434 and legs 410 of first staples 413 and second staples 415.

Figure 87:
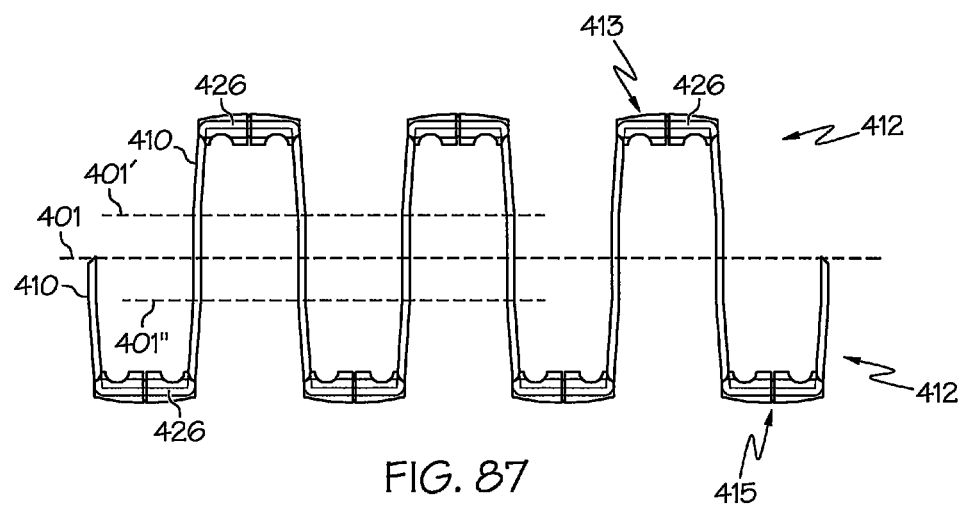
FIG. 87 is a plan view of the elongate member of FIG. 85 illustrating the connection segments removed.
Figure 88:
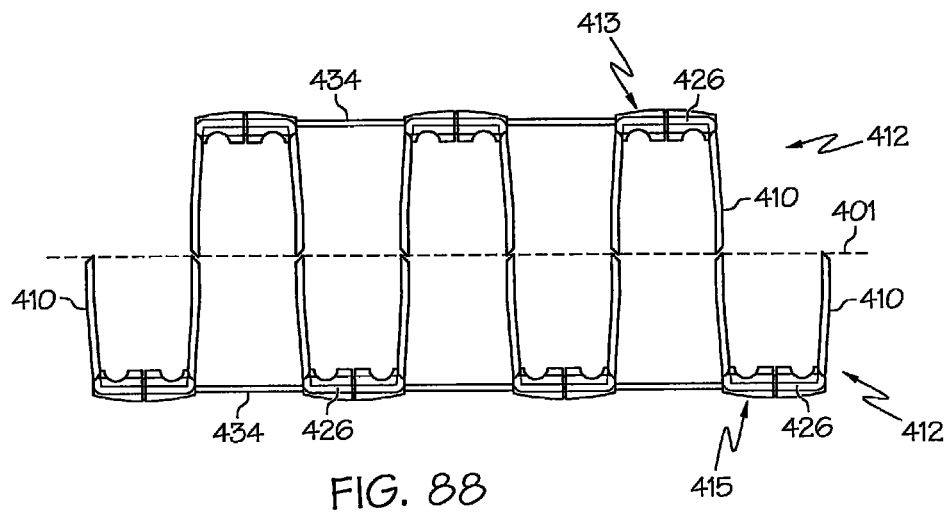
FIG. 88 is a plan view of the elongate member of FIG. 86 that has been cut along an axis.

In various embodiments, as mentioned above, each staple strip 412 can include connection segments 434 as a result of the molding process. More particularly, the mold or transfer block 404 can include runner cavities 403 which can place cavities 409, for example, in fluid communication with each other. Such runner cavities 403 can be useful for assuring that each cavity 409 is filled with molten material and, owing to the molten material that hardens in runner cavities 403, connection segments 434 can extend between crowns 426 of first and second staples 413 and 415, for example. Referring to FIG. 87, in various embodiments, connection segments 434 may be removed from first staples 413 and second staples 415. In at least one embodiment, the connection segments 434 can be removed from the staples by a cutting mechanism or hot knife, for example, operably engaged with the mold and/or transfer block 404. In other embodiments, connection segments 434 can be removed from staples 413 and 415 after staple strips 412 have been removed from the mold and/or transfer block 404. In other various embodiments, connection segments 434 can remain connected to staples 413 and 415 when staple strips 412 are loaded into a staple cartridge and, in various embodiments, connection segments 434 can be removed from, or remain connected to, staple strips 412 after they are deployed from the staple cartridge.

After, before, or contemporaneous with the removal of connection segments 434, staple strips 412 can be cut in order to separate first staples 413 from second staples 415. In various embodiments, referring to FIG. 88, staple legs 410 can be cut along line 401 such that staple legs 410 are substantially the same length. In alternative embodiments, referring to FIG. 87, staple legs 410 can be cut along lines 401' and/or 401", for example, such that staple legs 410 are different lengths. In various embodiments, staples having shorter legs can provide a different compression force, or pressure, to soft tissue captured therein, for example, than staples having longer legs. In such embodiments, legs 410 can be cut to a desired length such that they can apply a desired compression force, or pressure, to the soft tissue. In either event, in various embodiments where connection segments 434 have not yet been removed, referring to FIG. 88, legs 410 of first staples 413 can be separated from legs 410 of second staples 415 in order to separate staple strips 412. Although staple strips 412 are illustrated as substantially linear staple strips, staple strips 412 can form a circular ring of staples or any other suitable configuration. In embodiments where connection segments 434 have already been removed, referring to FIG. 87, the cutting process can separate first staples 413 from second staples 415.

In various embodiments, referring to FIG. 105, the cutting process may occur through the use of transfer block 404 when elongate member 402 has been positioned therein. More particularly, transfer block 404 can include a plurality of slots 428 which can be configured to receive a cutting member (not illustrated) where the cutting member can sever legs 410 as described above. In at least one embodiment, the cutting member can be configured to sever legs 410 at any suitable location within slots 428 such that staple legs 410 can be cut to a suitable length. In various embodiments, first staple 413 can be cut such that it has shorter legs 410 than second staple 415, for example. In other various embodiments, the cutting member can also sever legs 410 at more than one location within slot 428. In such embodiments, the transfer block 404 can remain closed and hold staple strips 412 in place while legs 410 are being separated. In other embodiments, the cutting step may occur after the mold or transfer block 404 is opened. In various embodiments, the cutting step can be performed after transfer block 404 has been removed from the mold such that the cutting step can be performed at a cutting station, by hand or by any other suitable cutting method.

In various embodiments, the method of making staples can include an automated process. In at least one embodiment, the automated process can include a wire forming machine which can bend wire to form elongate members 402. The automated process can further include transfer block 404 which can be positioned on a rotary table or conveyor and can be configured to receive elongate members 402. In various embodiments, the automated process can further include a robotic arm or other transfer mechanism for positioning one or more elongate members 402 within transfer block 404. Thereafter, the automated process can utilize a shuttle mechanism, for example, for moving transfer block 404 into the mold where the molten material can be injected therein. In various embodiments, the shuttle mechanism, for example, can remove transfer block 404 from the mold such that transfer block 404 can be moved to a cutting station as described above to cut elongate member 402 and/or connection segments 434. In other embodiments, as outlined above, this cutting step can occur while transfer block 404 is positioned within the mold. In either event, transfer block 404 can be opened and staple strips 412 and/or the singulated staples 413 and 415 can be removed and the automated process can be repeated.

Figure 89:
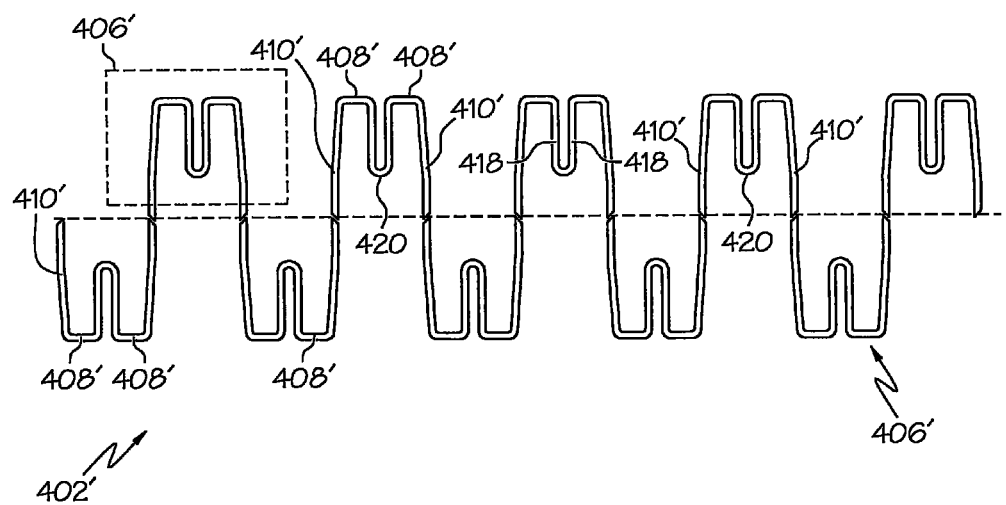
FIG. 89 is a plan view of an alternate elongate member in accordance with one non-limiting embodiment of the present invention.
Figure 90:
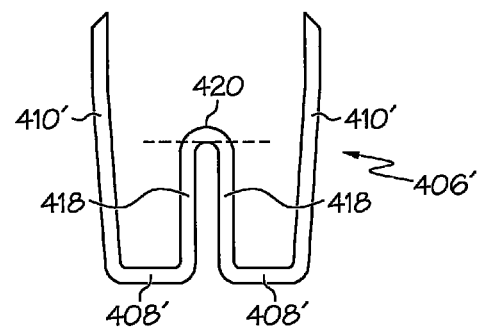
FIG. 90 is a plan view of a deformable member that has been singulated from the elongate member of FIG. 89 in accordance with one non-limiting embodiment of the present invention.
Figure 91:
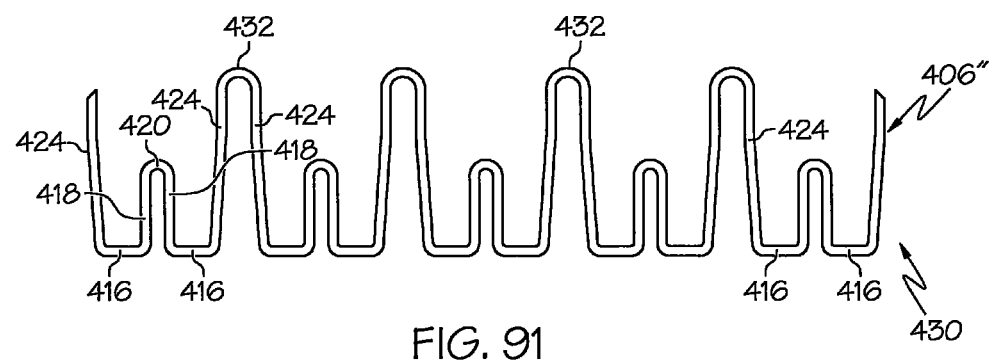
FIG. 91 is a plan view of another alternate elongate member in accordance with one non-limiting embodiment of the present invention.
Figure 92:
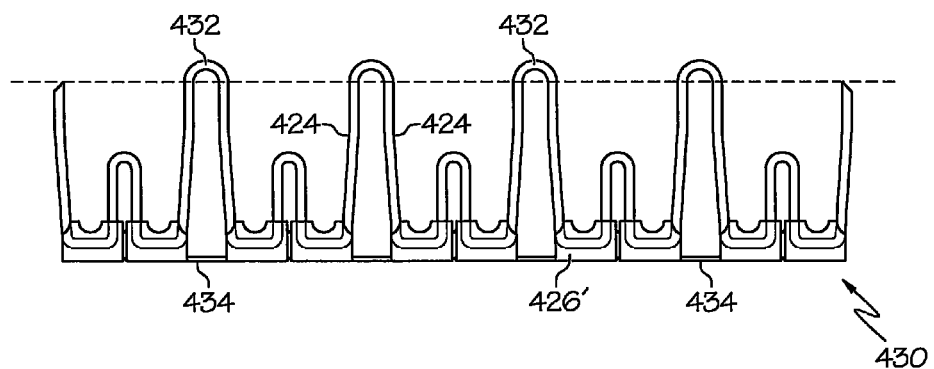
FIG. 92 is a plan view of the alternate elongate member of FIG. 91 illustrating crowns overmolded on to the bases of the staples in accordance with one non-limiting embodiment of the present invention.
Figure 93:
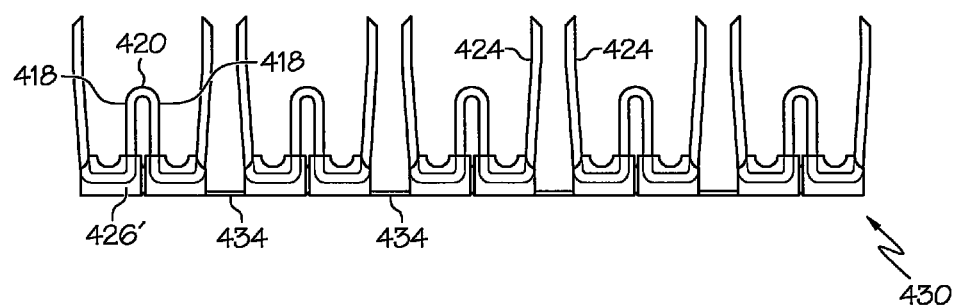
FIG. 93 is a plan view of the elongate member of FIG. 92 after the elongate member has been cut along an axis.
Figure 94:
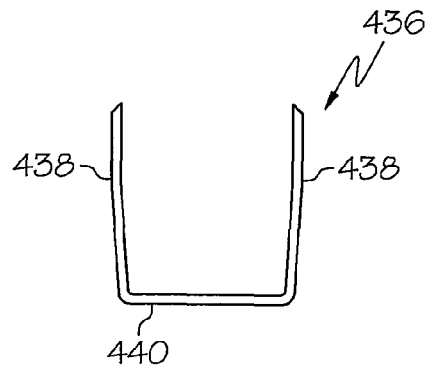
FIGS. 94-99 are plan views of various alternate deformable members in accordance with non-limiting embodiments of the present invention.
Figure 95:
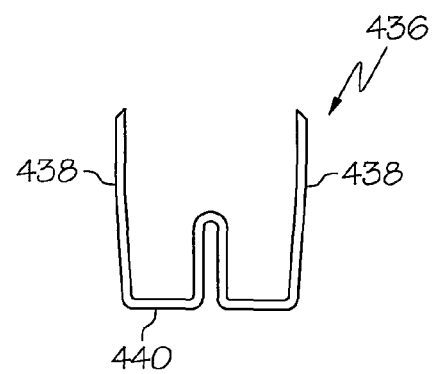
Figure 96:
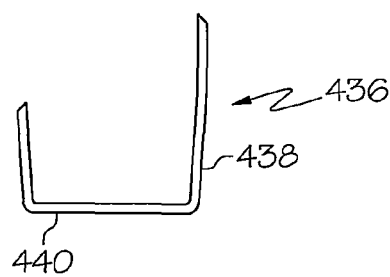
Figure 97:
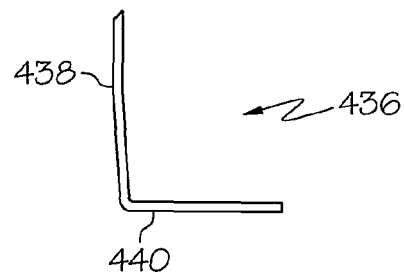
Figure 98:
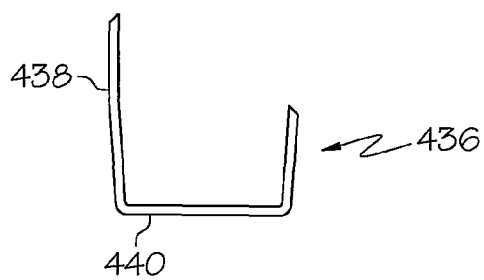
Figure 99:
Figure 100:
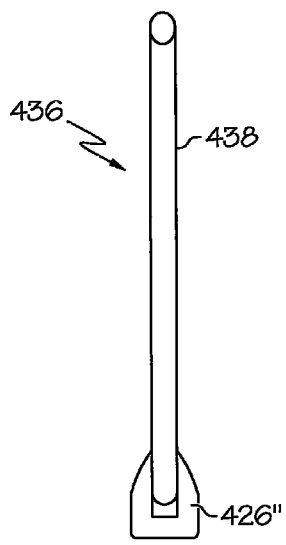
FIG. 100 is a side view of a singulated staple manufactured from the elongate member of FIG. 85 in accordance with one non-limiting embodiment of the present invention.
Figure 101:
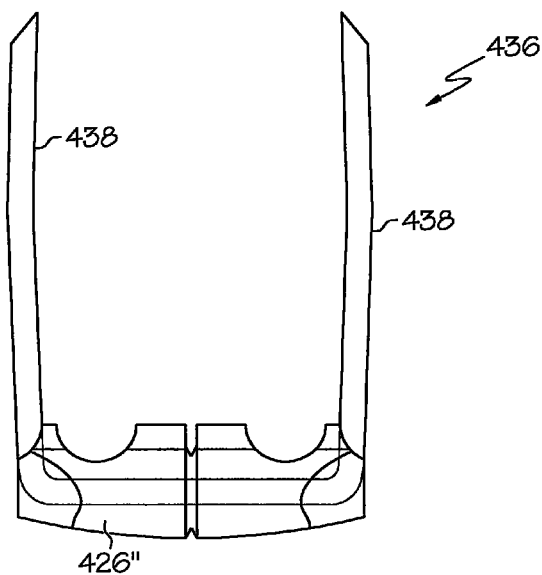
FIG. 101 is an elevational view of the staple of FIG. 100.
Figure 102:
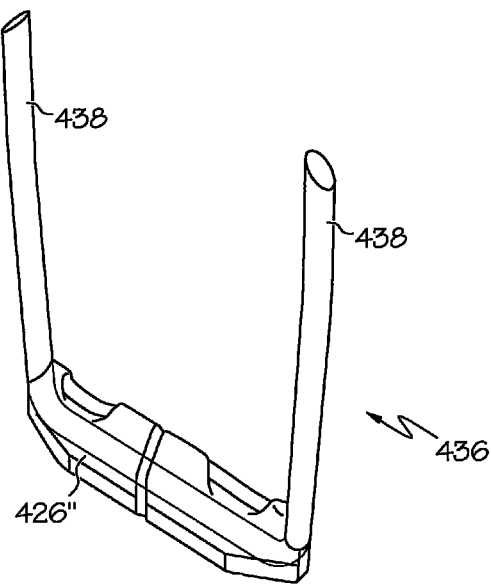
FIG. 102 is a perspective view of the staple of FIG. 100.
Figure 103:
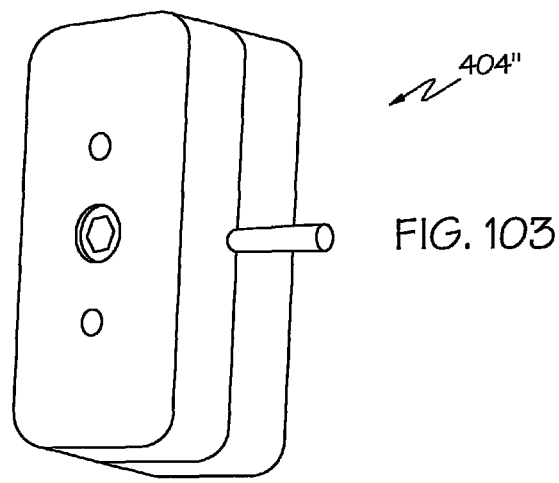
FIG. 103 is a perspective view of a transfer block in a closed configuration for molding a plurality of individual staples in accordance with one non-limiting embodiment of the present invention.
Figure 104:
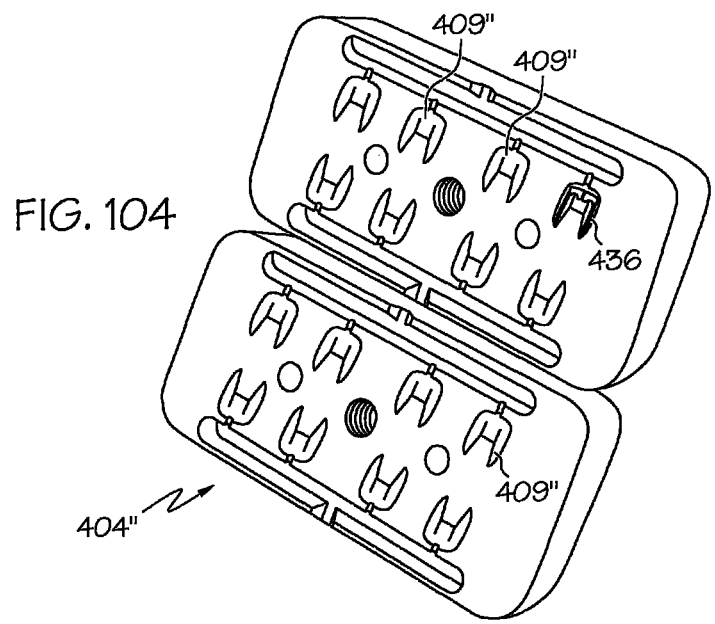
FIG. 104 is a perspective view the transfer block of FIG. 103 in an open configuration for molding a plurality of individual staples in accordance with one non-limiting embodiment of the present invention.
Figure 106:
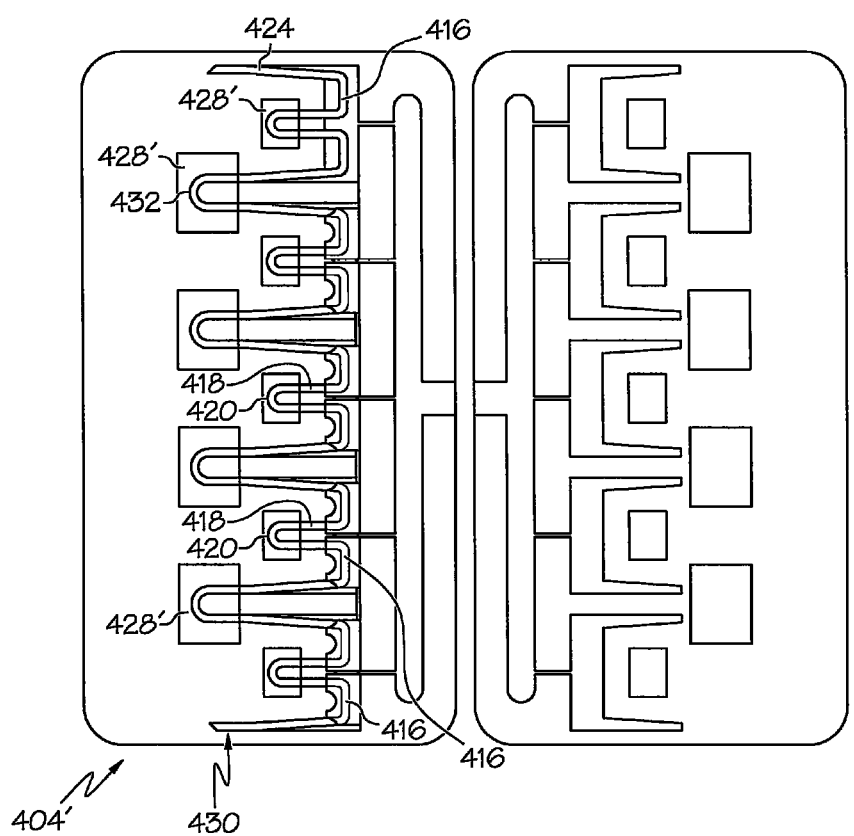
FIG. 106 is a plan view of another alternate transfer block in accordance with one non-limiting embodiment of the present invention.
Figure 107:
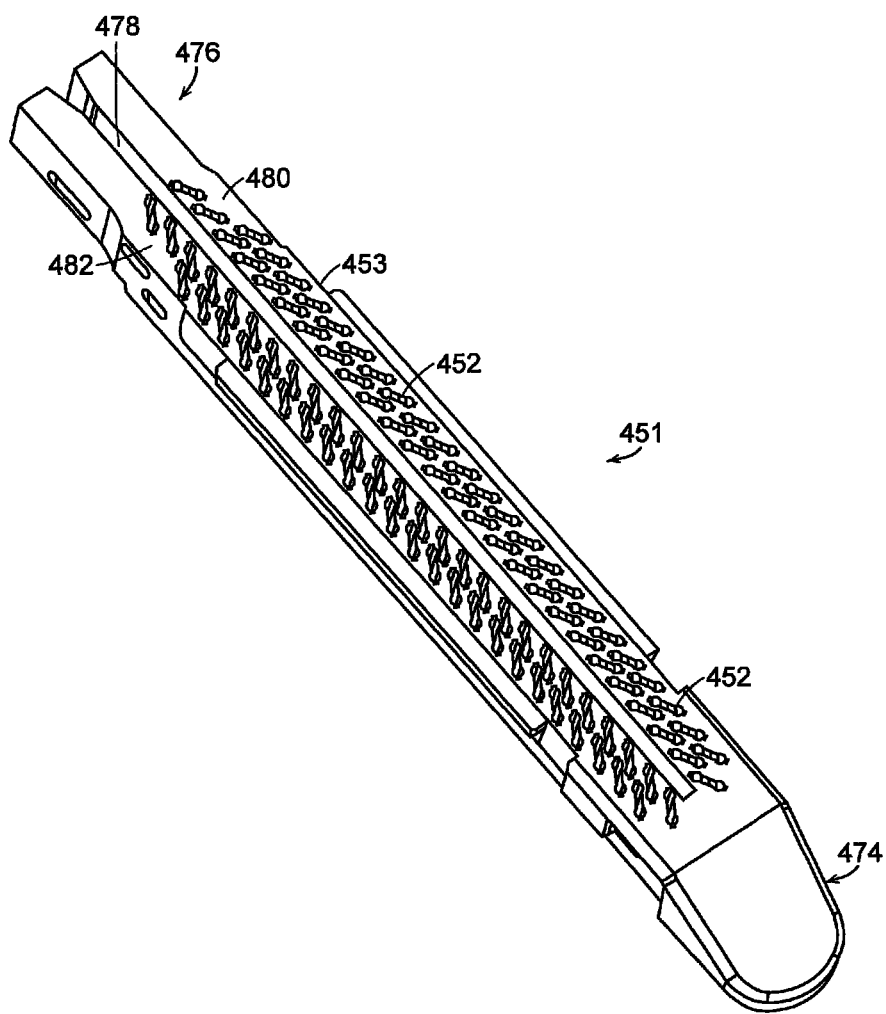
FIG. 107 is a perspective view of a staple cartridge in accordance with one non-limiting embodiment of the present invention.
Figure 108:
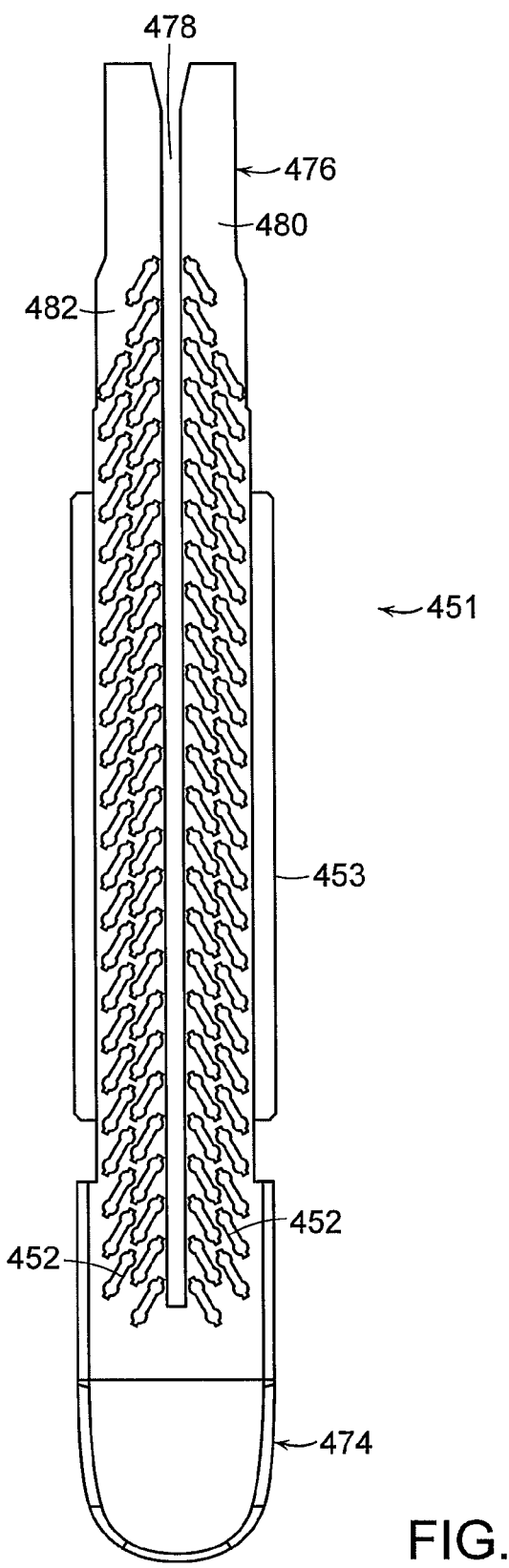
FIG. 108 is a top view of the staple cartridge of FIG. 107.
Figure 109:
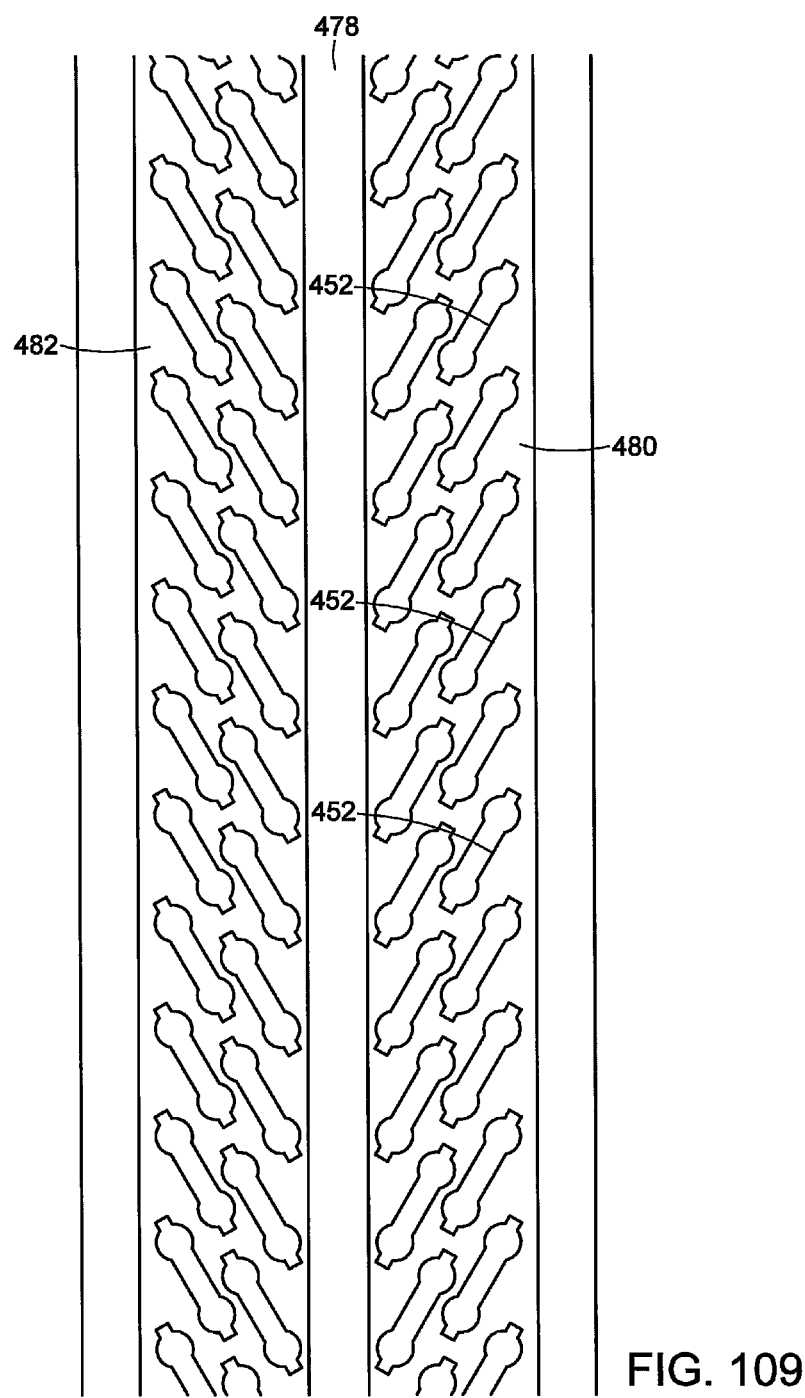
FIG. 109 is a detail view of the staple cartridge of FIG. 107.

In other various embodiments, referring to FIG. 89, the deformable members 406' of elongate member 402' can each include two bases 408', two legs 410', and intermediate portion 420 which can connect bases 408'. In at least one embodiment, referring to FIG. 90, intermediate portion 420 can be severed to create two middle legs 418. In other various embodiments, referring to FIGS. 91-93, deformable members 406" of elongate member 430 can be arranged such that the staples are positioned in a side-by-side configuration and joined by connector 432. In such embodiments, each staple can have two deformable legs 424, two bases 416 and, in at least one embodiment, intermediate portion 420 can be separated to create two middle legs 418 as described above. In at least one such embodiment, referring to FIG. 106, elongate member 430 can be positioned within a transfer block 404', for example, such that crown 426', referring to FIG. 92, can be molded onto bases 416. In at least one various embodiment, transfer block 404' can include apertures or slots 428' through which a cutting member can be operably engaged to separate connector 432 from legs 424. In various embodiments, similar to the above, the cutting member can be configured to sever legs 424 at different locations within slot 428' in order to selectively cut staple legs 424 to a desired length.

In other various embodiments, referring to FIGS. 94-104, separate deformable members 436 can be positioned within the mold and/or transfer block 404". In at least one such embodiment, referring to FIG. 94, individual deformable members 436 can include at least one leg 438 and base 440 wherein each base 440 can be positioned within a cavity 409" of the mold or transfer block 404", referring to FIG. 104, to receive crown 426" molded thereon.

In various embodiments of the present invention, as outlined above, surgical staples can be removably stored within a staple cartridge and can be deployed from the staple cartridge by a sled which can be configured to traverse the staple cartridge. In at least one embodiment, as described above, the staple cartridge can further include drivers which can be lifted by the sled and can, correspondingly, deploy the staples from the staple cartridge. In various embodiments, as also described above, the staples can include features which can cooperate directly with the sled such that the staples can be deployed from the staple cartridge without drivers. In either event, the staples can be moved within staple cavities in the staple cartridge as they are deployed and, in various circumstances, the staples may rotate, or tilt, within the staple cavities which can cause the staples to be deployed in an undesired orientation or become stuck within the staple cavities. In various embodiments of the present invention, the staples and/or the staple cartridge cavities can include features which can at least inhibit, if not prevent, unwanted rotation, or tilting, of the staples.

In various embodiments, referring to FIGS. 107-110, staple cartridge 451 can include at least one staple cavity 452 defined therein. In at least one embodiment, referring primarily to FIGS. 109 and 110, staple cavity 452 can include one or more arcuate portions, or sides, 454 which can be configured to cooperate with a surgical staple positioned within the cavity 452 such that the staple does not substantially rotate relative to axis 450. In various embodiments, referring to FIGS. 111 and 112, surgical staple 456 can include crown 462 and at least one leg 460, where crown 462 can include arcuate portions, or sides, 464 which can be configured to cooperate with arcuate portions 454 of staple cavity 452. More particularly, arcuate portions 454 of staple cavity 452 can provide bearing surfaces against which arcuate portions 464 of staple 456 can abut as staple 456 is moved along the z-axis of the cavity, or axis 450, and prevent, or at least inhibit, staple 456 and crown 462 from tilting, or rocking, within cavity 454. In at least one embodiment, arcuate portions 464 of crown 462 can frictionally engage arcuate portions 454 of cavity 452 such that there is a substantially uniform friction force acting on arcuate portions 464 of crown 462. In various circumstances, referring to regions 465 in FIG. 110, for example, arcuate portions 454 can also allow cavities 452 to be positioned in a tightly packed arrangement.

Figure 111:
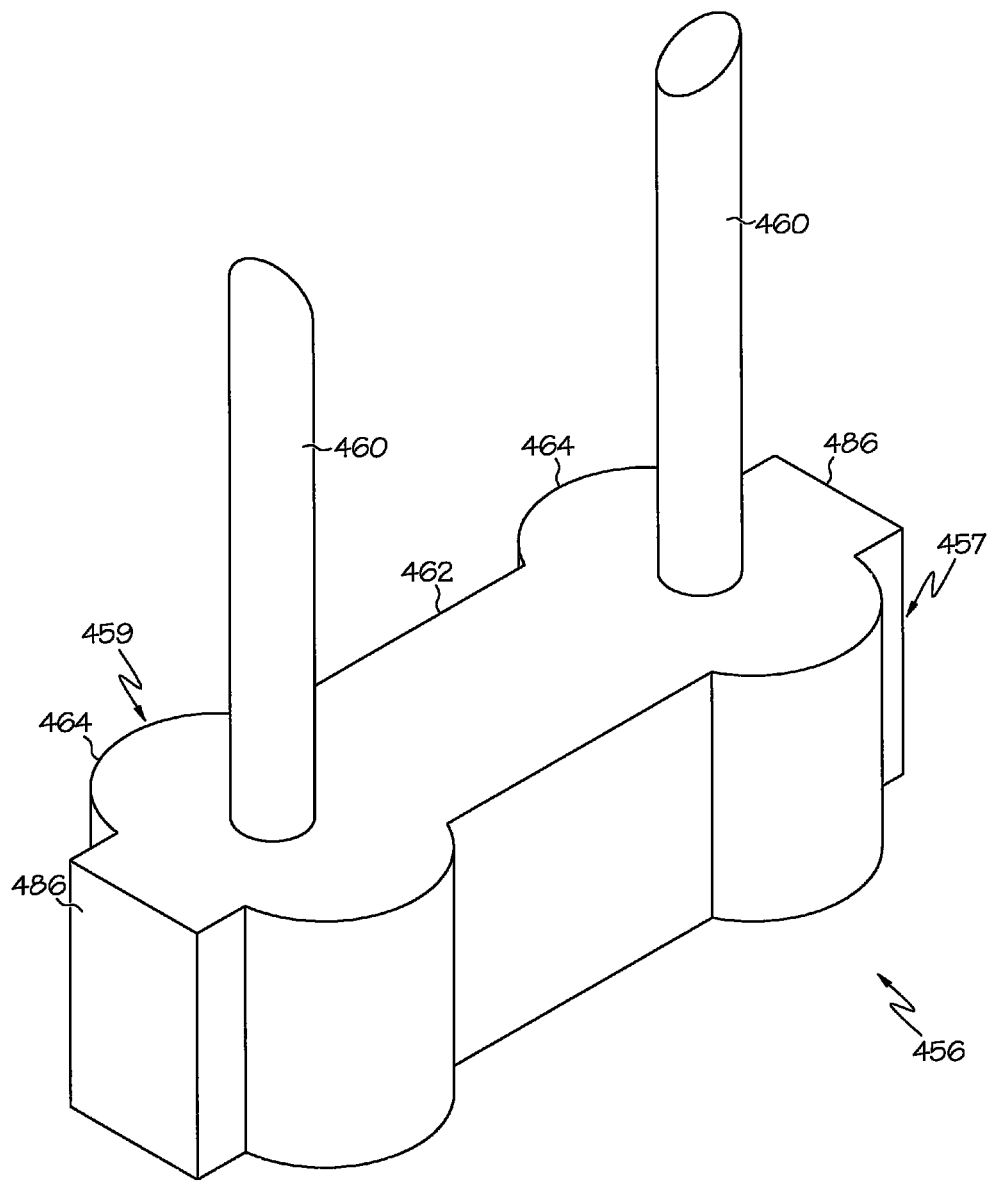
FIG. 111 is a perspective view of a surgical staple configured to be positioned within a staple cavity of the staple cartridge of FIG. 107.
Figure 112:
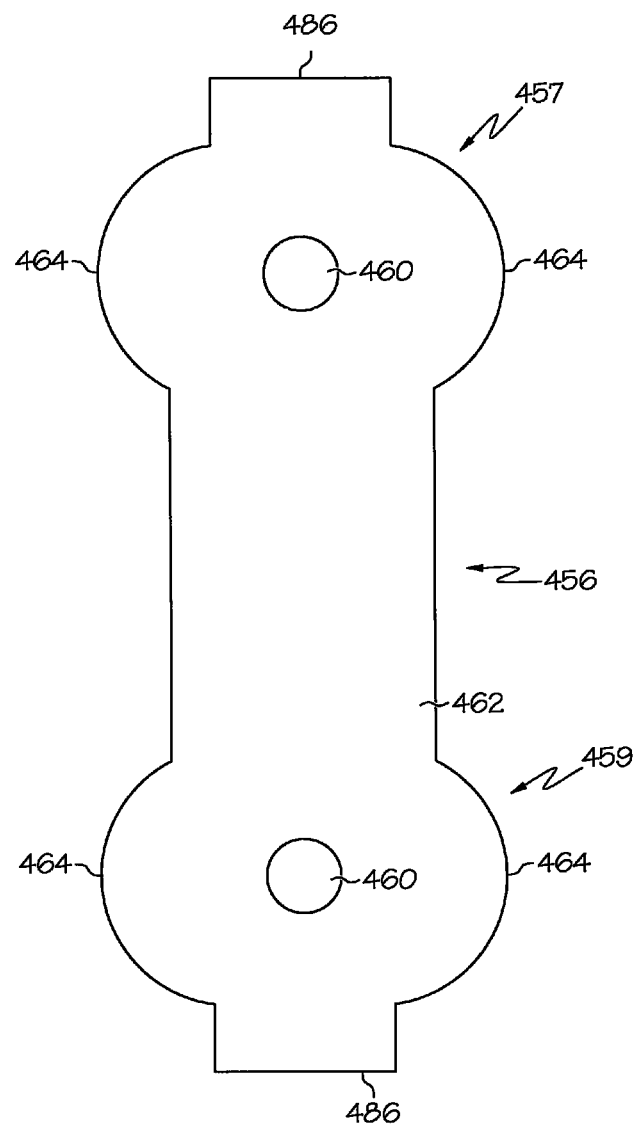
FIG. 112 is a plan view of the surgical staple of FIG. 111.
Figure 113:
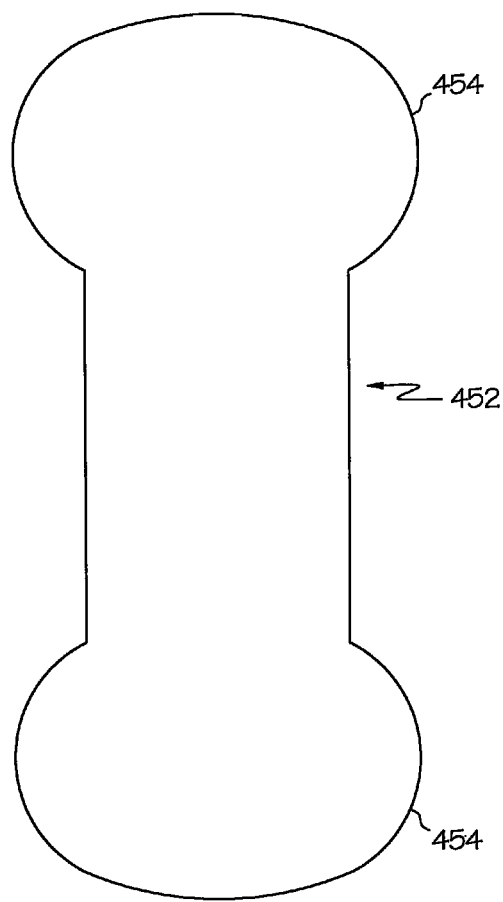
FIG. 113 is a plan view of a staple cavity of a staple cartridge in accordance with one non-limiting embodiment of the present invention.
Figure 116:
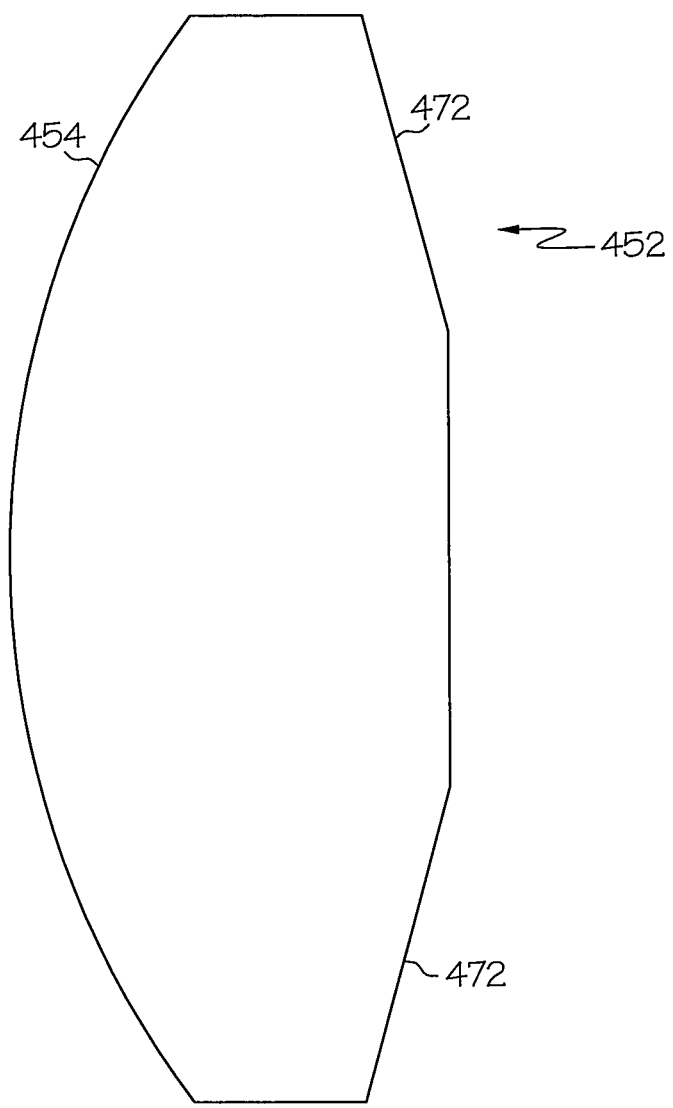
FIG. 116 is a plan view of a staple cavity of a staple cartridge in accordance with one non-limiting embodiment of the present invention.

In various embodiments, referring to FIGS. 111-113, arcuate portions 464 of staple 456 can comprise cylindrical, or at least partially cylindrical, portions where the cylindrical portions can prevent staple 456 from tilting, or rocking, within staple cavity 452. More particularly, the cylindrical portions can cooperate with arcuate portions 454 of staple cavity 452 such that one end of staple 456 does not substantially dip or raise above the other end of staple 456. In at least one embodiment, referring to FIGS. 110-112, staple 456 can include distal end 457 and proximal end 459 and, in addition, staple cavity 452 can include distal end 461 and proximal end 463. In various embodiments, ends 461 and 463 of cavity 452 can be configured to guide crown 462 along axis 450 such that ends 457 and 459 do not substantially tilt, or rock, toward or away from axis 450. In such embodiments, as a result, deformable members 460 can be deformed by an anvil at substantially the same time and can be deformed substantially the same amount to apply substantially the same compressive force to the soft tissue captured in staple 456. In various embodiments, the crown of the surgical staple can include an entirely arcuate side (not illustrated) and the staple cavity, referring to FIG. 116, can include an arcuate side wall 454 which can be configured to cooperate with the arcuate side of the staple as described above.

Figure 110:
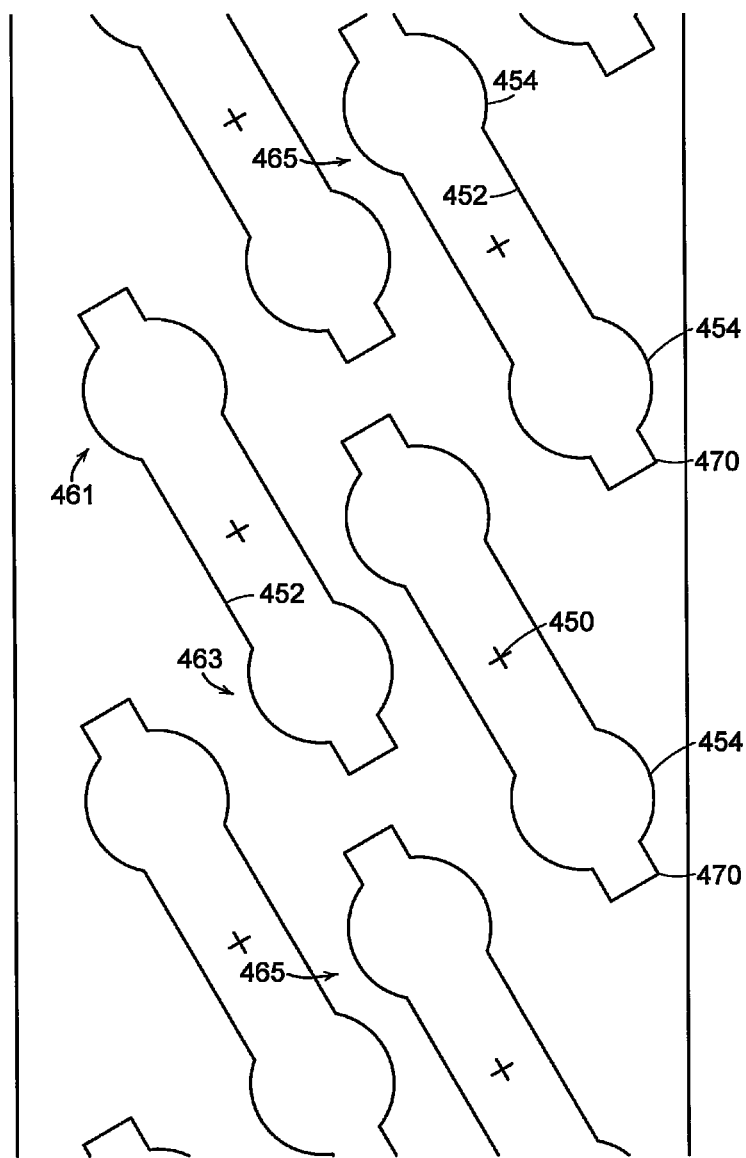
FIG. 110 is an additional detail view of the staple cartridge of FIG. 107.
Figure 110A:
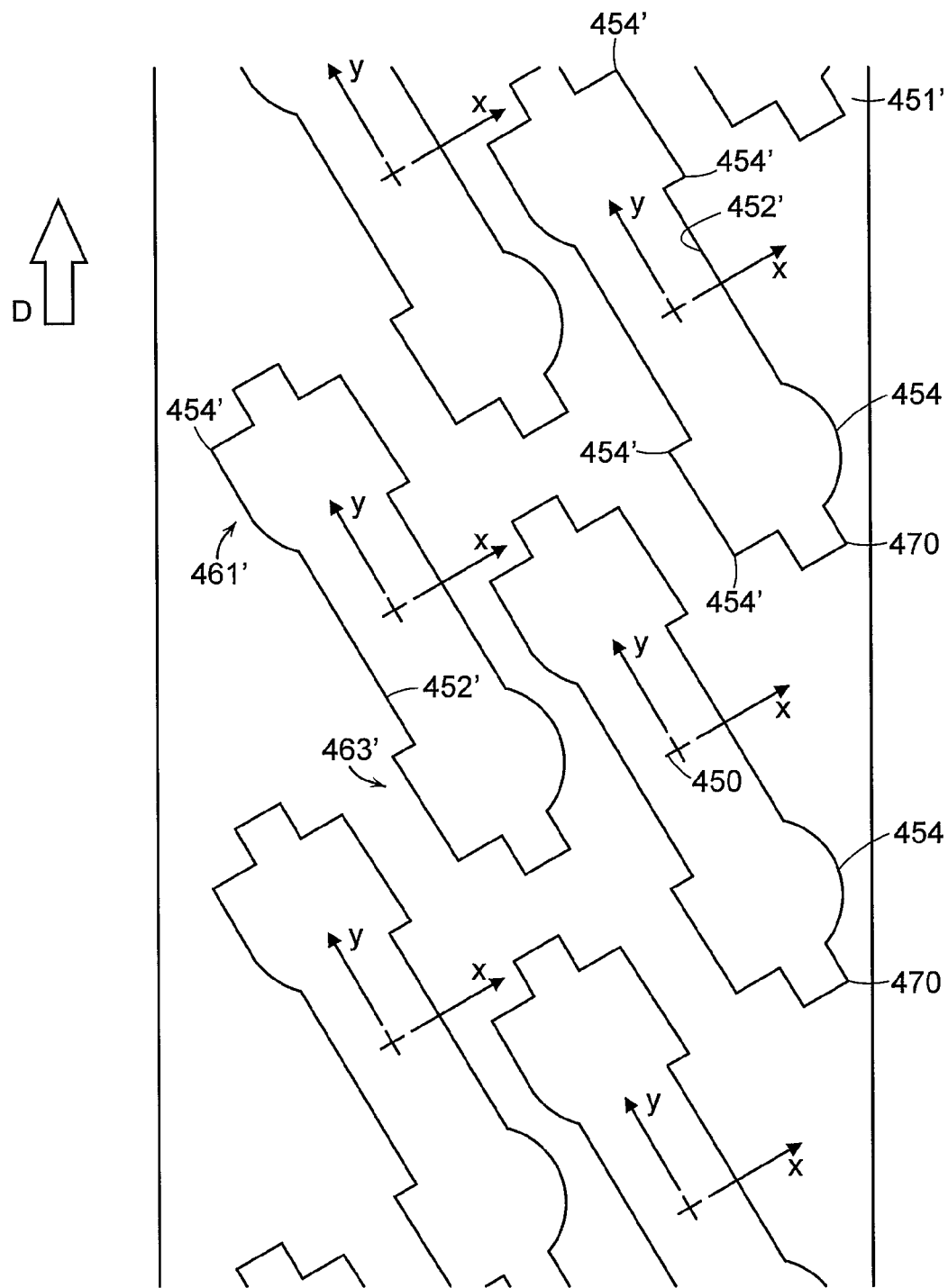
FIG. 110A is a detail view of a staple cartridge in accordance with one non-limiting embodiment of the present invention.
Figure 114:
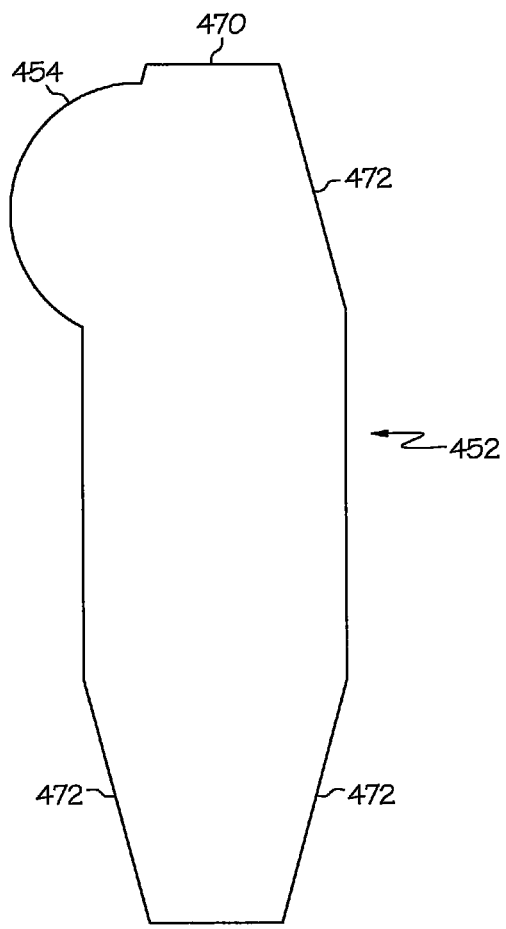
FIG. 114 is a plan view of a staple cavity of a staple cartridge in accordance with one non-limiting embodiment of the present invention.
Figure 115:
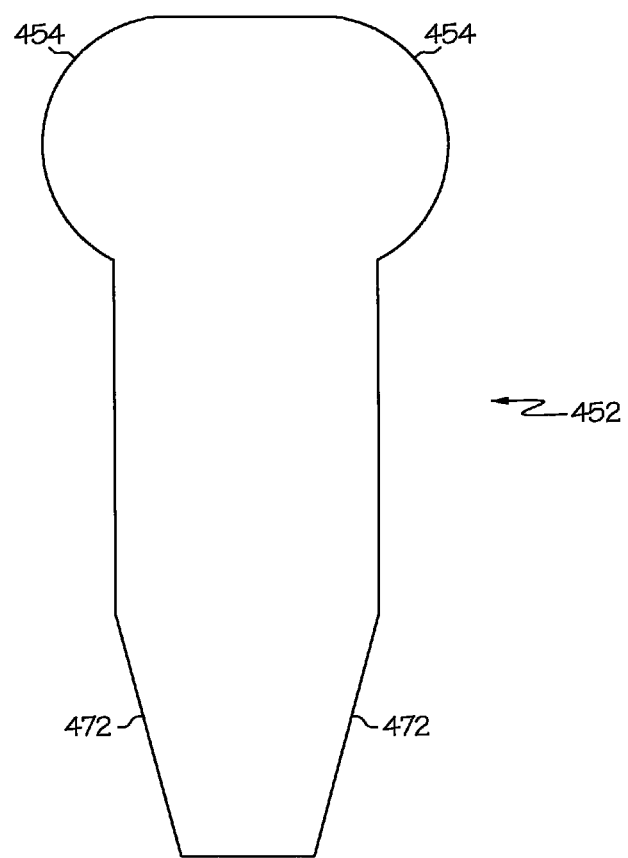
FIG. 115 is a plan view of a staple cavity of a staple cartridge in accordance with one non-limiting embodiment of the present invention.

Although arcuate and cylindrical portions are described above, the present invention is not limited to such configurations. In various embodiments, referring to FIGS. 110-112, staple cavities 454 can include substantially rectangular notches 470 which can be configured to receive projections 486 extending from crown 462. In at least one embodiment, notches 470 and projections 486 can be configured to prevent, or at least inhibit, staples 456 from rotating or tilting within cavities 454 as described above. In various embodiments, referring to FIGS. 114-116, the crown of the surgical staple can include at least one diagonal, or angled, portion (not illustrated) where the staple cavity can include a cooperating diagonal, or angled, portion 472. In various alternative embodiments, referring to FIG. 110A, staple cartridge 451' can include staple cavities 452' where cavities 452' can include one or more square, or at least substantially square, corners 454'. In such embodiments, corners 454' can be configured to cooperate with corresponding square, or substantially square, corners on staples positioned within cavities 452' in order to prevent, or at least limit, relative movement about the x and y axes illustrated in FIG. 110A. In various embodiments, when a staple sled is moved within staple cartridge 451' in a direction illustrated by arrow D, the sled can shift the staples within cavities 452' in direction D causing one or more square corners of the staple to sit flushly within square corners 454'. In these circumstances, the cooperating square features can prevent, or at least resist, the staples from rotating about the x and y axes, for example. Further to the above, the alignment of the square corners can also prevent, or at least inhibit, the staples from becoming wedged, or caught, within staple cavities 452'. In various embodiments, as illustrated in FIG. 110A, staple cavities 452' can include both arcuate and square features and receive at least the benefits of each feature described above.

In various embodiments, referring to FIGS. 107-110, staple cartridge 451 can include staple cartridge body 453 including first end 474 and second end 476. In at least one embodiment, slot 478 can be formed between first end 474 and second end 476 where slot 478 can be configured to accept a cutting member. Further to the above, slot 478 can define first side 480 and second side 482 of staple cartridge body 453 where a plurality of staple cavities 452 can be defined in staple cartridge body 453 on first side 480 and/or on second side 482. In at least one embodiment, cavities 452 on both first side 480 and second side 482 can be transversely situated, or oriented in an acute angle, with respect to slot 478 and, in at least one embodiment, cavities 452 can be substantially parallel to each other.

Figure 117:
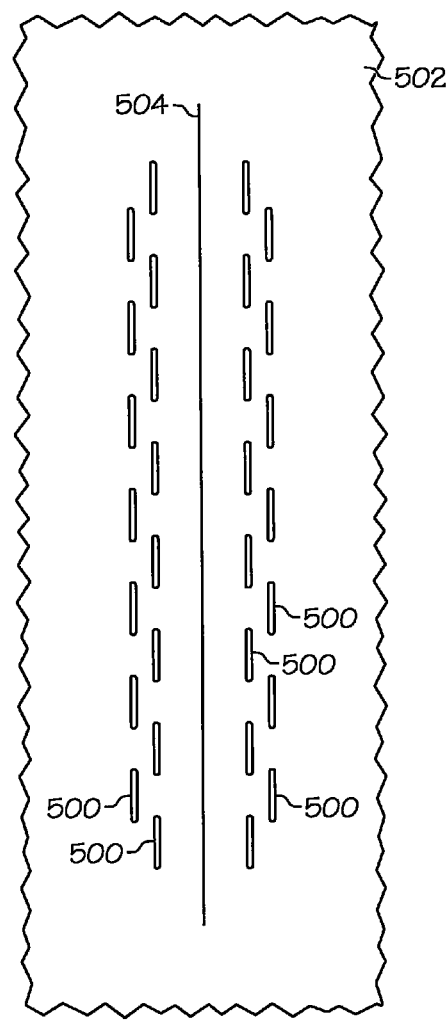
FIG. 117 is a top view of a staple pattern along an incision, the pattern having substantially parallel rows of staples.

In various embodiments, as described above, surgical staplers can be configured to deploy surgical staples in parallel rows on opposite sides of an incision. In such embodiments, referring to FIG. 117, one or more rows of staples 500 can be used to join together or compress soft tissue 502 in order to prevent or reduce bleeding from the soft tissue on both sides of incision 504, for example. In various embodiments, these rows of staples 500 can be off-set, or staggered, relative to each other such that staples 500 can overlap each other and constrict blood vessels in soft tissue 502, especially blood vessels that extend perpendicular, or substantially perpendicular, to incision 504. Although such a staple pattern can be suitable for its intended purpose, improvements can be made thereto, especially in relation to blood vessels which extend in a transverse and/or parallel direction to incision 504.

Figure 118:
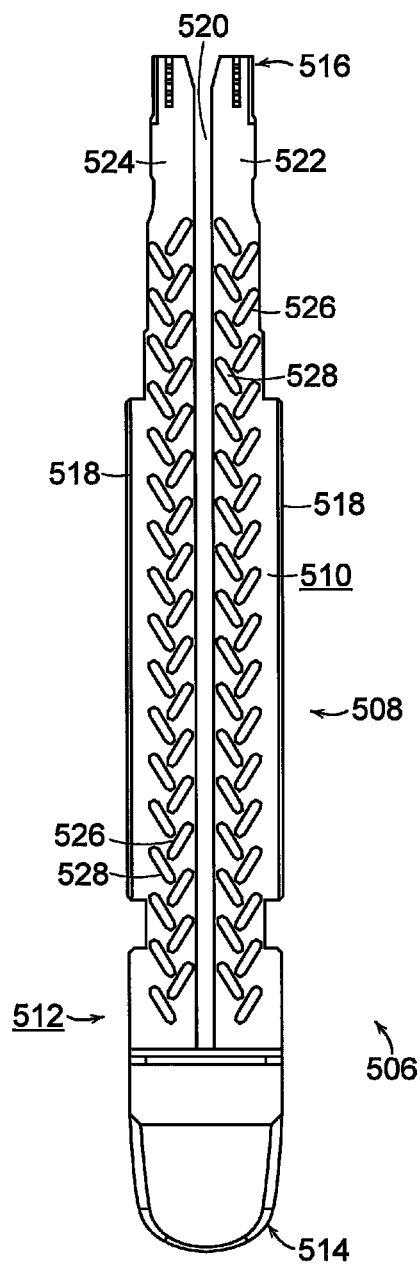
FIG. 118 is a top view of a staple cartridge having a staple pattern in accordance with one non-limiting embodiment of the present invention.
Figure 119:
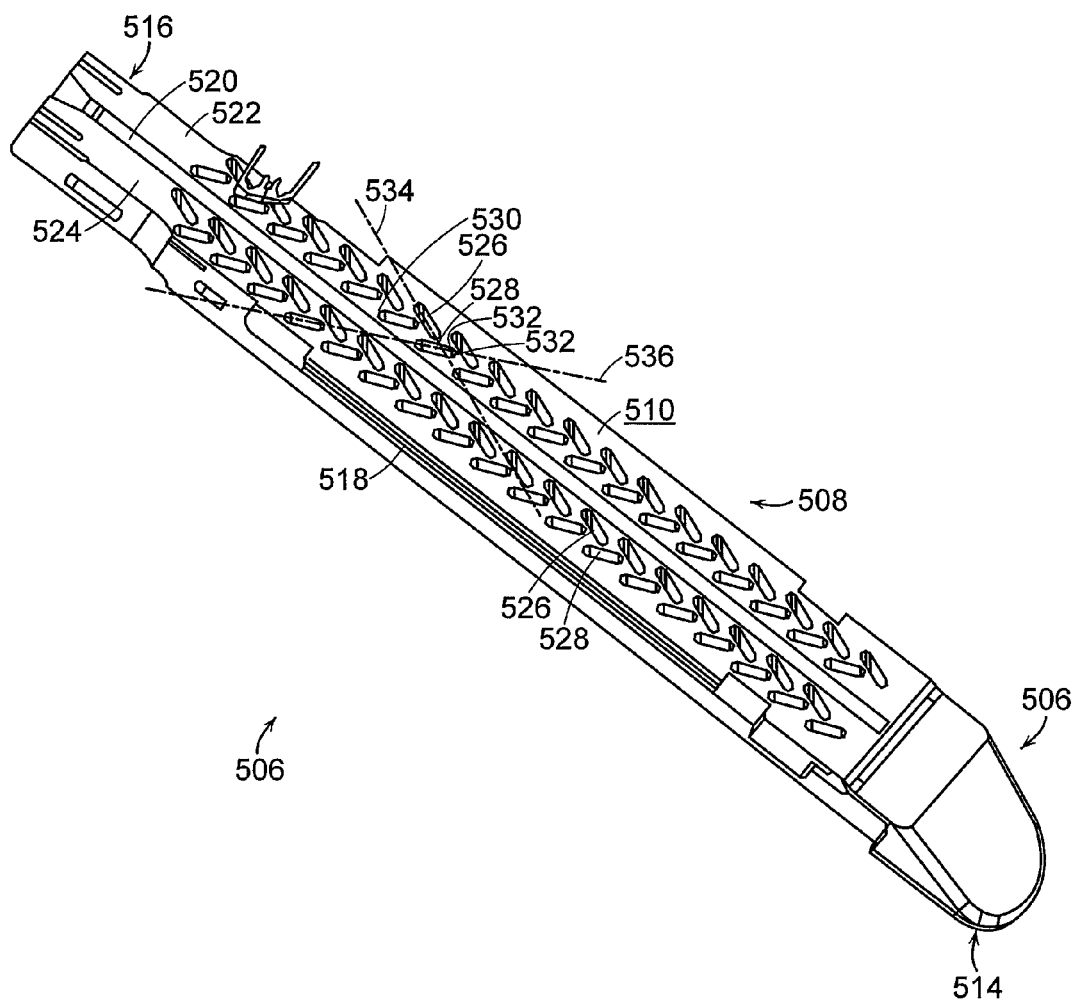
FIG. 119 is a perspective view of the staple cartridge of FIG. 118.

In various embodiments, referring to FIGS. 118 and 119, staple cartridge 506 can include staple cartridge body 508 where staple cartridge body 508 can include top surface 510, bottom surface 512, distal end 514, proximal end 516, and two side walls 518. In at least one embodiment, side walls 518 of staple cartridge body 508 can extend between top surface 510 and bottom surface 512, and top and bottom surfaces 510 and 512 can be defined between distal end 514 and proximal end 516. In various embodiments, referring to FIGS. 118 and 119, staple cartridge body 508 can further include slot 520 where the longitudinal axis of slot 520 can be parallel to, or substantially parallel to, a longitudinal axis of body 508. In at least one embodiment, "substantially parallel", for purposes herein, can mean being within about 15 degrees of parallel in either direction. In various embodiments, slot 520 can be defined through proximal end 516 and/or distal end 514 and can be configured to receive a cutting member adapted to sever soft tissue, for example. In either event, slot 520 can define first side 522 and second side 524 of staple cartridge body 508.

In various embodiments, referring to FIGS. 118 and 119, staple cartridge body 508 can include at least one first staple cavity 526 and at least one second staple cavity 528 where first cavity 526 and second cavity 528 can be defined in top surface 510 and/or bottom surface 512. In at least one embodiment, first cavity 526 and second cavity 528 can be situated on first side 522 and/or on second side 524 of staple cartridge body 508. In various embodiments, first cavity 526 and second cavity 528 can each have a first end 530 and a second end 532 where first axis 534 can be defined between first end 530 and second end 532 of first cavity 526 and, similarly, second axis 536 can be defined between first end 530 and second end 532 of second cavity 528. In at least one such embodiment, first axis 534 of first cavity 526 can be transverse to second axis 536 of second cavity 528 such that axes 534 and 536 can create an acute or obtuse angle therebetween. In other various embodiments, first axis 534 of first cavity 526 may be perpendicular to, or substantially perpendicular to, second axis 536 of second cavity 528. In various embodiments, still referring to FIGS. 118 and 119, a plurality of first cavities 526 can be parallel to, or substantially parallel to, one another and, likewise, a plurality of second cavities 528 can be parallel to, or substantially parallel to, one another. In other various embodiments, neither the plurality of first cavities 526 nor the plurality of second cavities 528 may be parallel to, or substantially parallel to, each other.

In at least one embodiment, first cavity 526 can be configured to receive a first staple and second cavity 528 can be configured to receive a second staple where each staple can include a first leg 544 and a second leg 546. In at least one embodiment, referring to FIG. 120, first leg 544 of the first staple may be situated at first end 548 of first cavity 538 and second leg 546 of first staple may be situated at second end 550 of first cavity 538. In a similar fashion, first leg 544 of second staple may be situated at first end 548 of second cavity 540 and second leg 546 of second staple may be situated at second end 550 of second cavity 540. In various embodiments, both first leg 544 of the first staple and second leg 546 of the second staple can lie on, or be positioned closely proximate to, common axis 552. In such embodiments, common axis 552 can define first common axis side 554 and second common axis side 556. In various embodiments, second leg 546 of the first staple in first cavity 538 may lie on first common axis side 554 and first leg 544 of the second staple in second cavity 540 may lie on second common axis side 556. As a result of such a configuration, referring to FIG. 120, for example, the first and second staples can be configured to compress, or constrict, blood vessels which extend perpendicular to axis 552 and, in addition, blood vessels which extend transverse and/or parallel to axis 552.

Figure 120:
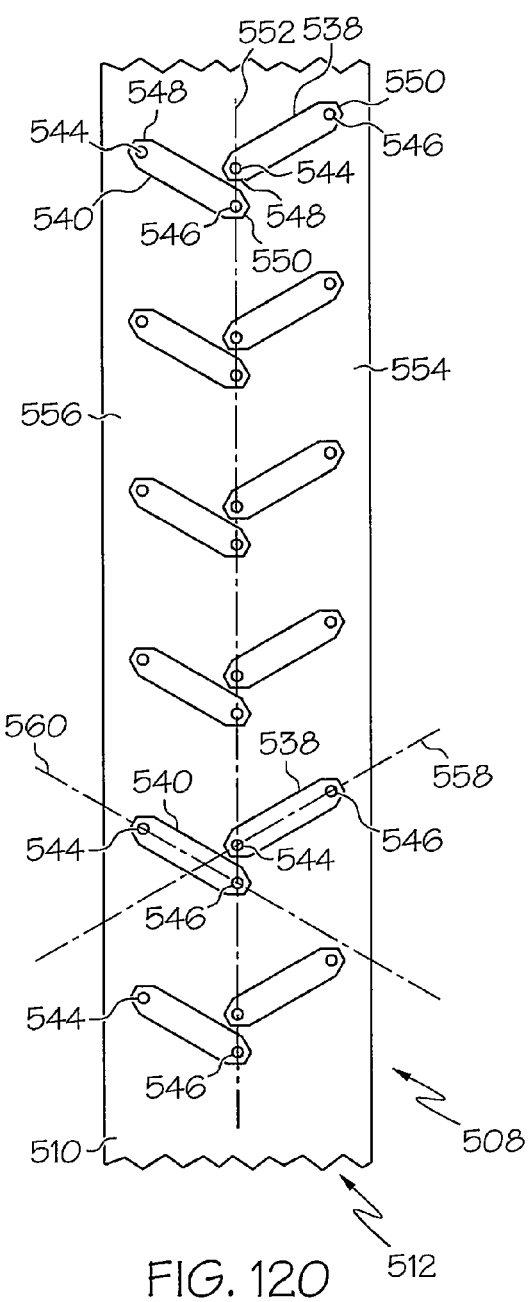
FIG. 120 is a partial plan view of a staple cartridge having a staple pattern in accordance with one alternate embodiment of the present invention.

In various embodiments, referring to FIG. 120, first axis 558 may be defined between first leg 544 and second leg 546 of the first staple within first cavity 538, and, similarly, second axis 560 may be defined between first leg 544 and second leg 546 of the second staple within second cavity 540. In at least one embodiment, first axis 558 can be transversely situated with respect to second axis 560 such that, in effect, first cavity 538 and second cavity 540 can be situated transversely with respect to each other. In other various embodiments, first axis 558 can be perpendicular to, or substantially perpendicular to, second axis 560 such that first cavity 538 and second cavity 540 are perpendicularly situated with respect to each other.

Figure 121:
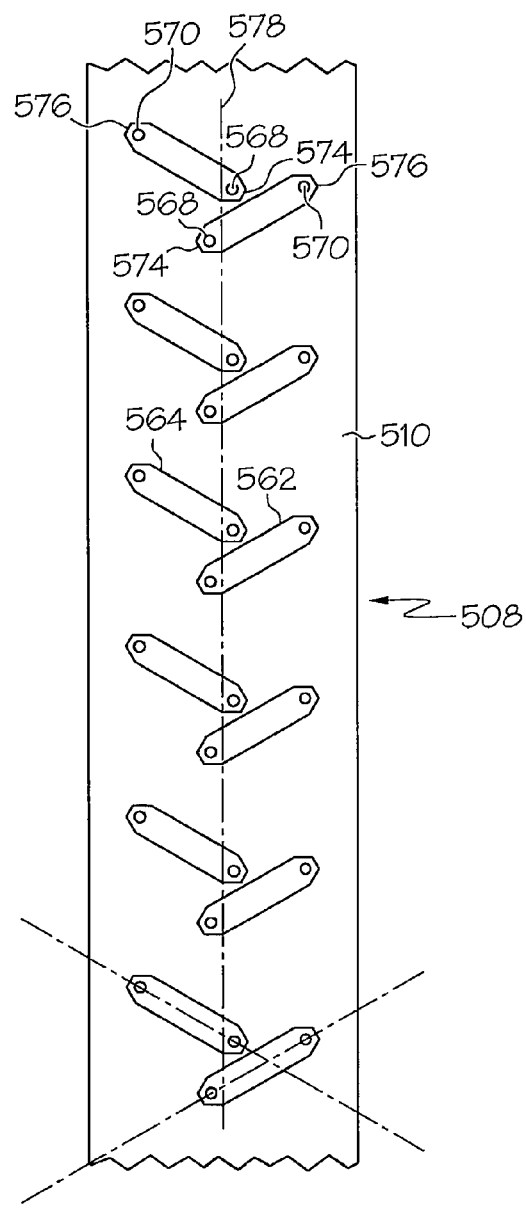
FIG. 121 is a partial top view of a staple cartridge having a staple pattern in accordance with another alternate embodiment of the present invention.
Figure 122:
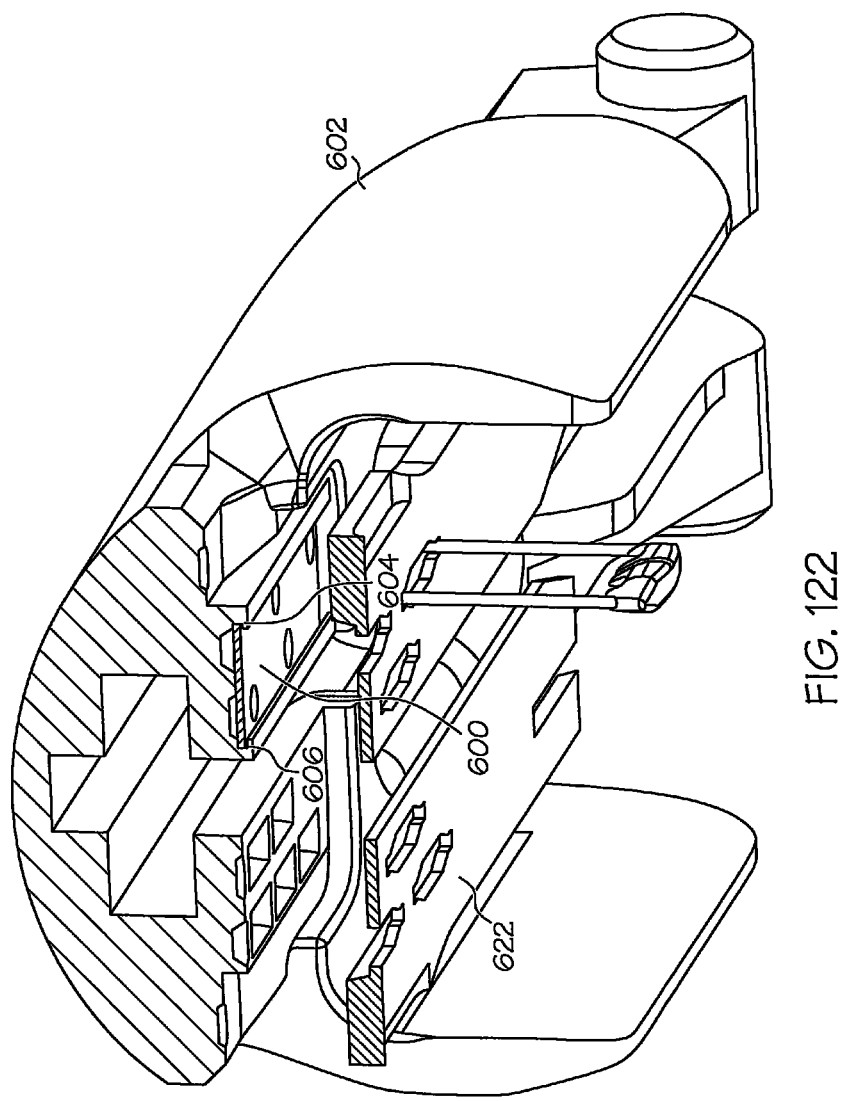
Figure 123:
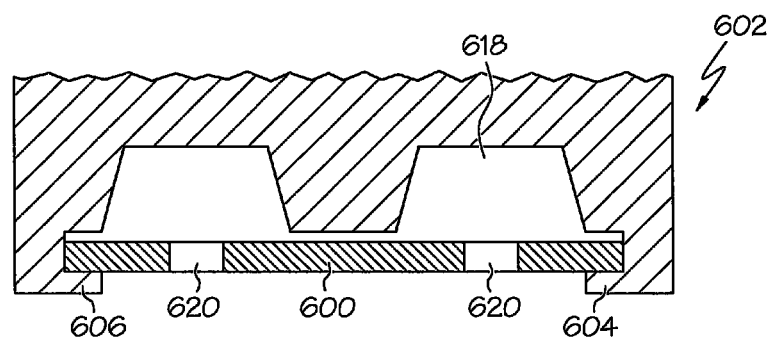

In various embodiments, referring to FIG. 121, staple cartridge body 508 can include a plurality of first cavities 562 and a plurality of second cavities 564 defined therein which can be configured to receive first and second staples, respectively, where the staples can each include a first leg 568 and a second leg 570. In various embodiments, similar to the above, first legs 568 of the first staples can be situated at first ends 574 of first cavities 562 and, similarly, second legs 570 of the first staples can be situated at second ends 576 of first cavities 562. In at least one embodiment, first legs 568 of the second staples can be situated at first ends 574 of second cavities 564 and second legs 570 of the second staples may be situated at second ends 576 of second cavities 564. In various embodiments, again referring to FIG. 121, first legs 568 of the first staples can be positioned on one side of axis 578 and second legs 570 of the first staples can be positioned on the other side of axis 578. In at least one embodiment, first legs 568 of the second staples can be positioned on the same side of axis 578 as second legs 570 of the first staples. In various embodiments, second legs 570 of the second staples can be positioned on the opposite side of axis 578 that first legs 568 of the second staples are positioned on. In other various embodiments, the first and second staples can be arranged in any other suitable configuration as long as legs 568 and 570 of first staples 566 and legs 568 and 570 of second staples 572 are each respectively situated on opposite sides of common axis 578.

Figure 124:
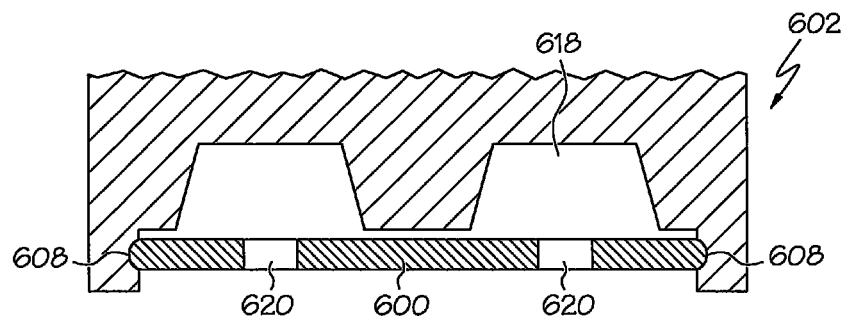
Figure 125:
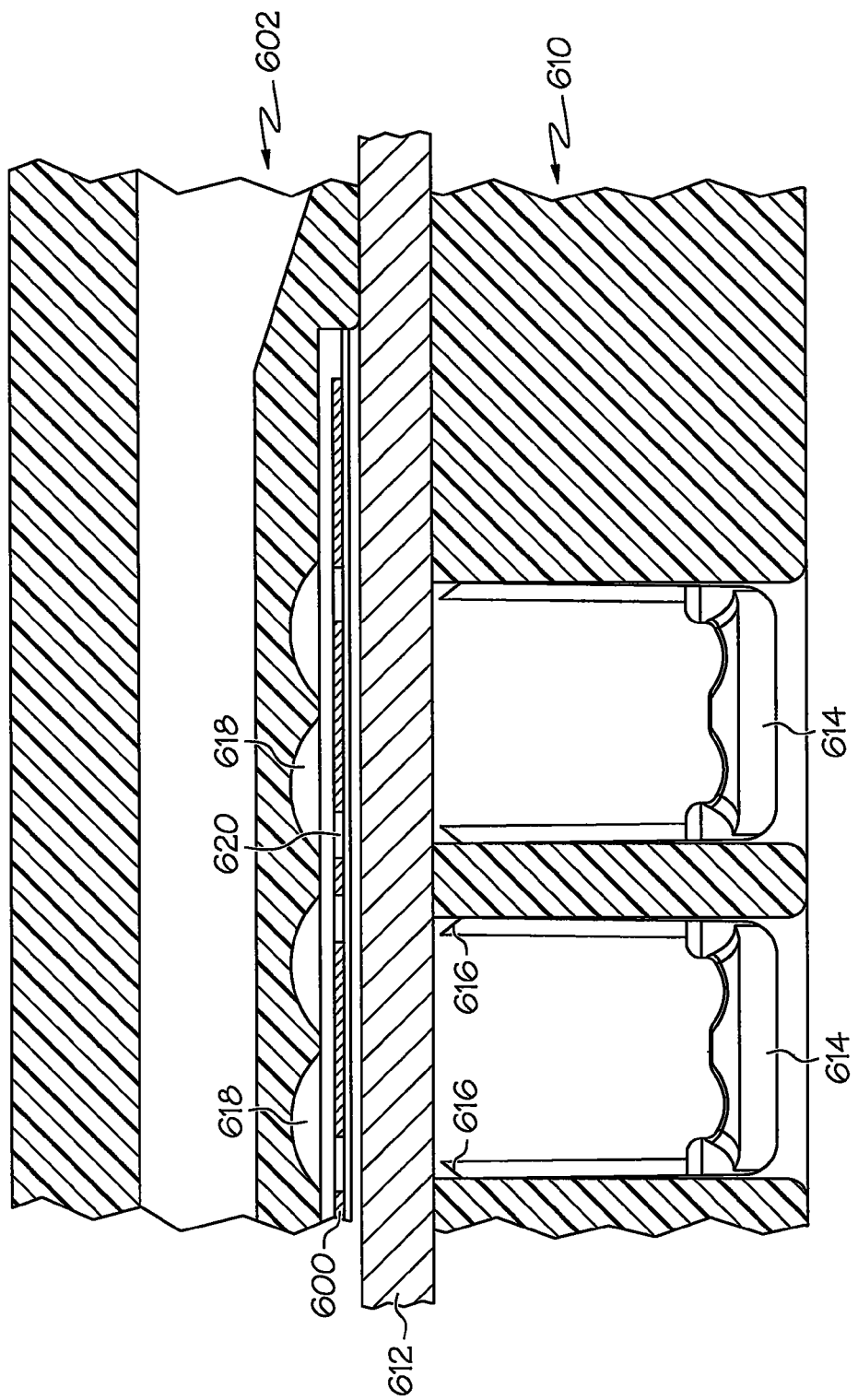

In various embodiments of the present invention, buttress material can be used to stiffen and/or strengthen soft tissue after it has been stapled. In at least one embodiment, referring to FIGS. 122-127, buttress material 600 can be used in conjunction with a surgical stapler where the surgical stapler can include anvil 602 and staple cartridge 610. In such embodiments, surgical staples can be deployed from staple cartridge 610 and can be deformed by anvil 602 in order to capture buttress material 600 against soft tissue 612 positioned between staple cartridge 610 and anvil 602. In various embodiments, buttress material 600 may be releasably retained to anvil 602 and/or staple cartridge 610. More particularly, in at least one embodiment, anvil 602 can include first lip 604 extending therefrom which can be configured to releasably capture buttress material 600 to anvil 602. In various embodiments, first lip 604 can fully surround the perimeter of buttress material 600, or, in other embodiments, first lip 604 can contact less than the full perimeter of buttress material 600. In various embodiments, the term "perimeter" can include the geometric perimeter of the buttress material and, in addition, the outer portions, edges, or areas of the buttress material. In at least one embodiment, anvil 602 may further include second lip 606 extending therefrom which can releasably capture buttress material 600 in a similar fashion as first lip 604. In at least one alternative embodiment, referring to FIG. 124, anvil 602 can include one or more notches, or slots, 608 which can releasably retain buttress material 600 to anvil 602. In various embodiments, notches, or slots, 608 can be used in conjunction with first lip 602 and/or second lip 604, for example.

Figure 126:
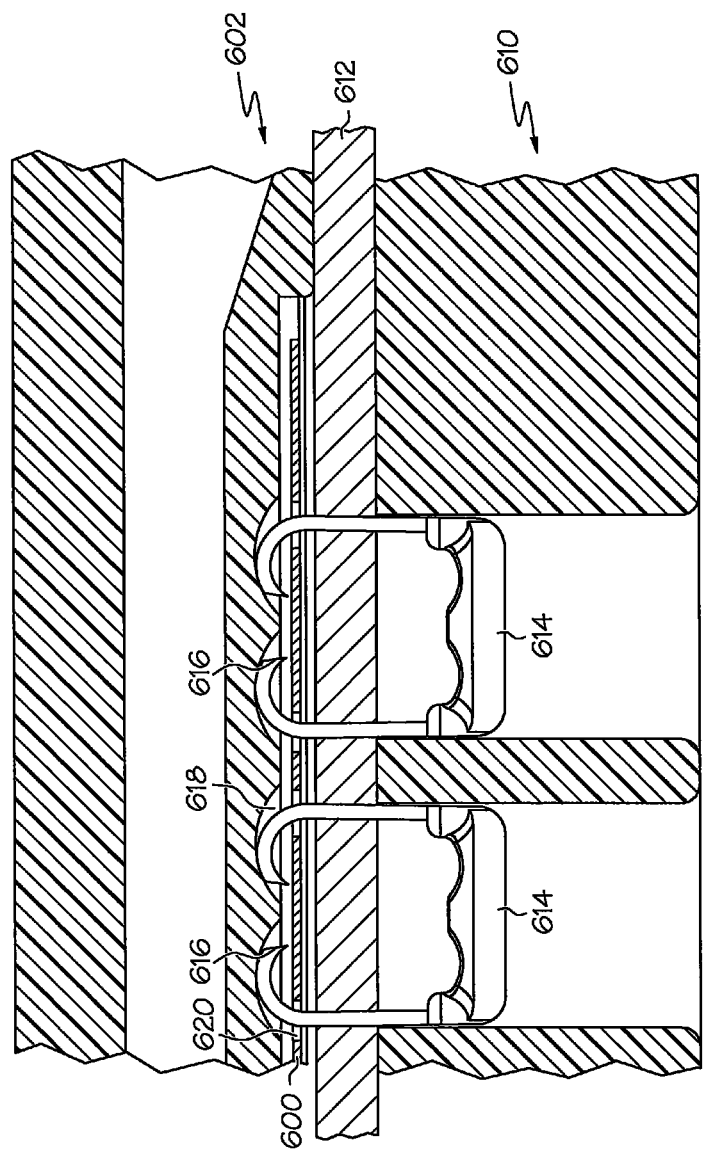
Figure 127:
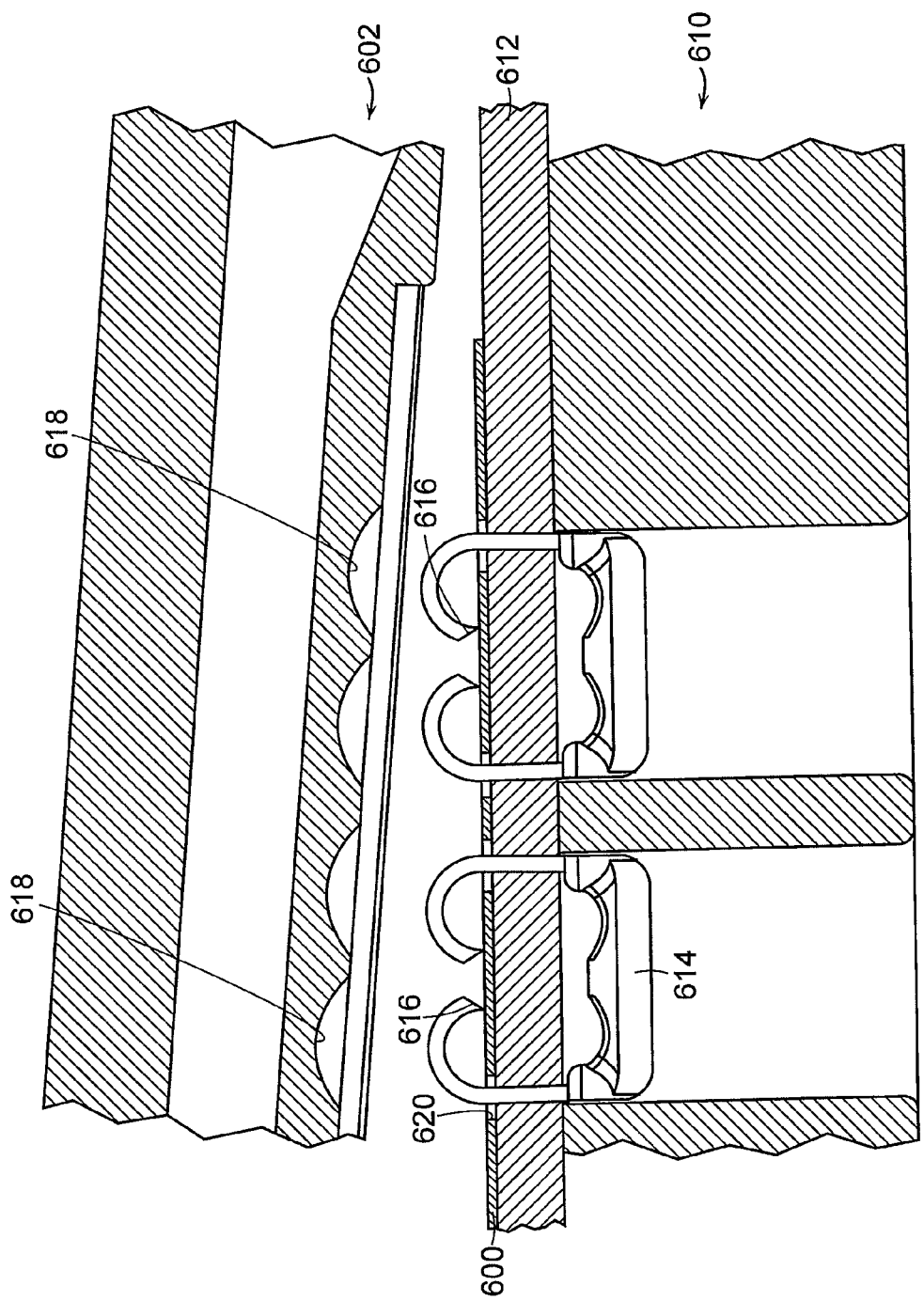

In various embodiments, as outlined above, anvil 602 and staple cartridge 610 can comprise jaw members which can be configured to apply a compressive force, or pressure, to soft tissue 612 captured therebetween. Staple cartridge 610, referring to FIG. 125, can include a plurality of staples 614 situated therein where each staple 614 can include at least one deformable member having an end 616. In at least one embodiment, buttress material 600 can include apertures 620 therein where apertures 620 can be configured to receive staple ends 616 such that the deformable members of staples 614 can move, or slide, relative to buttress material 600. In alternative embodiments, staple ends 616 can be configured to pierce buttress material 600 to create apertures therein. In either event, staples 614 can be deployed toward anvil 602 such that staple ends 610 can contact anvil pockets 618 in anvil 602 and the deformable members of staples 614 can be bent as illustrated in FIG. 126. In at least one embodiment, as a result, the deformable members can contact buttress material 600 and apply a force thereto to dislodge buttress material 600 from anvil 602. Stated another way, the deformable members can extend through buttress material 600 in a first direction and contact buttress material 600 in a second direction after being deformed by anvil 602. In at least one embodiment, buttress material 600 may not be immediately released from anvil 602 after the deformable members have been deformed. In such embodiments, referring to FIG. 127, buttress material 600 can be released from anvil 602 when anvil 602 is moved into its open position.

In various embodiments, as outlined above, buttress material 600 may strengthen or stiffen the soft tissue 612. More particularly, in at least one embodiment, buttress material 600 can increase the modulus of elasticity of the soft tissue after it has been affixed to thereto. In various embodiments, the buttress material can distribute the compressive load of the staples over a larger area thereby reducing the stress created within the soft tissue. In at least one embodiment, buttress material 600, for example, can prevent, or at least inhibit, the soft tissue from entering into anvil pockets 618. More particularly, when anvil 602 is closed onto the soft tissue and a compressive pressure is applied thereto, the soft tissue may flow into anvil pockets 618 to reduce this pressure and thereby affect the ability of the staples to properly engage and retain the soft tissue. When buttress material 600 is used, however, buttress material 600 can be configured to block, or at least substantially block, the soft tissue from entering into anvil pockets 618. In various embodiments, buttress material 600 can be comprised of an absorbable, biofragmentable, or dissolvable material, much like the materials that can be used to form crowns 310 and bridges 340 described above. In at least one embodiment, buttress material 600 can include a therapeutic material that can be released to aid in healing, as discussed above. In various embodiments, a flexible, rigid or semi-rigid substance can be used to create buttress material 600.

Figure 3:
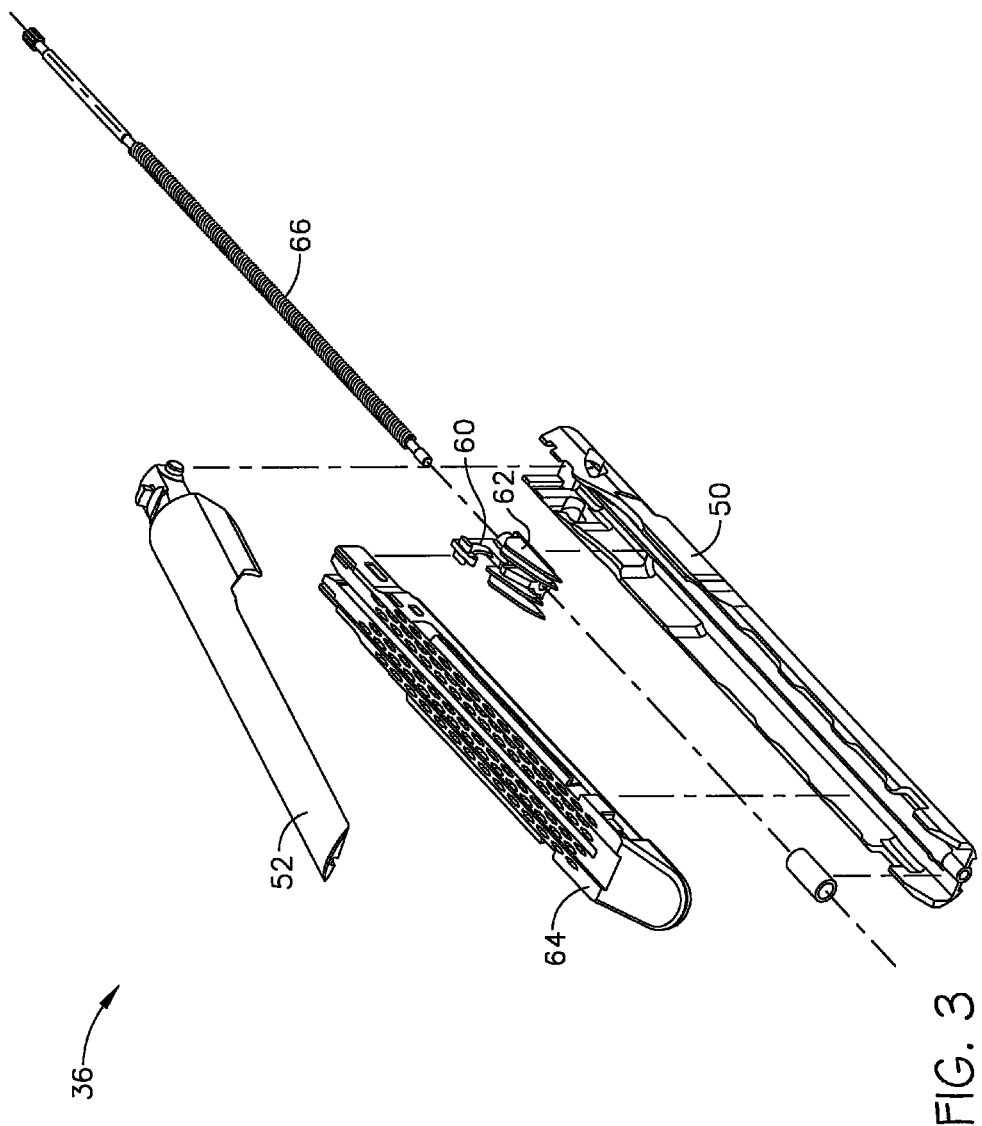
FIG. 3 is an exploded view of an end effector of the surgical instrument of FIG. 1.
Figure 128:
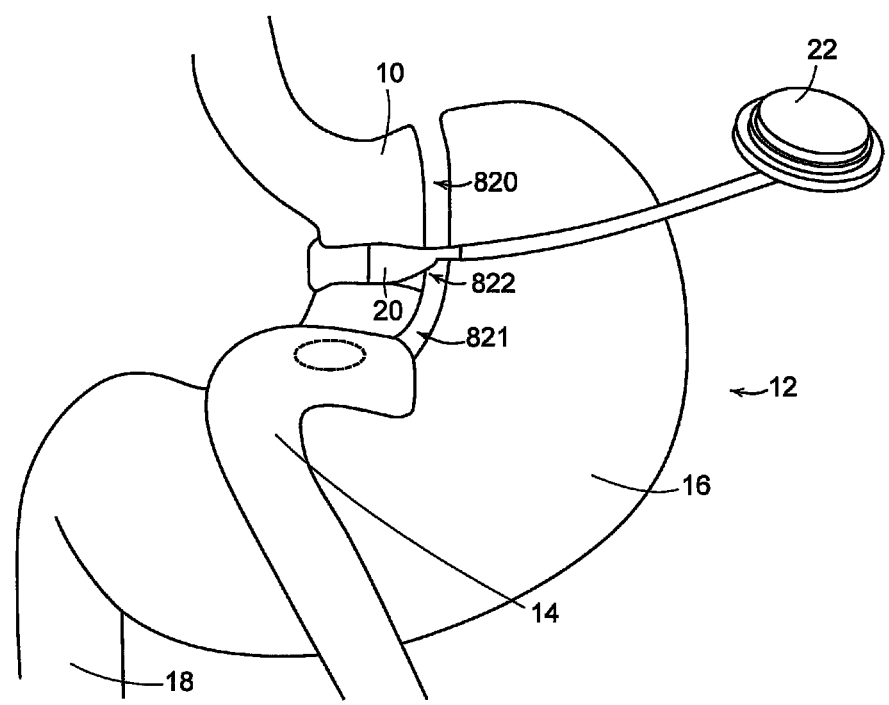

Various embodiments of the present invention are directed to surgical procedures using an endocutter 30 (see FIG. 1) where, for at least part of the procedure, end effector 36 of endocutter 30 is loaded with staple cartridge 64 (see FIG. 3) having staples with an integrated crown-driver. Further, the integrated crown-driver may include recesses, such as recesses 144 shown in FIGS. 5-9, for turning the ends of the staples. Such a staple cartridge 64 could be used in a Roux-en-Y gastric bypass procedure. In such a procedure, with reference to FIG. 128, the stomach is made smaller by creating small pouch 10 at the top of stomach 12 where small stomach pouch 10 can be connected directly to the middle portion of the small intestine (jejunum) 14, thereby bypassing the rest of stomach 16 and the upper portion of small intestine (duodenum) 18. As shown in FIG. 128, adjustable band 20 is sometimes placed around the stomach pouch 10 to control the expansion of pouch 10. The pressure exerted by band 20 on stomach pouch 10 can be controlled by port 22 in communication with band 20. With reference to FIGS. 1 and 3, endocutter 30 used in the procedure could be loaded with a staple cartridge 64 having staples with integrated crown-drivers, with or without the staple-end-turning recesses 144, for the cut near where gastric band 20 is to be placed. This way, the exterior surfaces of the tissue and/or the band 20 will be protected from the ends of the staples, thereby reducing the chance that the staple ends cut or snag or otherwise damage band 20, and reducing the chance that band 20 aggravates the staples.

In various embodiments, the clinician may use one endocutter 30 in the procedure. Endocutter 30 may be loaded with a staple cartridge having conventional staples, such as described in U.S. Pat. No. 5,465,895, for the cuts that will not be in the area of band 20, such as the areas 820, 821 in FIG. 128. For the cut or cuts that will be in area 822 of band 20, endocutter 30 can be loaded with a staple cartridge having staples with integrated crowns-drivers. In another embodiment, the clinician may use two (or more) separate endocutters 30 in the procedure. One endocutter 30 could be used for the cuts in the areas 820, 821 that will not be near band 20, and the other endocutter 30, loaded with a staple cartridge having staples with integrated crowns-drivers for the cut(s) in area 822 that will be in the area of band 20.

Figure 129:
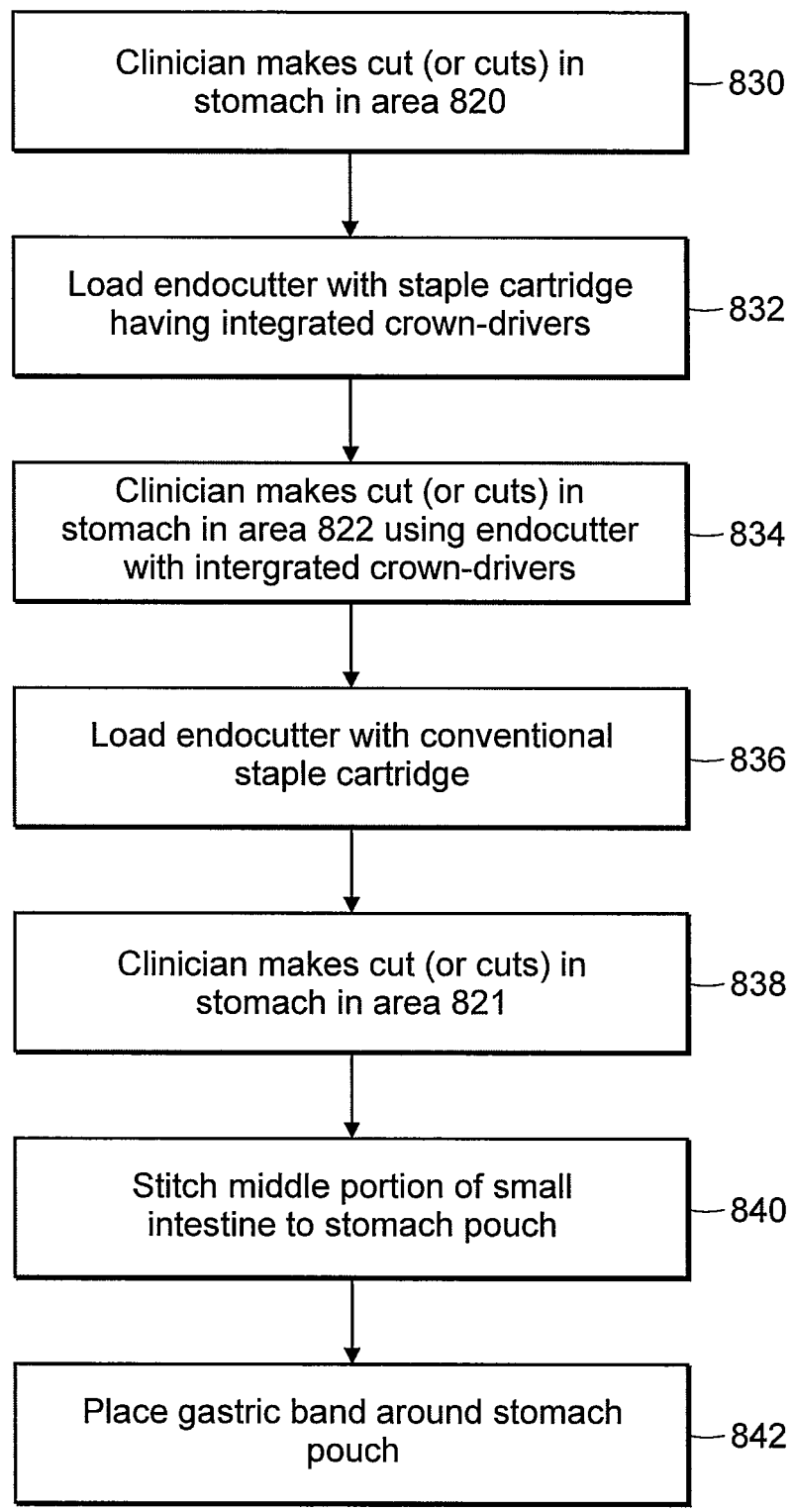

FIG. 129 is a flow chart of the process according to various embodiments. At step 830, the clinician uses an endocutter 30 having a conventional staple cartridge for the cut(s) for area 820 (see FIG. 128). In various embodiments, of course, a different conventional staple cartridge will need to be used for each cut in area 820. Once the clinician nears area 822 where band 20 is to be placed, at step 832, the endocutter 30 may be loaded with a staple cartridge having staples with integrated crowns-drivers. The clinician may then, at step 834, make the necessary cut or cuts for area 822. Of course, if more than one cut is needed in area 822, for each such cut the endocutter 30 may be loaded with a staple cartridge having staples with integrated crowns-drivers. Once the clinician is past the area where the band 20 is to be placed, at step 836, the endocutter 30 may be loaded with a conventional staple cartridge for each additionally required cut (step 838) in area 821 to form pouch 10. Once pouch 10 is formed, at step 840, the middle portion of patient's small intestine (jejunum) 14 may be stitched to stomach pouch 10. Then, at step 842, gastric band 20 may be placed around stomach pouch 10, such that band 20 is placed in the area where the staples with the integrated crowns-drivers were used. That way, the likelihood of the staple ends snagging or rupturing band 20 is reduced, as is the likelihood that band 20 will aggravate the staples. According to various embodiments, an endocutter 30 with a staple cartridge 64 having integrated crown-drivers may be used for each cut used in forming stomach pouch 10.

Thus, according to various embodiments, the present invention is directed to a process for performing a Roux-en-Y gastric bypass procedure comprising performing a plurality of cutting/fastening steps with a stapling endocutter 30 instrument on a patent's stomach in order to cut the stomach into two parts (e.g., pouch 10 and bypassed stomach 16) and to seal, with the staples, the two parts along the cut path. For each cut, the endocutter 30 may be loaded with a new staple cartridge, and for at least one of the cuts, the staple cartridge comprises staples with integrated crowns-drivers, as described above. The middle portion of patient's small intestine (jejunum) 14 may then be stitched to stomach pouch 10, using techniques known in the art, for example. Then gastric band 20 may be placed around stomach pouch 10, such that band 20 is placed in the area where the staples with the integrated crowns-drivers were used.

Figure 130:
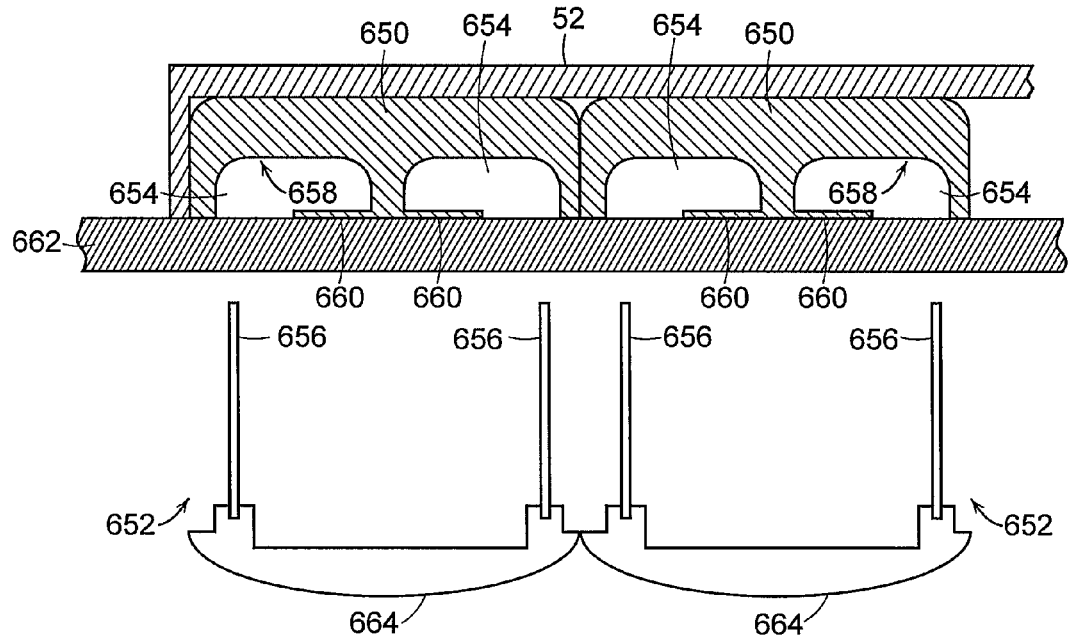
Figure 131:
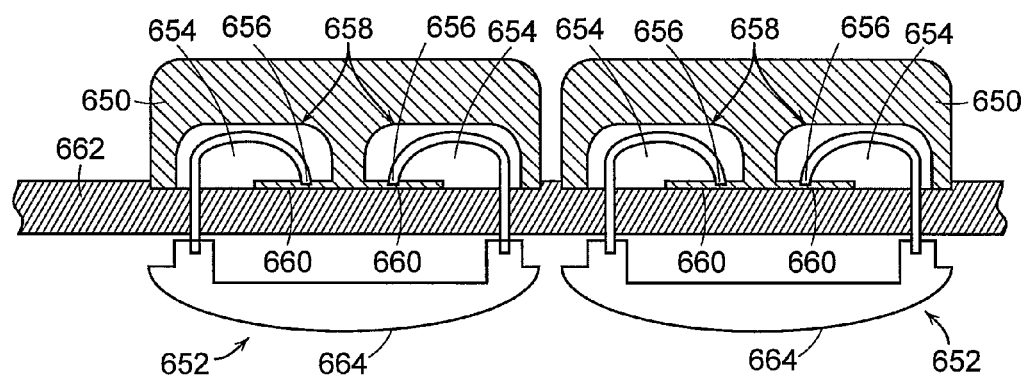

FIGS. 130 and 131 are cross-sectional side views of portions of end effector 36 according to other various embodiments of the present invention. In the illustrated embodiment, a number of releasable pocket elements 650 are fitted into anvil 52. In the illustrated embodiment, there is a corresponding releasable pocket element 650 for each staple 652 in the staple cartridge, although in other embodiments, as described further below, a different ratio of releasable pocket elements 650 to staples may be used. The releasable pocket elements 650 may be, for example, integrally formed, snap-fit or otherwise inserted into anvil 52 prior to use of endocutter 30.

As shown in the embodiment of FIGS. 130 and 131, releasable pocket elements 650 may define pockets 654 in to which ends 656 of staples 652 are driven when the endocutter 30 is fired. Upon firing, as shown in FIG. 131, ends 656 may first engage and be turned by an upper surface 658 of pocket 654. Upper surface 658 of pocket 654 may turn ends 656 of staples 652 toward a staple-end retaining surface 660 at the lower edge of pocket element 650. Staple-end retaining surfaces 660 may retain or trap ends 656 of staples 652 in pockets 654.

The force of the firing operation is preferably greater than the force holding pocket elements 650 in anvil 52, such that pocket elements 650 are released or popped-out from anvil 52 upon firing, as shown in FIG. 131. That way, pocket elements 650 may remain with staples 652 in tissue 662 following the cutting/fastening operation, as shown in FIG. 131. As also can be seen in FIG. 131, pocket elements 650 may separate after being released from the anvil 52 and move with the tissue 662, for example.

Retaining surface 660 may prevent end 656 of staple 652 from protruding out of pocket 654 and into tissue 662 being fastened by staples 652. Further, for procedures using a band around tissue that has been stapled, such as gastric band 20 in the Roux-en-Y gastric bypass procedure described above, (see FIG. 128) pocket elements 650 may prevent ends 656 of staples 652 from damaging the band 20, as well as prevent the band 20 from damaging the staple line. Among other things, this may reduce the risk of infection at the site of band placement.

Retaining surfaces 660 are preferably strong enough so that ends 656 of staples 652 do not puncture retaining surfaces 660, and strong enough to withstand the force required to release pocket elements 650 from anvil 52. Also, retaining surfaces 660 are preferably small enough that the do not inhibit the insertion of staple ends 656 into pockets 654. According to various embodiments, retaining surfaces 660, like the rest of pocket element 650, may be made of a thermoplastic material, such as Victrex PEEK plastic, for example. The thickness of retaining surfaces 660 may be selected based on size of the staples 652 being used, and retaining surfaces 660 may be on the order of 0.010 inches thick according to various embodiments.

According to various embodiments, pocket elements 650 may be made from the same material as crowns 664 of the staples 652. For example, they could be both made from bioabsorbable material or non-bioabsorbable material. Also, either pocket elements 650 or crowns 664, or both, could be laced with or otherwise comprise a therapeutic agent or drug, such as a pain relieving drug or anti-bacterial agent, that can be absorbed by surrounding tissue 662.

Figure 132:
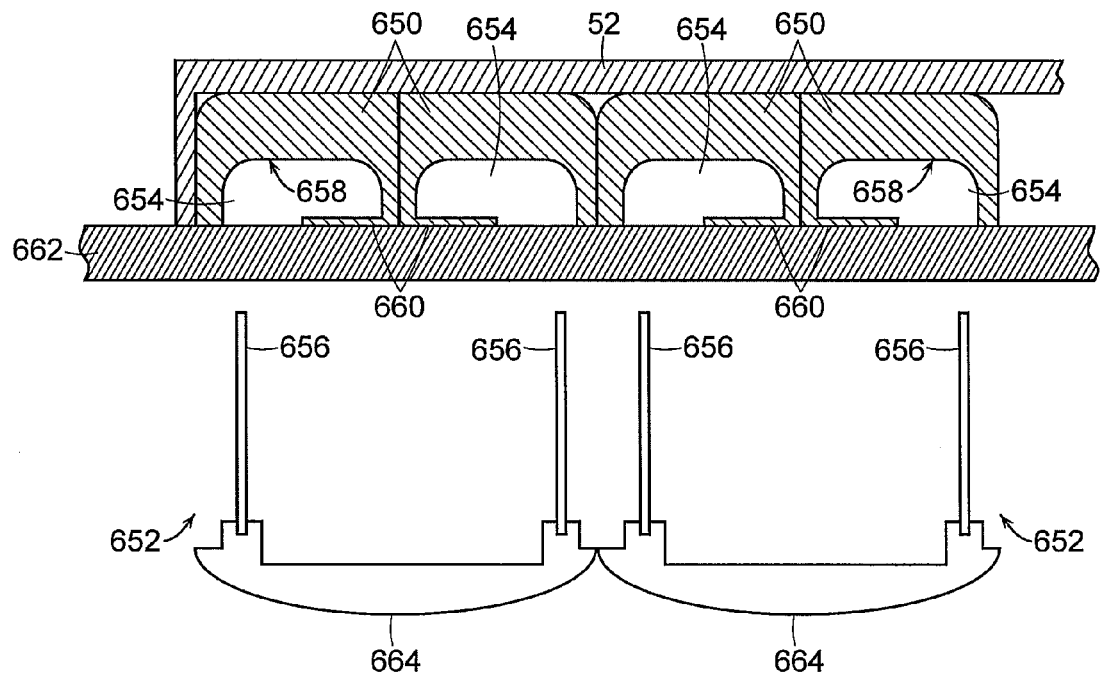
Figure 133:
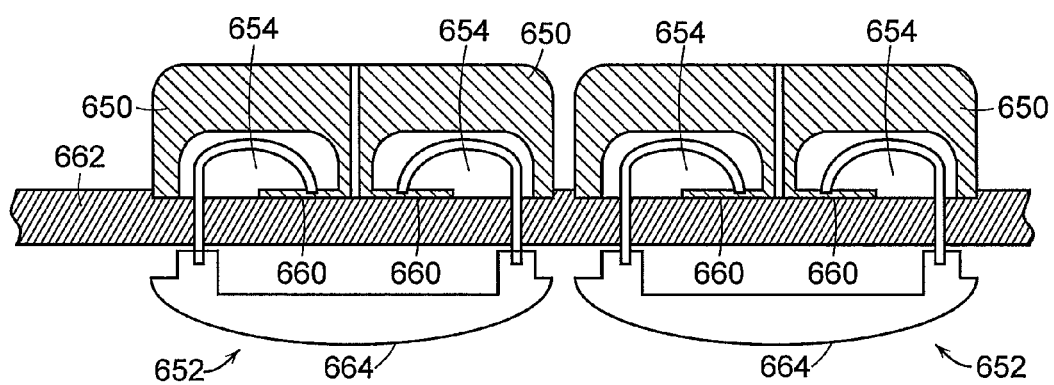

FIGS. 132 and 133 show another embodiment of releasable pocket elements 650, where each releasable pocket element 650 in the illustrated embodiment comprises one pocket 654. As such, there may be two pocket elements 650 for each staple 652 in such an embodiment. It should be noted that in various embodiments, a number of different pocket elements 650 could be disposed in anvil 52 for use at one time. For example, for one use, some of pockets elements 650 may comprise two (or more) pockets 654, and some may comprise only one pocket 654. A typical staple cartridge 64 has sixty-six staples, in six rows (three for each side of the incision). Preferably, there would therefore be one hundred thirty two (132) pockets between all of pocket elements 650 placed in the anvil 52—two pockets for each staple 652 (or one pocket for each staple end 656).

An endocutter having anvil 52 loaded with such releasable pocket elements could also be used for cutting steps in the area where a band is to be placed around the cut tissue, such as in a Roux-en-Y gastric bypass procedure, as described above. The clinician may use a separate endocutter 30, having anvil 52 with releasable pocket elements 650 for the cut in the area where band 20 is to be placed, or the clinician could use one endocutter 30 in the procedure, where the clinician (and/or a member of his/her team) modifies anvil 52 to insert releasable pocket elements 650 for the cut where band 20 is to be placed. In yet another embodiment, the endocutter 30 could allow for interchangeable anvils 52, where one anvil 52 does not have releasable pocket elements 650 and another one does. Anvil 52 with releasable pocket elements 650 could then be used for the cut in the area of band 20.

In various embodiments, the surgical staples discussed above, or incorporated herein by reference, can be used, not only with a linear stapler, but also with a circular surgical stapler. In the circular stapler embodiment, the surgical staples can have the same features, functions and compositions as discussed above. Instead of loading the staples into a plurality of cavities in a staple cartridge having a linear configuration, however, the staples are instead loaded into a plurality of cavities in a staple cartridge having a circular configuration.

In various embodiments, referring to FIGS. 134-136, circular stapler 900 can include head 902, anvil 904, adjustment knob assembly 906, and trigger 908 where head 902 can be coupled to handle assembly 910 by arcuate shaft assembly 912. In at least one embodiment, trigger 908 can be pivotally supported by handle assembly 910 and can act to operate stapler 900 when a safety mechanism (not illustrated) is released. When trigger 908 is activated, a firing mechanism (not shown in FIG. 134) can operate within shaft assembly 912 so that staples 914 are expelled, or deployed, from head 902 into forming contact with anvil 904. Simultaneously, knife 916 operably supported within head 902 can act to cut tissue clamped between head 902 and anvil 904. Stapler 900 can then removed from the surgical site leaving the stapled tissue in its place.

FIGS. 135 and 136 illustrate one form of anvil 904 and head 902 that may be employed in connection with various embodiments of the subject invention. As can be seen in these figures, anvil 904 can include circular body portion 920 having anvil shaft 922 for attaching a trocar (not shown) thereto. In at least one embodiment, anvil body 920 can include staple forming surface 924 thereon and can also include shroud 926 attached to the distal end thereof. Anvil 904 may be further provided with a pair of trocar retaining clips or leaf-type springs 928 that can serve to releasably retain the trocar in retaining engagement with anvil shaft 922. In various embodiments, plastic knife board 930 may be fitted into cavity 932 in anvil body 904.

In various embodiments, referring to FIG. 136, head 902 may comprise casing member 940 that supports a cartridge supporting assembly in the form of circular staple driver assembly 942 therein that is adapted to interface with circular staple cartridge 944 and drive staples 914 supported therein into forming contact with staple forming surface 924 of anvil 904. In at least one embodiment, circular knife member 916 is also centrally disposed within staple driver assembly 942. In various embodiments, the proximal end of casing member 940 may be coupled to outer tubular shroud 946 of arcuate shaft assembly 912 by distal ferrule member 948. More details regarding circular staples and staplers may be found in U.S. patent application Ser. No. 11/541,151, entitled SURGICAL CUTTING AND STAPLING DEVICE WITH CLOSURE APPARATUS FOR LIMITING MAXIMUM TISSUE COMPRESSION FORCE, which was filed on Sep. 29, 2006, the disclosure of which is hereby incorporated by reference herein.

When performing an anastomosis, a lumen, such as the large or small intestine, for example, can be stapled using a circular surgical stapler with at least two rows of staples being emplaced on either side of a target section (i.e., specimen) of the intestine. In various embodiments, the target section is usually simultaneously cut as the section is stapled. Next, after removing the specimen, a surgeon can insert the anvil into the proximal end of the lumen, proximal of the staple line. In at least one embodiment, this is done by inserting the anvil head into an entry port cut into the proximal lumen by the surgeon. On occasion, the anvil can be placed transanally, or even transorally, by placing the anvil head on the distal end of the stapler and inserting the instrument through the rectum or mouth, respectively. In order to operably engage the anvil with the surgical stapler, in various embodiments, the distal end of the stapler may be inserted transanally, for example. The surgeon can then tie the proximal end of the intestine to the anvil shaft using a suture or other conventional tying device. Next, the surgeon can cut excess tissue adjacent to the tie and the surgeon can attach the anvil to the actuation shaft of the stapler. The surgeon can then close the gap between the anvil and cartridge, thereby engaging the incised proximal and distal ends of the intestine in the gap. The surgeon may next actuate the stapler causing at least two rows of staples to be driven through the incised proximal and distal ends of the intestine thereby joining the ends of the intestine and forming a tubular pathway after the staples have been formed. Simultaneously, as the staples are driven and formed, a concentric circular blade, knife or cutting member may be driven through the intestinal tissue ends, cutting the ends adjacent to the inner row of staples. The surgeon can then withdraw the stapler from the intestine and the anastomosis is complete.

In various embodiments, referring to FIGS. 137-139, the present invention is directed to surgical stapler 900 having washer 970 that is inserted in anvil 904, as shown in FIG. 137, which is an exploded view of washer 970 and anvil 904, and FIG. 138, which shows washer 970 inserted in anvil 904. In at least one embodiment, washer 904 may be pressure or snap fit into the opening of anvil 904 such that washer 904 is retained in place during the procedure. As can be seen in FIG. 139, washer 904 may include inner portion 972 and outer portion 974. Outer portion 974 may include inner row 976 and outer row 978 of staple guide sections. In various embodiments, each staple guide section 976, 978 may include holes 979 through which the ends of the inner and outer rows of staples 914, respectively, may be driven when circular stapler 900 is fired. The ends of the staples, after being driven through opening 979, may be turned, or deformed, by staple forming pockets 901 of anvil 904. Once turned by anvil 904, the end of staples 914 may contact staple guide sections 976, 978, thereby preventing the end of staples 914 from protruding into the tissue being severed/stapled. Also as can be seen in FIG. 139, outer portion 974 of washer 970 may have spring sections 980 between the staple guide sections of inner row 976 and outer row 978. In at least one embodiment, spring sections 980 may provide a discrete amount of flexibility relative to the nominal diameter of ring 972. In addition, inner staple guide sections 976 can be connected to inner portion 972 of the washer by tabs 982.

In various embodiments, washer 970, including inner portion 972 and outer portion 974, may be integrated together, being made from molded plastic. For reasons that will be apparent below, washer 970 can be made from a non-absorbable material, such as PEEK brand thermoplastic, although, in other embodiments, at least a portion of washer 970 could be made from a plastic material that is absorbable. In use, when fired, knife 916 may cut tabs 982, thereby causing outer portion 974 of washer 970 to break off from inner portion 972 of washer 970 at tabs 982, such that inner portion 972 can remain inside anvil 904 after the cutting/stapling step, but outer portion 974 can remain with the staples and the tissue after stapler 900 is removed. Having such a ring-type washer portion 972 that remains with the staples and tissue after a procedure may have several benefits. For example, for patients having operations which reduce the size of their stomach, such as Roux-en-Y gastric bypass surgery, ring-type washer portion 972 may prevent dilation of the gastrojejunal anastomosis by providing a fixed size staple line, i.e., fixed by the dimensions of ring-type washer portion 972. Fixing the size of the gastrojejunal anastomosis may prevent dilation of the stoma, thereby potentially allowing the patient to experience long-term weight reduction.

According to other embodiments, spring sections 980 may be formed from an elastic material that may be overmolded onto ring 972. Also, although ring 972 is shown in the figures as being generally circular, it should be recognized that ring 972 may assume other shapes, such as elliptical, for example. In a bowel anastomosis, elliptical ring 972 may potentially provide a larger lumen than a circular ring. Further, if a non-absorbable material is used for ring 972, the lumen could be held in a constant size and form.

In addition, in various embodiments, ring 972 may be laced with or otherwise comprise a healing agent that, when in contact with tissue would enhance the healing of the tissue within the anastomotic site. Additionally, ring 972 may include or otherwise comprise a remotely detectable material that allows the position and orientation of ring 972 to be sensed in the patient at some later point in time. For example, ring 972 could be made from a material that is opaque to certain frequencies of radio waves or otherwise detectable by electromagnetic radiation. That way, the position and orientation of ring 972 at the anastomotic site may be identifiable using an x-ray machine, for example. In other embodiments, ring 972 may be made from a material having or otherwise comprise fluorescent nanoparticles that can be detected using a fluoroscopy device. The nanoparticles may be, for example, inorganic nanoparticles, like a semiconductor nanocrystals, silica-based nanoparticles such as those described in U.S. patent application Ser. No. 10/536,569, entitled FLUORESCENT SILICA-BASED NANOPARTICLES, filed on Nov. 26, 2003, U.S. patent application Ser. No. 11/119,969, entitled PHOTOLUMINESCENT SILICA-BASED SENSORS AND METHODS OF USE, filed on May 2, 2005, and U.S. patent application Ser. No. 10/306,614, entitled FLUORESCENT SILICA-BASED NANOPARTICLES, filed on Nov. 26, 2002, the disclosures of which are hereby incorporated by reference herein, or any other inorganic particle capable of attaching to or containing a fluorescence material. The nanoparticles may be also be organic nanoparticles, like liposomal spheres, dimer structures, or other organic structures capable of attaching to or containing a fluorescence material.

In yet other embodiments, staple forming pockets 901 of anvil 904, may be integrated with ring 972. As such, ring 972 would include a pocket (not shown) for each staple leg opening 979, extending distally from the plane of ring 972, such that the staple legs would be turned by the pocket back on ring 972. In such an embodiment, the pockets in anvil 904 could be eliminated.

In various embodiments, referring to FIGS. 140-148, circular surgical stapler 700 can include staple cartridge mechanism 702, elongate shaft 704, and anvil member 706. In at least one embodiment, staple cartridge mechanism 702 can be removably attached to surgical stapler 700 such that, after the staples in a first staple cartridge mechanism 702 have been deployed, the first staple cartridge mechanism 702 can be removed and can be replaced with a second staple cartridge mechanism 702, for example. In various embodiments, referring to FIGS. 141 and 144, staple cartridge mechanism 702 can include staple cartridge portion 716 and actuation shaft 714 extending therefrom. In at least one embodiment, referring to FIGS. 140-142, actuation shaft 714 can be configured to extend through aperture 712 in anvil member 706. In such embodiments, surgical stapler 700 can further include an actuation mechanism (not illustrated in FIGS. 140-148) which can be configured to motivate actuation shaft 714 and thereby move staple cartridge mechanism 702 relative to anvil member 706. In at least one embodiment, aperture 712 can be positioned at the distal end of the actuation mechanism and can be configured to receive actuation shaft 714 in a snap-fit and/or press-fit arrangement. In various embodiments, although not illustrated, at least one of actuation shaft 714 and the actuation mechanism can include a detent mechanism which can releasably retain actuation shaft 714 to the actuation mechanism.

In various embodiments, when actuation shaft 714 is engaged in aperture 712, as described above, or is otherwise operably engaged with the actuation mechanism, the actuation mechanism can control the distance between anvil member 706 and staple cartridge mechanism 702. In at least one embodiment, in order to deploy staples removably stored within staple cartridge 716, a surgeon, or clinician, can actuate the actuation mechanism in order to pull actuation shaft 714 toward anvil member 706 and thereby cause the staples to contact anvil member 706 and secure soft tissue therein, as described above. In various embodiments, staple cartridge mechanism 702 can further include a staple driver (not illustrated) operably engaged with actuation shaft 714 such that, when actuation shaft 714 is pulled by the actuation mechanism, actuation shaft 714 can move the staple driver relative to staple cartridge portion 716 and deploy the staples therefrom. In either event, actuation shaft 714 can then be disengaged from the actuation mechanism and the spent staple cartridge mechanism 702 can be removed. In such embodiments, the remainder of surgical stapler 700 can be left in the surgical site while a new staple cartridge mechanism 172, for example, is attached thereto. Such embodiments are an improvement over previous surgical devices which required the surgeon to remove the entire surgical instrument from the surgical site to reload a new staple cartridge. In various embodiments, the time to complete a particular surgery can be reduced and, in various circumstances, the surgery can be less invasive to the patient.

In various alternative embodiments, referring to FIGS. 146 and 147, staple cartridge portion 716 of staple cartridge mechanism 702 can be detached from actuation shaft 714. In such embodiments, actuation shaft 714 can remain operably engaged with the actuation mechanism while the spent staple cartridge portion 716 is replaced. In either event, in various embodiments, knife, or cutting member, 718 can be mounted on either anvil member 706 (FIG. 140) or on staple cartridge mechanism 702 (FIG. 144). When cutting member 718 is mounted on anvil member 706, referring to FIG. 140, knife 718 can be mounted inboard of the plurality of anvil pockets 710 and may be moveable in an axial direction toward or away from staple cartridge mechanism 702. When mounted on staple cartridge mechanism 702, referring to FIG. 144, knife 718 can be mounted inboard of staple cartridge 716 and can be moveable in an axial direction towards or away from anvil member 706. In at least one various embodiment, cutting member 718 can rotate when it is moved axially as described above and can be configured to trim portions of the intestine near the staple line.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A staple cartridge assembly, comprising:
   a plurality of staples, wherein each said staple comprises:
      a base;
      a deformable member extending from said base; and
      a crown, wherein said deformable member is slidable relative to said crown; and
   a staple cartridge body configured to removably store said staples, said staple cartridge body comprising:
      a deck comprising a top surface;
      a plurality of staple cavities configured to receive said deformable members, wherein each said staple cavity comprises an opening in said deck; and
      a plurality of recesses defined in said deck, wherein each said recess surrounds a said opening, and wherein said crowns are removably positioned in said recesses,
   wherein said crowns are removably attached to said deck, wherein said crowns are integrally molded with said deck, and wherein said bases of said staples are configured to contact said crowns and dislodge said crowns from said deck.

2. A fastener cartridge assembly, comprising:
   a plurality of fasteners, wherein each said fastener comprises:
      a first fastener portion; and
      a second fastener portion, wherein said first fastener portion is slidable relative to said second fastener portion; and
   a fastener cartridge body configured to removably store said fasteners, said fastener cartridge body comprising:
      a deck comprising a top surface;
      a plurality of fastener cavities configured to receive said first fastener portions, wherein each said fastener cavity comprises an opening in said deck; and
      a plurality of recesses defined in said deck, wherein each said recess surrounds a said opening, and wherein said second fastener portions are removably positioned in said recesses,
   wherein said second fastener portions are removably attached to said deck, wherein said second fastener portions are integrally molded with said deck, and wherein said first fastener portions are configured to contact said second fastener portions and dislodge said second fastener portions from said deck.

* * * * *